US012678287B2

(12) United States Patent　　　　(10) Patent No.:　US 12,678,287 B2

Christopher et al.　　　　　　　　　(45) Date of Patent:　Jul. 14, 2026

(54) CRANIOFACIAL IMPLANT INTEGRATING ULTRASOUND TECHNOLOGY

(71) Applicant: LONGEVITI NEURO SOLUTIONS, INC., Baltimore, MD (US)

(72) Inventors: Jesse Christopher, Hunt Valley, MD (US); Bradley Rabinovitz, Severna Park, MD (US); Lewis Parker, Leesburg, VA (US); David S. Zajc, Broadlands, VA (US)

(73) Assignee: LONGEVITI NEURO SOLUTIONS, INC., Baltimore, MD (US)

( * ) Notice: Subject to any disclaimer, the term of this patent is extended or adjusted under 35 U.S.C. 154(b) by 931 days.

(21) Appl. No.: 17/866,108

(22) Filed: Jul. 15, 2022

(65) Prior Publication Data

US 2023/0020551 A1　　　Jan. 19, 2023

Related U.S. Application Data

(60) Provisional application No. 63/261,095, filed on Sep. 10, 2021, provisional application No. 63/222,877, filed on Jul. 16, 2021.

(51) Int. Cl.
| | |
|---|---|
| *A61F 2/28* | (2006.01) |
| *A61B 8/00* | (2006.01) |
| *A61B 8/06* | (2006.01) |
| *A61F 2/30* | (2006.01) |
| *A61M 37/00* | (2006.01) |

(52) U.S. Cl.
CPC .............. *A61F 2/2875* (2013.01); *A61B 8/06* (2013.01); *A61B 8/4483* (2013.01); *A61M 37/0092* (2013.01); *A61F 2002/3009* (2013.01); *A61F 2002/30617* (2013.01)

(58) Field of Classification Search
CPC ............ A61F 2/2875; A61F 2002/3009; A61F 2002/30617; A61B 8/06; A61B 8/4483; A61B 8/4209; A61B 8/4472; A61B 8/54; A61M 37/0092
See application file for complete search history.

(56) References Cited

U.S. PATENT DOCUMENTS

| | | | |
|---|---|---|---|
| 4,183,249 A | 1/1980 | Anderson | |
| 4,206,762 A | 6/1980 | Cosman | |
| 5,201,715 A | 4/1993 | Masters | |

(Continued)

FOREIGN PATENT DOCUMENTS

| | | |
|---|---|---|
| EP | 0527651 A1 | 2/1993 |
| WO | 2017001911 A1 | 1/2017 |

(Continued)

OTHER PUBLICATIONS

Syed A. Quadri et al., High-intensity focused ultrasound: past, present, and future in neurosurgery, Neurosurgical Focus, vol. 44, Feb. 2018, 44 (2):E16, 2018.

(Continued)

*Primary Examiner* — Yashita Sharma
*Assistant Examiner* — Jose H. Trevino, III
(74) *Attorney, Agent, or Firm* — Welsh Flaxman & Gitler LLC

(57) ABSTRACT

A craniofacial implant includes a mounting plate, a low profile intercranial device including a static cranial implant and a functional neurosurgical implant, and an ultrasound transducer.

23 Claims, 36 Drawing Sheets

(56) References Cited

U.S. PATENT DOCUMENTS

| | | | |
|---|---|---|---|
| 5,275,165 | A | 1/1994 | Ettinger et al. |
| 5,902,326 | A | 5/1999 | Essar et al. |
| 5,983,123 | A | 11/1999 | Shmulewitz |
| 6,016,449 | A | 1/2000 | Fischell et al. |
| 6,061,593 | A | 5/2000 | Fischell et al. |
| 6,128,538 | A | 10/2000 | Fischell et al. |
| 6,134,477 | A | 10/2000 | Knuteson |
| 6,248,126 | B1 | 6/2001 | Lesser et al. |
| 6,354,299 | B1 | 3/2002 | Fischell et al. |
| 6,366,813 | B1 | 4/2002 | DiLorenzo |
| 6,427,086 | B1 | 7/2002 | Fischell et al. |
| 6,468,219 | B1 | 10/2002 | Njemanze |
| 6,647,296 | B2 | 11/2003 | Fischell et al. |
| 6,726,678 | B1 | 4/2004 | Nelson et al. |
| 6,819,956 | B2 | 11/2004 | DiLorenzo |
| 6,882,881 | B1 | 4/2005 | Lesser et al. |
| 7,004,948 | B1 | 2/2006 | Pianca et al. |
| 7,209,787 | B2 | 4/2007 | DiLorenzo |
| 7,231,254 | B2 | 6/2007 | DiLorenzo |
| 7,242,984 | B2 | 7/2007 | DiLorenzo |
| 7,277,758 | B2 | 10/2007 | DiLorenzo |
| 7,324,851 | B1 | 1/2008 | DiLorenzo |
| 7,596,399 | B2 | 9/2009 | Singhal et al. |
| 7,623,928 | B2 | 11/2009 | DiLorenzo |
| 7,647,097 | B2 | 1/2010 | Flaherty et al. |
| 7,717,853 | B2 | 5/2010 | Nita |
| 7,853,329 | B2 | 12/2010 | DiLorenzo |
| 7,917,222 | B1 | 3/2011 | Osorio et al. |
| 7,930,035 | B2 | 4/2011 | DiLorenzo |
| 8,050,767 | B2 | 11/2011 | Sheffield et al. |
| 8,116,875 | B2 | 2/2012 | Osypka et al. |
| 8,126,562 | B2 | 2/2012 | Fowler et al. |
| 8,235,903 | B2 | 8/2012 | Abraham |
| 8,306,607 | B1 | 11/2012 | Levi et al. |
| 8,337,413 | B2 | 12/2012 | Tauber et al. |
| 8,396,557 | B2 | 3/2013 | DiLorenzo |
| 8,454,701 | B2 | 6/2013 | Devauchelle |
| 8,540,631 | B2 | 9/2013 | Penner et al. |
| 8,591,562 | B2 | 11/2013 | D'Ambrosio et al. |
| 8,761,889 | B2 | 6/2014 | Wingeier et al. |
| 8,840,556 | B2 | 9/2014 | Lin et al. |
| 8,938,290 | B2 | 1/2015 | Wingeier et al. |
| 8,938,307 | B2 | 1/2015 | Boon et al. |
| 8,974,535 | B2 | 3/2015 | Antonyshyn et al. |
| 8,977,361 | B2 | 3/2015 | Carpentier et al. |
| 8,986,394 | B2 | 3/2015 | Liao et al. |
| 9,044,195 | B2 | 6/2015 | Manwaring et al. |
| 9,084,901 | B2 | 7/2015 | Wahlstrand |
| 9,101,756 | B1 | 8/2015 | Pianca et al. |
| 9,162,072 | B2 | 10/2015 | Singhal et al. |
| 9,440,064 | B2 | 9/2016 | Wingeier et al. |
| 9,462,958 | B2 | 10/2016 | Osorio et al. |
| 9,522,081 | B2 | 12/2016 | D'Ambrosio et al. |
| 9,592,124 | B2 | 3/2017 | Joganic |
| 9,592,377 | B2 | 3/2017 | Greenberg et al. |
| 9,764,510 | B2 | 9/2017 | Antonyshyn et al. |
| 9,883,944 | B2 | 2/2018 | Batty et al. |
| 9,993,337 | B1 | 6/2018 | Brogan et al. |
| 10,835,379 | B2 | 11/2020 | Gordon et al. |
| 10,980,436 | B2 | 4/2021 | Schmidt et al. |
| 10,981,021 | B2 | 4/2021 | Carpentier et al. |
| 10,987,524 | B2 | 4/2021 | Carpentier et al. |
| 11,058,541 | B2 | 7/2021 | Gordon |
| 11,135,455 | B2 | 10/2021 | Canney et al. |
| 11,154,401 | B2 | 10/2021 | Antonyshyn et al. |
| 11,298,232 | B2 | 4/2022 | Gordon |
| 2004/0073270 | A1 | 4/2004 | Firlik et al. |
| 2004/0267234 | A1 | 12/2004 | Heart et al. |
| 2007/0038100 | A1 | 2/2007 | Nita |
| 2012/0010711 | A1 | 1/2012 | Antonyshyn et al. |
| 2013/0204316 | A1 | 8/2013 | Carpentier et al. |
| 2014/0249454 | A1 | 9/2014 | Carpentier |
| 2014/0257262 | A1 | 9/2014 | Carpentier et al. |
| 2014/0330123 | A1 | 11/2014 | Manwaring et al. |
| 2015/0231415 | A1 | 8/2015 | Lewis et al. |
| 2016/0184100 | A1 | 6/2016 | Joganic |
| 2016/0185046 | A1 | 6/2016 | Littlefield |
| 2016/0193048 | A1 | 7/2016 | Prada |
| 2016/0296312 | A1 | 10/2016 | Kuhn et al. |
| 2017/0056240 | A1 | 3/2017 | D'Ambrosio et al. |
| 2017/0368330 | A1 | 12/2017 | Silay et al. |
| 2019/0030374 | A1* | 1/2019 | Carpentier ............... A61N 7/00 |
| 2019/0192298 | A1 | 6/2019 | Gordon et al. |
| 2019/0209228 | A1 | 7/2019 | Canney |
| 2019/0209328 | A1* | 7/2019 | Christopher ......... A61N 1/0539 |
| 2020/0030099 | A1 | 1/2020 | Sampath et al. |
| 2020/0138580 | A1 | 5/2020 | Carpentier et al. |
| 2020/0139159 | A1 | 5/2020 | Carpentier et al. |
| 2020/0197180 | A1* | 6/2020 | Christopher ......... A61B 5/0059 |
| 2021/0007756 | A1 | 1/2021 | Carpentier et al. |
| 2021/0267762 | A1 | 9/2021 | Sampath et al. |
| 2022/0047378 | A1 | 2/2022 | Gordon |
| 2022/0110607 | A1 | 4/2022 | Bouchoux et al. |

FOREIGN PATENT DOCUMENTS

| | | |
|---|---|---|
| WO | 2018076075 A1 | 5/2018 |
| WO | 2018154477 A1 | 8/2018 |
| WO | 2021050843 A1 | 3/2021 |
| WO | 2021050881 A1 | 3/2021 |
| WO | 2021105179 A1 | 6/2021 |
| WO | 2021175828 A1 | 9/2021 |
| WO | 2022175734 A1 | 8/2022 |

OTHER PUBLICATIONS

Shaunacy Ferro, Clear Cranial Implant Lets Doctors See Into The Brain, Popular Science, Sep. 4, 2013.
Laura Librizzi et al., Ultrasounds Induce Blood-Brain Barriwer Opening Across a Sonolucent Polyolefin Plate in an In Vitro Isolated Brain Preparation, Nature Portfolio, Scientific Reports, (2022) 12:2906, https://www.nature.com/articles/s41598-022-06791-7, Feb. 21, 2022.

* cited by examiner

304i

304

331

304o

304p

531e

531f

531g

531h 531a-e

704

US

1618

US

1710

1720

US

CRANIOFACIAL IMPLANT INTEGRATING ULTRASOUND TECHNOLOGY

REFERENCE TO RELATED APPLICATIONS

This application claims the benefit of U.S. Provisional Patent Application Nos. 63/222,877, filed Jul. 16, 2021, entitled "CRANIOFACIAL IMPLANT INTEGRATING ULTRASOUND TECHNOLOGY" and 63/261,095, filed Sep. 10, 2021, entitled "CRANIOFACIAL IMPLANT INTEGRATING ULTRASOUND TECHNOLOGY," both of which are incorporated herein by reference.

BACKGROUND OF THE INVENTION

Field of the Invention

The present invention generally relates to craniofacial implants integrating ultrasound technologies.

Description of Related Art

Craniectomies requiring skull reconstruction (i.e., cranioplasty) are often indicated for a multitude of etiologies including decompression (i.e., skull removal) following stroke or traumatic brain injury, bone flap infection (i.e., osteomyelitis) and/or bone flap resorption following previous neurosurgery, and/or oncological ablation for masses involving the underlying brain and/or skull. In the setting of traumatic brain injuries with cerebral edema, stroke (i.e., brain ischemia) with bleeding, and/or autologous bone flap resorption or osteomyelitic infections requiring removal, delayed cranioplasties are necessary at a secondary stage.

In fact, nearly 250,000 primary brain tumors/skull-based neoplasms are diagnosed each year resulting in a range of 4,500-5,000 second-stage implant cranioplasties per year (Berli J U, et al., "Immediate Single-Stage Cranioplasty Following Calvarial Resection for Benign and Malignant Skull Neoplasms Using Customized Craniofacial implants," The Journal of Craniofacial Surgery, Vol. 26, No. 5, September 2015).

The common types of cranial implants used today, in instances where the exact bone defect shape and size is known well in advance, are made most often from a variety of safe biomaterials (i.e., manmade), including titanium mesh, porous hydroxyapatite (HA), polymethylmethacrylate (PMMA), porous polyethylene, and polyether-ether-ketone (PEEK), among others. Of note, the most common "off-the-shelf" solution used by neurosurgeons and reconstructive surgeons is titanium mesh implants bent to serve as a "bridge"—simply spanning the skull defect from one side to another to create a non-specific curvature and protection barrier for the brain. The thin titanium mesh (which is 1 millimeter thick versus the normal skull thickness of 4-5 millimeters) accompanies several drawbacks and limitations including 1) non-anatomical thickness and secondary dead-space underneath, 2) a need to overlap neighboring skull areas for bridging and stability which can lead to visible deformities, pain, and/or scalp irregularities within the anterior craniofacial regions (i.e., non-hair bearing regions), and 3) a high risk of extrusion through the scalp when placed under thin and/or irradiated scalps. Ultimately, such mesh implants exhibit major differences in thickness and texture when compared to the resected anatomy of the patient.

A distinct subset of skull reconstruction patients includes craniectomy defects following oncological resection of calvarial lesions and/or brain tumors invading the skull. For this type of tumor ablative surgery, where tumors and/or processes (i.e., radiation therapy) involve the skull, cranioplasties to date have previously been performed using either 1) suboptimal hand-molding techniques with "off-the-shelf" products" or 2) a delayed, second surgery allowing the design and fabrication of a customized cranial implant. Now, with the advent of computer-aided design/manufacturing (CAD/CAM) and customized craniofacial implants, more suited alternatives are becoming widely available and have been published (Berli J U, et al., "Immediate Single-Stage Cranioplasty Following Calvarial Resection for Benign and Malignant Skull Neoplasms Using Customized Craniofacial implants," The Journal of Craniofacial Surgery, Vol. 26, No. 5, September 2015).

Using CAD/CAM fabrication, near-perfectly shaped custom cranial implants can be ordered and prefabricated with exact patient-specific curvatures to an oversized dimension, and then modified around the edges intra-operatively for an exact fit following bone/brain tumor resection as described by Gordon et al. (See, Gordon C R, et al., "Discussion of Usefulness of an Osteotomy Template for Skull Tumorectomy and Simultaneous Skull Reconstruction," The Journal of Craniofacial Surgery, Vol. 27, No. 6, September 2016; Berli J U, et al., "Immediate Single-Stage Cranioplasty Following Calvarial Resection for Benign and Malignant Skull Neoplasms Using Customized Craniofacial implants," The Journal of Craniofacial Surgery, Vol. 26, No. 5, September 2015).

Both non-invasive and invasive transcranial ultrasound have demonstrated numerous therapeutic/diagnostic applications including neuromodulation for movement disorders, magnetic resonance imaging (MRI)-guided lesion ablation, and local drug delivery via blood brain barrier disruption. Unfortunately, however, these emerging technologies remain limited by the acoustic properties of cranial bone causing ultrasonic wave attenuation, scattering and absorption. Hersh D S, Kim A J, Winkles J A, Eisenberg H M, Woodworth G F, Frenkel V. Emerging Applications of Therapeutic Ultrasound in Neuro-oncology: Moving Beyond Tumor Ablation. Neurosurgery. 2016; 79(5):643-654; Christian E, Yu C, Apuzzo M L J. Focused ultrasound: relevant history and prospects for the addition of mechanical energy to the neurosurgical armamentarium. World Neurosurg. 2014; 82(3-4):354-365; Quadri S A, Waqas M, Khan I, et al. High-intensity focused ultrasound: past, present, and future in neurosurgery. Neurosurg Focus. 2018; 44(2): E16; Weintraub D, Elias W J. The emerging role of transcranial magnetic resonance imaging guided focused ultrasound in functional neurosurgery. Mov Disord. 2017; 32(1):20-27; Carpentier A, Canney M, Vignot A, et al. Clinical trial of blood-brain barrier disruption by pulsed ultrasound. Sci Transl Med. 2016; 8(343):343re2; Gutierrez M I, Penilla E H, Leija L, Vera A, Garay J E, Aguilar G. Novel Cranial Implants of Yttria-Stabilized Zirconia as Acoustic Windows for Ultrasonic Brain Therapy. Adv HealthcMater. 2017; 6(21); Monteith S, Sheehan J, Medel R, et al. Potential intracranial applications of magnetic resonance-guided focused ultrasound surgery. J Neurosurg. 2013; 118(2):215-221; Vignon F, Shi W T, Yin X, Hoelscher T, Powers J E. The stripe artifact in transcranial ultrasound imaging. J Ultrasound Med. 2010; 29(12):1779-1786; Pinton G, Aubry J F, Bossy E, Muller M, Pernot M, Tanter M. Attenuation, scattering, and absorption of ultrasound in the skull bone. Med Phys. 2012; 39(1): 299-307.

Single stage cranioplasty presents a newfound opportunity for neurosurgeons to create a synthetic acoustic window by replacing normal bone with a cranial implant composed of sonolucent biomaterial, a material providing minimal to no obstruction of ultrasonic waves. A sonolucent cranial implant would thereby permit "trans-cranioplasty ultrasound" (TCU) for both diagnostic and therapeutic postoperative applications. Belzberg M, Ben Shalom N, Yuhanna E, Manbachi A, Tekes A, Huang J, Brem H, Gordon C, "Sonolucent Cranial Implants: Cadaveric study and Clinical Findings Supporting Diagnostic and Therapeutic Trans-Cranioplasty Ultrasound," J Craniofac Surg. July/August 2019-Volume 30-Issue 5-p 1456-1461.

SUMMARY

In one aspect a craniofacial implant includes a mounting plate, a low profile intercranial device including a static cranial implant and a functional neurosurgical implant, and an ultrasound transducer.

In some embodiments the craniofacial implant is manufactured from clear poly (methyl methacrylate) (PMMA).

In some embodiments the craniofacial implant is optically lucent, sonolucent, and radiolucent.

In some embodiments the craniofacial implant is sonolucent.

In some embodiments the craniofacial implant is radiolucent.

In some embodiments the functional neurosurgical implant includes an ultrasound transducer integrated with the static cranial implant.

In some embodiments the craniofacial implant includes an additional functional neurosurgical implant.

In another aspect a craniofacial implant includes a low profile intercranial device including a static cranial implant and a functional neurosurgical implant. The craniofacial implant also includes an ultrasound transducer that is separate and distinct from the static cranial implant, wherein the ultrasound transducer works in conjunction with the functional neurosurgical implant that has been integrated into the static cranial implant.

In some embodiments the static cranial implant includes an alignment feature.

In some embodiments the alignment feature includes a series of markings at different depths within the static cranial implant.

In some embodiments the series of markings includes an outer first static cranial implant marking and an inner second static cranial implant marking formed along an outer first surface and an inner second surface of the static cranial implant.

In some embodiments the outer first static cranial implant marking and the inner second static cranial implant marking are aligned such that when the ultrasound transducer is properly aligned with the markings, the ultrasound waves will be directed to the proper location within the cranium.

In some embodiments when one looks through the static cranial implant, the outer first static cranial implant marking and the inner second static cranial implant marking merge into a single location identifying image.

In some embodiments an ultrasound transducer is optimized for imaging and interacting with the neuro anatomy.

In some embodiments the ultrasound transducer is pre-set to frequencies, gain, and/or field of view that are optimal for brain imaging.

In some embodiments the static cranial implant is further provided with predefined locations for positioning of the ultrasound transducer.

In another aspect a craniofacial implant includes a low profile intercranial device having a static cranial implant and a functional neurosurgical implant. The craniofacial implant also includes an ultrasound transducer integrally formed with the static cranial implant, wherein the ultrasound transducer works in conjunction with the functional neurosurgical implant that has been integrated into the static cranial implant.

In some embodiments the ultrasound transducer takes the form of an array of ultrasound transducers that allows for the ability to automatically adjust the frequency and gain of the ultrasound transducers and imaging from different positions to assist in gathering the necessary image data that then may be processed for patient diagnosis and treatment.

In some embodiments ultrasound imaging through the static cranial implant allows for imaging confirmation of blood flow immediately after surgery.

In some embodiments ultrasound imaging through the static cranial implant allows for imaging confirmation of blood flow during follow-up examinations.

In some embodiments ultrasound imaging through the static cranial implant allows for imaging confirmation of blood flow to desired locations within the brain.

In some embodiments ultrasound imaging through the static cranial implant allows for imaging visualization of, and guidance during, interventional procedures to guide a wire and/or catheter through the neurovasculature to a desired location in the brain.

In some embodiments ultrasound imaging through the static cranial implant allows for activation of a contrast agent as it passes a particular point of interest and is subjected to ultrasound for activation thereof.

In some embodiments ultrasound imaging through the static cranial implant allows for drug delivery.

In some embodiments ultrasound imaging through the static cranial implant allows for drug delivery by subjecting a drug to ultrasound at a specific location within the brain so that the drug is active at a highly specific location, or to enhance the effectiveness of the drug through delivery of ultrasound, regardless whether the drug is delivered by direct injection into the brain or is introduced indirectly such as parentally or through an endovascular catheter introduced to a desired location in the brain for this purpose.

In some embodiments ultrasound imaging through the static cranial implant allows for drug delivery by subjecting the drug to ultrasound at a specific location within the brain to assist the drug in passing through the brain blood barrier, such as by causing brain cells to open up to permit larger sized molecules to pass.

In some embodiments ultrasound imaging through the static cranial implant allows for drug delivery by therapeutically releasing nano-encapsulated drugs through the application of ultrasound wherein the ultrasound breaks down the encapsulation material to release the drug.

In another aspect a craniofacial implant includes a low profile intercranial device including a static cranial implant and a functional neurosurgical implant. The craniofacial implant also includes an ultrasound transducer working in conjunction with the functional neurosurgical implant in conjunction with the application of radiation.

In some embodiments therapeutic or imaging radiation may be delivered through or from the static cranial implant and that radiation may be observed and/or manipulated using the ultrasound transducer.

In some embodiments a shielded radiation source is positioned in the cranial implant and the radiation subsequently exposed by opening a window of the shield or moving/rotating a portion of the shield to expose the brain to the radiation.

In some embodiments the radiation is in the form of nano-encapsulated radiation seeds wherein the ultrasound breaks down the encapsulation material to release the radiation seed.

In some embodiments the radiation is in the form of small radiation seeds housed in a shielded portion of the static cranial implant, and the radiation seeds are selectively deployed from the shielded portion to the brain via a catheter that extends from the static cranial implant to a targeted portion of the brain for periodic radiation delivery.

In another aspect a craniofacial implant includes a low profile intercranial device including a static cranial implant and a functional neurosurgical implant. The craniofacial implant also includes an ultrasound transducer integrated into a wearable wireless ultrasound transducer.

In some embodiments the wearable wireless ultrasound transducer includes a support assembly providing for movement of the ultrasound transducer in two dimensions.

In some embodiments the support assembly is an XY gantry with a carriage supporting the ultrasound transducer.

In another aspect a craniofacial implant includes a low profile intercranial device including a static cranial implant and a functional neurosurgical implant. The craniofacial implant also includes an ultrasound transducer producing data that is combined with imaging data from other imaging technologies.

In some embodiments the other imaging technologies includes CT (computed tomography), MRI (magnetic resonance imaging), fMRI (functional magnetic resonance imaging), or X-Ray.

In another aspect a craniofacial implant includes a low profile intercranial device including a static cranial implant and a functional neurosurgical implant. The craniofacial implant also includes an ultrasound transducer. The static cranial implant is provided with a unique marking and triangle mapping is achieved with markings to enable inter-imaging co-registration, overlay, interdigitation, integration, and/or orientation.

In another aspect a craniofacial implant includes a low profile intercranial device including a static cranial implant and a functional neurosurgical implant. The craniofacial implant also includes an ultrasound transducer, wherein the imaging data produced in accordance with the present invention is applied in the provision of a real-time surgical augmented reality experience.

In another aspect a craniofacial implant includes a low profile intercranial device including a static cranial implant and a functional neurosurgical implant. The craniofacial implant also includes an ultrasound transducer, wherein the imaging data is applied in the production of 3D ultrasound images.

In another aspect a craniofacial implant includes a low profile intercranial device including a static cranial implant and a functional neurosurgical implant. The craniofacial implant also includes an ultrasound transducer, wherein the static cranial implant is a reconstructive device that replaces the skull and encapsulates a medicine such that ultrasound waves pass therethrough and the encapsulation of the medicine is triggered to release medicine when ultrasound waves contact it.

In another aspect a craniofacial implant includes a low profile intercranial device having a static cranial implant and a functional neurosurgical implant. The craniofacial implant also includes an ultrasound transducer. The static cranial implant is a reconstructive implant that replaces the skull in a trajectory that allows for ultrasound to pass through and dilate the blood brain barrier, wherein the static cranial implant also encapsulates a medicine and allows ultrasound waves to pass therethrough and the encapsulation of the medicine is triggered to release medicine when ultrasound waves contact it.

In another aspect a craniofacial implant includes a low profile intercranial device including a static cranial implant and a functional neurosurgical implant. The craniofacial implant also includes an ultrasound transducer. The static cranial implant includes a reservoir of medicine, with or without a catheter leading to a specific anatomical target, within a reconstructive cranial implant, and the static cranial implant allows for ultrasound waves to pass through, open the reservoir, and the medicine is delivered to the intended target.

In another aspect a craniofacial implant includes a low profile intercranial device including a static cranial implant and a functional neurosurgical implant. The craniofacial implant also includes an ultrasound transducer, wherein the static cranial implant includes a medicine pump capable of perfusing medicine to a specific anatomical target. The medicine pump is positioned within the static cranial implant. The pump and static cranial implant are made of or impregnated within sonolucent material allowing release of the medicine held within a reservoir associated with the pump when triggered with ultrasound.

Other objects and advantages of the present invention will become apparent from the following detailed description when viewed in conjunction with the accompanying drawings, which set forth certain embodiments of the invention.

DETAILED DESCRIPTION

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to the various figures, the present invention relates to craniofacial implants used in conjunction with ultrasound technology to enhance the diagnosis and treatment of neurological disorders.

The present invention makes use of prefabricated craniofacial implants made of "clear" translucent materials, including, but not limited to, man-made alloplastic or other tissue engineered materials, to allow and improve a surgeon's ability to view, through imaging and/or direct visualization, a cranial, craniofacial, and/or facial defect, as well as the underlying brain anatomy.

Figure 1:
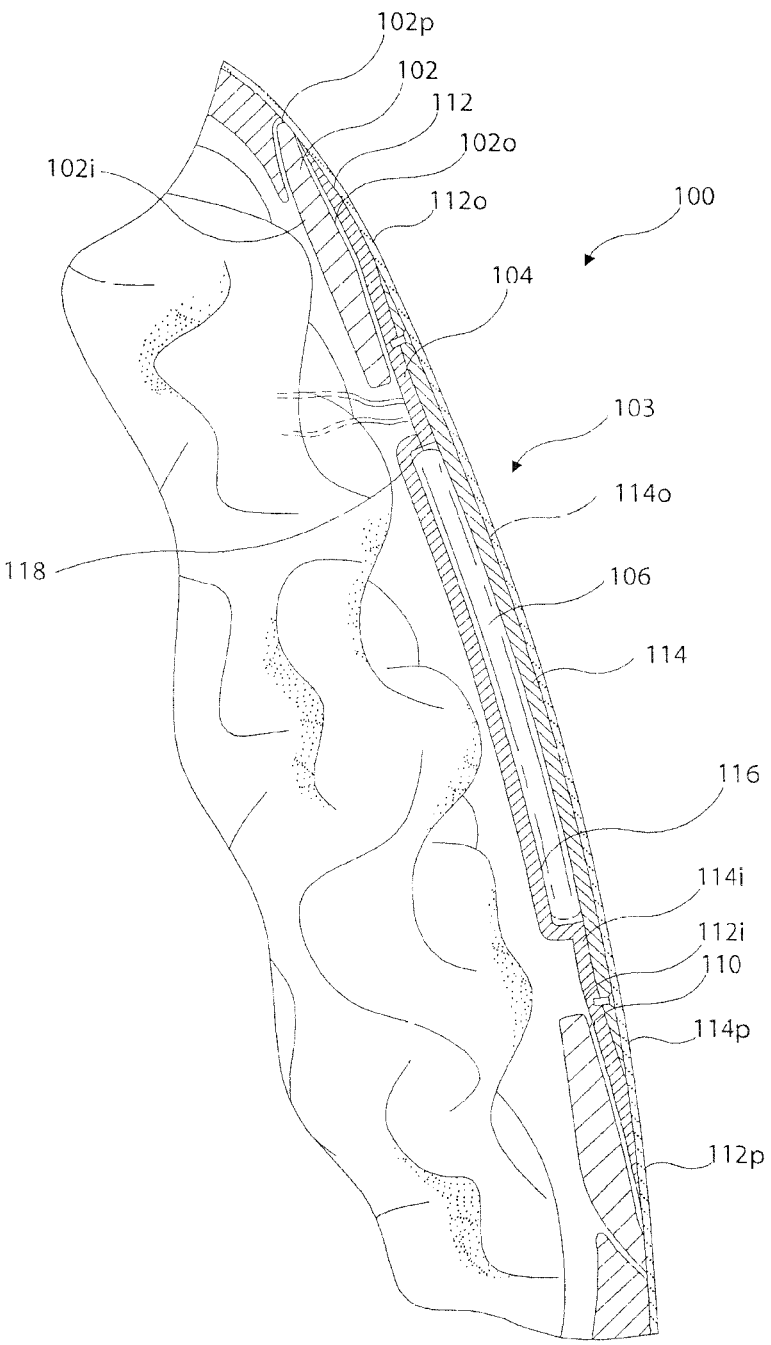
FIG. 1 is a cross section view of a craniofacial implant in accordance with a first embodiment.
Figure 2:
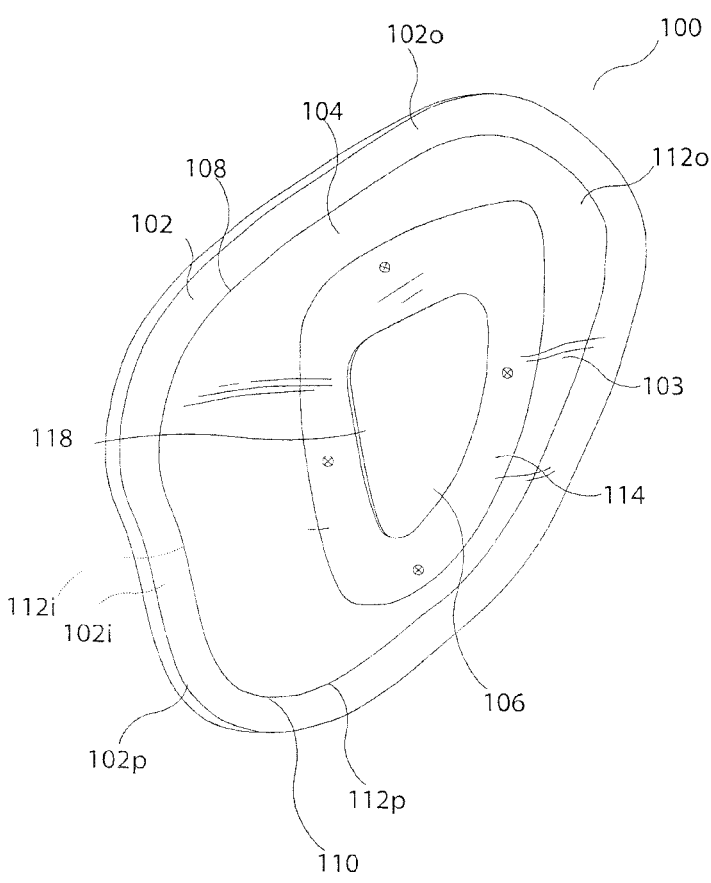
FIG. 2 is a perspective view of the craniofacial implant shown in FIG. 1.
Figure 3:
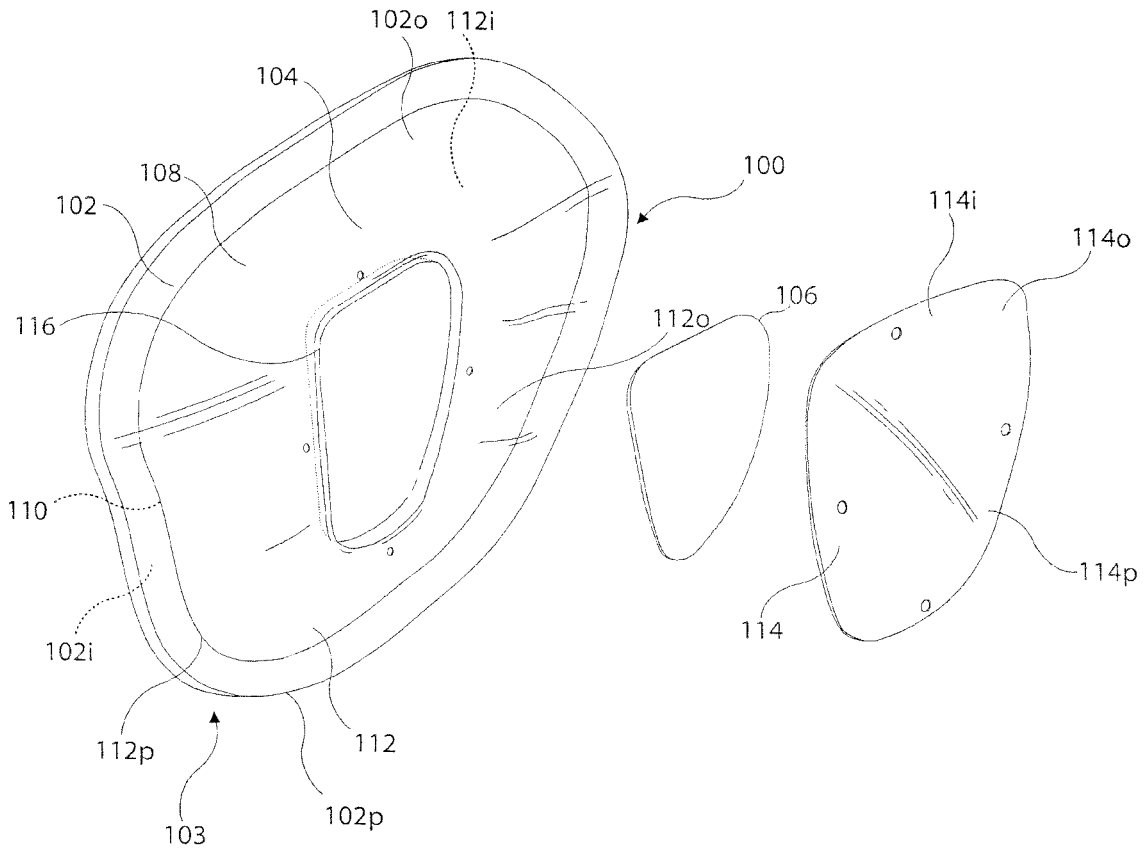
FIG. 3 is an exploded view of the craniofacial implant shown in FIG. 1.

In accordance with a disclosed embodiment of the present invention as shown in FIGS. 1, 2, and 3, the sonolucent craniofacial implant 100 with transparency, in particular, the static cranial implant 104 of the craniofacial implant 100, is a prefabricated implant preferably manufactured from clear sonolucent poly (methyl methacrylate) (PMMA) or any other clear biocompatible material suited for safe use in craniofacial reconstruction. While a clear PMMA sonolucent craniofacial implant 100 is used in accordance with a disclosed embodiment as discussed herein, it is appreciated the prefabricated craniofacial implant 100 may include a polymer, metal, bioengineered material, or any combinations thereof. For example, the prefabricated craniofacial implant 100 may further include any biomaterial that allows sonolucency and enhanced visibility with complete translucency.

It is appreciated the use of the term "craniofacial implant" herein is intended to include all implants that may be used in conjunction with skull reconstruction procedures, facial reconstruction, or any combination thereof.

As used herein the term "clear" is intended to refer to a material that is substantially completely transparent (for example, the craniofacial implant 100 is completely transparent with the exception of a neurological device(s) that might be integrated into the craniofacial implant 100 and which does not otherwise impede the ability to achieve the underlying principles of the invention) and exhibits the property of transmitting rays of light through its substance so that bodies situated beyond or behind can be distinctly seen when looking through the material.

The "translucent" character of the craniofacial implant 100 allows for real-time transmission of light, which is critical for future applications related to any and all battery-powered, low-profile intercranial devices capable of neuromodulation (i.e., implanted functional RNS (Responsive Neurostimulation) systems like those manufactured by NeuroPace) and capable of sending wireless electrocorticography (ECoG) signals for data collection, interpretation, treatment, and intervention; and a multitude of other wavelength-related mediums like optical coherence tomography (OCT) imaging and ultrasound imaging—as described by Gordon et al in International Patent Application PCT/US2016/030447, filed May 2, 2016 entitled "LOW PROFILE INTERCRANIAL DEVICE" (published as WO 2017/039762), and U.S. patent application Ser. No. 15/669,268, filed Aug. 4, 2017, entitled "METHOD FOR MANUFACTURING A LOW-PROFILE INTERCRANIAL DEVICE AND THE LOW-PROFILE INTERCRANIAL DEVICE MANUFACTURED THEREBY" (published as U.S. Patent Application Publication No. 2018/0055640), which claims the benefit of U.S. Provisional Patent Application 62/381, 242, filed Aug. 30, 2016, entitled "METHOD FOR MANUFACTURING A LOW-PROFILE INTERCRANIAL DEVICE AND THE LOW-PROFILE INTERCRANIAL DEVICE MANUFACTURED THEREBY," all of which are incorporated herein by reference. In summary, the utilization of an optically lucent, sonolucent, and radiolucent material provides for photoacoustic mapping, remote stimulation, ablation, and imaging of neurophysiology, as well as dilation of the blood brain barrier.

Still further, and as briefly mentioned above, the craniofacial implant 100 is manufactured to allow for the transmission of waves other than optical light waves, in particular, the craniofacial implant 100 is sonolucent (that is, allowing passage of ultrasonic waves without production of echoes that are due to reflection of some of the waves). The craniofacial implant 100 may also be radiolucent (that is, allowing passage of radio waves without production of echoes that are due to reflection of some of the waves).

By way of example, the craniofacial implant 100 may be manufactured in a manner allowing for the transmission of ultrasonic waves as described in U.S. Pat. No. 9,044,195, entitled "IMPLANTABLE SONIC WINDOW," ('195 patent) which is incorporated herein by reference. As explained in the '195 patent, a strong, porous sonically translucent material through which ultrasonic waves can pass for purposes of imaging the brain is employed, wherein the material is a polymeric material, such as polyethylene, polystyrene, acrylic, or poly (methyl methacrylate) (PMMA). In addition, U.S. Pat. No. 9,535,192, entitled "METHOD OF MAKING WAVEGUIDE-LIKE STRUCTURES," ('192 Publication) and U.S. Patent Application Publication No. 2017/0156596, entitled "CRANIAL IMPLANTS FOR LASER IMAGING AND THERAPY," ('596 Publication) both of which are incorporated herein by reference, discloses making waveguide-like structures within optically transparent materials using femtosecond laser pulses wherein the optically transparent materials are expressly used in the manufacture of cranial implants. The '596 publication explains the use of optically transparent cranial implants and procedures using the implants for the delivery of laser light into shallow and/or deep brain tissue. The administration of the laser light can be used on demand, thus allowing real-time and highly precise visualization and treatment of various pathologies. Further still, Tobias et al. describe an ultrasound window to perform scanned, focused ultrasound hyperthermia treatments of brain tumors. Tobias et al., "ULTRASOUND WINDOW TO PERFORM SCANNED, FOCUSED ULTRASOUND HYPERTHERMIA TREATMENTS OF BRAIN TUMORS," Med. Phys. 14(2), March/April 1987, 228-234, which is incorporated herein by reference. Tobias et al. tested various materials to determine which material would best serve as an acoustical window in the skull and ultimately determined polyethylene transmitted a larger percentage of power than other plastics and would likely function well as an ultrasonic window. Further still, Fuller et al., "REAL TIME IMAGING WITH THE SONIC WINDOW: A POCKET-SIZED, C-SCAN, MEDICAL ULTRASOUND DEVICE," IEEE International Ultrasonics Symposium Proceedings, 2009, 196-199, which is incorporated herein by reference, provides further information regarding sonic windows.

Radiolucency as applied to the present invention allows a clinician to see the anatomy surrounding the clear craniofacial implant 100 without "scatter" or interfering artifacts from the implant for diagnosis and follow-up. By another definition of radiolucency, radio waves are able to transmit easily through the craniofacial implant 100, for example, via Bluetooth or other frequency transmission, which can serve many purposes including, but not limited to, data management and controller telemetry. The provision of radiolucency also allows for the integration of markings (as discussed below) made with radiographic materials, for example, barium sulfate, to be visible in contrast to the remainder of the craniofacial implant 100 to allow for unique device identifiers or unique patient information to be visible on post-operative scans. Radiolucency also allows for the use of radio frequency (RF) therapeutics in conjunction with the craniofacial implant described herein. For example, RF ablation for cancer is known to be an effective mechanism that employs electrical energy and heat to destroy cancer cells.

Considering the provision of optical lucency, that is, the transparent and/or translucent character of the material construction of the present craniofacial implant 100, the ability to optically transmit through the craniofacial implant 100 allows for visualization of anatomy distal to the craniofacial implant 100 (as previously described), allows for the potential of higher bandwidth optical links (similar to radio transmission) between proximal adjunct devices, allows for light to be emitted from the craniofacial implant 100 to adjacent anatomy which could aid in optogenetics, and allows for imaging/therapeutic modalities that rely on light like optical coherence tomography from within the craniofacial implant.

The craniofacial implant 100 may be of the type described in International Patent Application PCT/US2016/030447, filed May 2, 2017, entitled "LOW PROFILE INTERCRANIAL DEVICE," (published as WO 2017/039762), U.S. patent application Ser. No. 15/669,268, filed Aug. 4, 2017, entitled "METHOD FOR MANUFACTURING A LOW-PROFILE INTERCRANIAL DEVICE AND THE LOW-PROFILE INTERCRANIAL DEVICE MANUFACTURED THEREBY" (published as U.S. Patent Application Publication No. 2018/0055640), and U.S. patent application Ser. No. 16/203,357, filed Nov. 28, 2018, entitled "UNIVERSAL LOW-PROFILE INTERCRANIAL ASSEMBLY" (published as U.S. Patent Application Publication No. 2019/0209328), all of which are incorporated herein by reference.

While an embodiment of a specific craniofacial implant body, which is a custom implant, is disclosed below with reference to FIGS. 1, 2, and 3, it is appreciated the craniofacial implant may be of a non-custom construction. Such a non-custom embodiment would include the functional features of the craniofacial implants disclosed herein, but would be manufactured in a manner that is not specific to a patient and as such the resected portion of the skull would be shaped to match the craniofacial implant.

In accordance with the embodiment disclosed with reference to FIGS. 1, 2, and 3, the craniofacial implant 100 is a universal low-profile intercranial assembly. The universal low-profile intercranial assembly 100 is generally composed of a mounting plate 102 into which a low profile intercranial device 103, composed of a static cranial implant 104 and a functional neurosurgical implant 106, is mounted. This combination of elements results in the universal low-profile intercranial assembly 100 that provides a mechanism whereby various low profile intercranial devices 103 may be implanted as desired and needed based upon the progress of a patient undergoing cranial and/or brain-based treatments.

The mounting plate 102 includes a hollowed-out center aperture 108 shaped and dimensioned for the ready placement and mounting of the low profile intercranial device 103 therein. The mounting plate 102 is specifically shaped and dimensioned for intercranial placement within the cranial defect while simultaneously providing a center aperture 108 into which a low profile intercranial device 103 may be readily mounted. Given that the center aperture 108 of the mounting plate 102 is of a known shape, which may be readily replicated and controlled, the shape of the low profile intercranial device 103 can be readily controlled to allow for immediate and exact placement of the low profile intercranial device 103 within the center aperture 108. This allows for a first low profile intercranial device 103 to be implanted and used at a first stage of a patient's treatment and subsequently removed and replaced with a second low profile intercranial device at a second stage of the patient's treatment.

The mounting plate 102 includes an outer (commonly convex) first surface 102o, an inner (commonly concave) second surface 102i, and a peripheral edge 102p extending between the outer first surface 102o and the inner second surface 102i. The mounting plate 102 is shaped and dimensioned for engagement with the skull of the patient upon implantation in a manner well known to those skilled in the field of neurosurgical procedures. The outer first surface 102o and inner second surface 102i of the mounting plate 102 are preferably curved in a superior to inferior direction, a posterior to anterior direction, and a medial to lateral direction. In addition, the peripheral edge 102p has a substantial taper for resting upon a matching taper formed along the skull. It is, however, appreciated that this taper may vary (or not exist at all, that is, the peripheral edge 102p may be substantially perpendicular relative to the outer first surface 102o and the inner second surface 102i) depending upon the specific needs of the procedure. In accordance with a preferred embodiment, the mounting plate 102 will have a preselected thickness not exceeding the space between the inner surface of the scalp and the outer surface of the dura, for example, in the range of around 1 millimeter to 25 millimeters (with areas of strategic bulking and/or thinning) and depending upon the strength of the materials used in the construction of the mounting plate 102. Preferably, the mounting plate 102 will have a thickness of 1 millimeter to 12 millimeters. As mentioned above, the mounting plate 102 also includes a center aperture 108 designed to accommodate the static cranial implant 104. The center aperture 108 is defined by an inner wall 110 extending between the outer first surface 102o and the inner second surface 102i of the mounting plate 102.

Considering the sonolucent static cranial implant 104, it should first be appreciated, the term "static" is used in the description of the present invention because the static cranial implant 104, has no encapsulated inner working (i.e., "functional") parts, batteries, wires, or computers, and is essentially an improved "empty-shell" which optimizes the inter-implant positioning within the confines of the skull and the neighboring functional neurosurgical implant 106.

The static cranial implant 104 has a two-piece construction allowing for ready access to the functional neurosurgical implant 106 without the need for complete removal of the low-profile intercranial device. The two-piece static cranial implant 104 includes a base cranial implant member 112 and a cover cranial implant member 114. The base cranial implant member 112 has a geometry that substantially conforms to a resected portion of the patient's anatomy to which the low-profile intercranial device is to be secured. The base cranial implant member 112 includes an outer (commonly convex) first surface 112*o*, an inner (commonly concave) second surface 112*i*, and a peripheral edge 112*p* extending between the outer first surface 112*o* and the inner second surface 112*i*. The outer first surface 112*o* and inner second surface 112*i* of the base cranial implant member 112 are preferably curved in a superior to inferior direction, a posterior to anterior direction, and a medial to lateral direction.

The base cranial implant member 112 also includes a center recess 116 formed along the outer first surface 112*o* and optional structural elements, for example, tunnels, channels, pockets, access holes, and/or other structural elements, designed to accommodate various features of the functional neurosurgical implant 106.

In addition to the base cranial implant member 112, the two-piece static cranial implant 104 includes a cover cranial implant member 114. The cover cranial implant member 114 is shaped and dimensioned for positioning over the center recess 116 along the outer first surface 112*o* of the base cranial implant member 112. In accordance with a preferred embodiment, the cover cranial implant member 114 is secured to the base cranial implant member 112 by screw fixation. The cover cranial implant member 114 includes an outer (commonly convex) first surface 114*o*, an inner (commonly concave) second surface 114*i*, and a peripheral edge 114*p* shaped and dimensioned for engagement with the outer first surface 112*o* of the base cranial implant member 112 along the periphery of the center recess 116. As with the base cranial implant member 112, the outer first surface 114*o* and inner second surface 114*i* of the cover cranial implant member 114 are preferably curved in a superior to inferior direction, a posterior to anterior direction, and a medial to lateral direction.

The base cranial implant member 112 and the cover cranial implant member 114 have a total thickness similar to that of the embodiment described above, that is, and depending on the strength characteristics of the materials used, the base cranial implant member 112 and the cover cranial implant member 114 will have a thickness (with areas of strategic bulking and/or thinning) of around 1 millimeter to 25 millimeters, preferably, 1 millimeter to 12 millimeters.

The cover cranial implant member 114 fits over the center recess 116 along the outer first surface 112*o* of the base cranial implant member 112. In this way, the inner second surface 114*i* of the cover cranial implant member 114 and the outer first surface 112*o* of the base cranial implant member 112, along the center recess 116, define a center cavity 118 configured to conform to the exact requirements of the functional neurosurgical implant 106 in accordance with the present invention. With this in mind, the inner second surface 114*i* of the cover cranial implant member 114 may be shaped and/or contoured to enhance the positioning of the functional neurosurgical implant 106 within the center cavity 118.

As will be appreciated based upon the various embodiments disclosed herein, the functional neurosurgical implant 106 of the present invention is selected from a variety of FDA-approved and experimental options for electrical, optical, mechanical, medicinal, and other treatment/monitoring devices designed for long term invasive treatment and/or disease-monitoring of patients requiring such attention. These functional neurosurgical implants are known devices manufactured by various vendors within the neurosurgical industry and have known, unmodifiable dimensions that may be used in the modification of the static cranial implant 104 to optimize surgical results by minimizing abnormal shapes, visible contours, and/or craniofacial deformities. For example, recent work regarding Alzheimer's disease has revealed that ultrasound is effective in treating those people afflicted with the diseases. G. Leinenga, J. Götz, Scanning ultrasound removes amyloid-b and restores memory in an Alzheimer's disease mouse model. Sci. Transl. Med. 7, 278ra33 (2015).

In accordance with the embodiment disclosed with reference to FIGS. 1, 2, and 3, and as discussed below in greater detail, the ultrasound transducer is integrated with the static cranial implant 104 and would therefore function as the functional neurosurgical implant 106 as described above (or, as described below in conjunction with other embodiments, the ultrasound transducer may be separate and distinct from the static cranial implant and would therefore function in conjunction with the functional neurosurgical implant selected for use in the treatment of patient). These different embodiments offer distinct advantages that will be discussed below in detail. It appreciated ultrasound transducers as described for use in accordance with the various embodiments described herein are devices generating/transmitting sound waves and receiving the resultant echoes resulting from the sound waves bouncing off the body matter. The received echoes are then sent to a computer where they are processed and converted into images. It is further appreciated the terms ultrasound transducer and probe are commonly used interchangeably.

Ultrasound Transducer Integrated with the Static Cranial Implant

In accordance with one embodiment as shown in FIGS. 1, 2, and 3, the functional neurosurgical implant 106 is an ultrasound transducer mounted within the static cranial implant 104. Although not shown in the drawings, it is appreciated additional functional neurosurgical implants, in addition to the ultrasound transducer, that may be used, but are not limited to the following, include: Deep Brain Stimulators (DBS); Cortical Brain Stimulators (CBS); neurologic medicines that are otherwise prevented from diffusing through the blood-brain barrier via common delivery methods; battery/passively/kinetically/or otherwise-powered functional devices including neuromodulation devices, imaging devices, radiation therapy devices, and remote sensing/monitoring devices; monitoring devices for abnormal levels of intracranial pressure (ICP) or brain activity (i.e., seizures), such as an electrical array for motor/vision cortex control, battery/passively/kinetically/or otherwise-based stimulation hardware for epilepsy management (grids/batteries/wires); low-profile remote imaging devices (e.g., optical coherence tomography (OCT)); delivery/sensing devices for electrical impulses; neurological and physiological systems required for deep space/sleep functionalities enhancing the monitoring and/or maintenance of bodily vital signs, nutrition, cognition, etc.; convection enhanced delivery systems effectively delivering therapeutics to substantial volumes of brain and brain tumor; and remote neuro-imaging devices (i.e., electroencephalogram (EEG).

Figure 12:
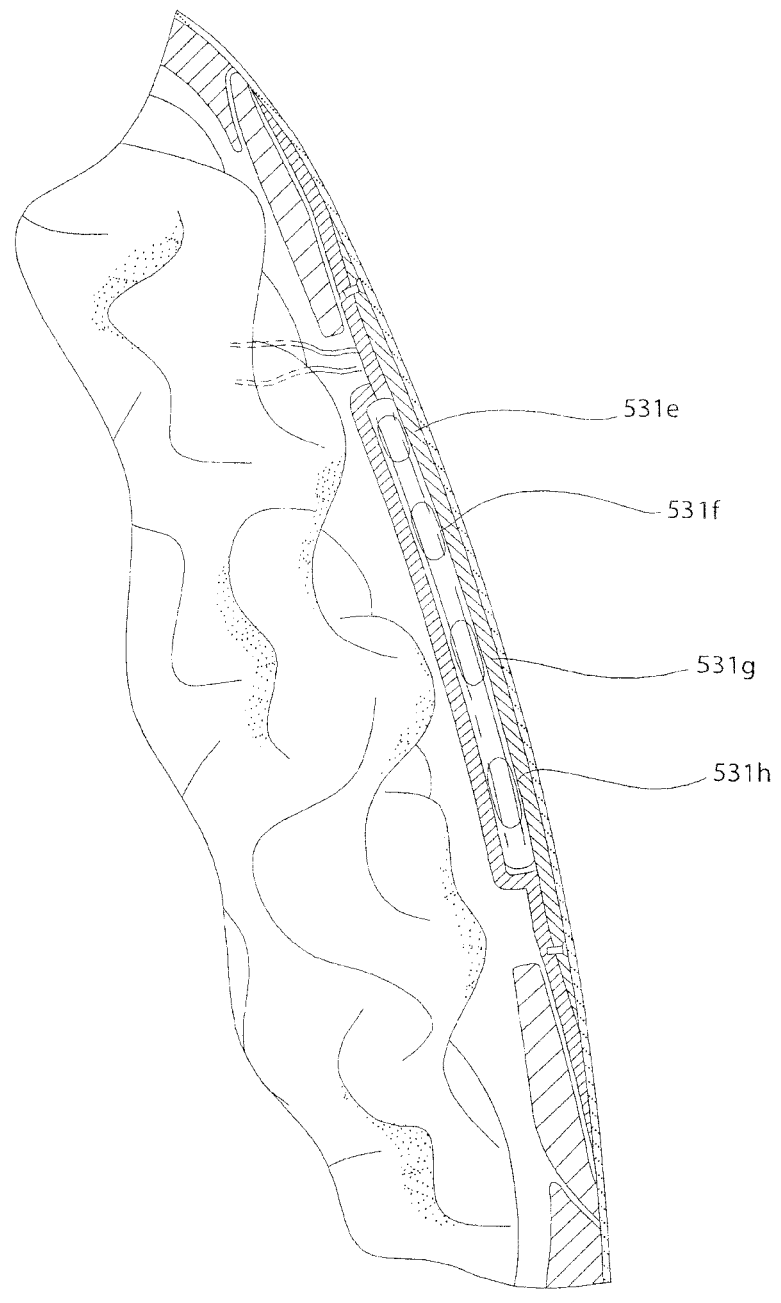
FIG. 12 is a cross section view of a craniofacial implant in accordance with a fifth embodiment.
Figure 13:
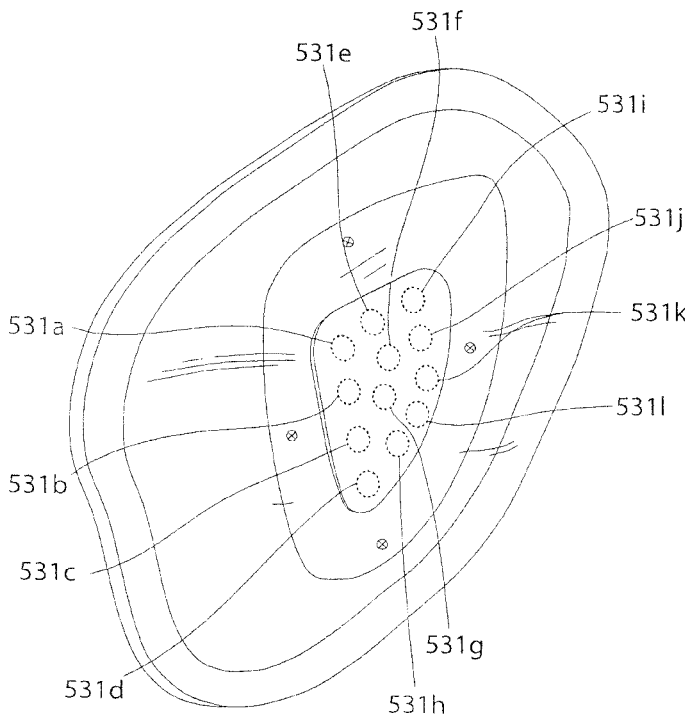
FIG. 13 is a perspective view of the craniofacial implant shown in FIG. 12.
Figure 14:
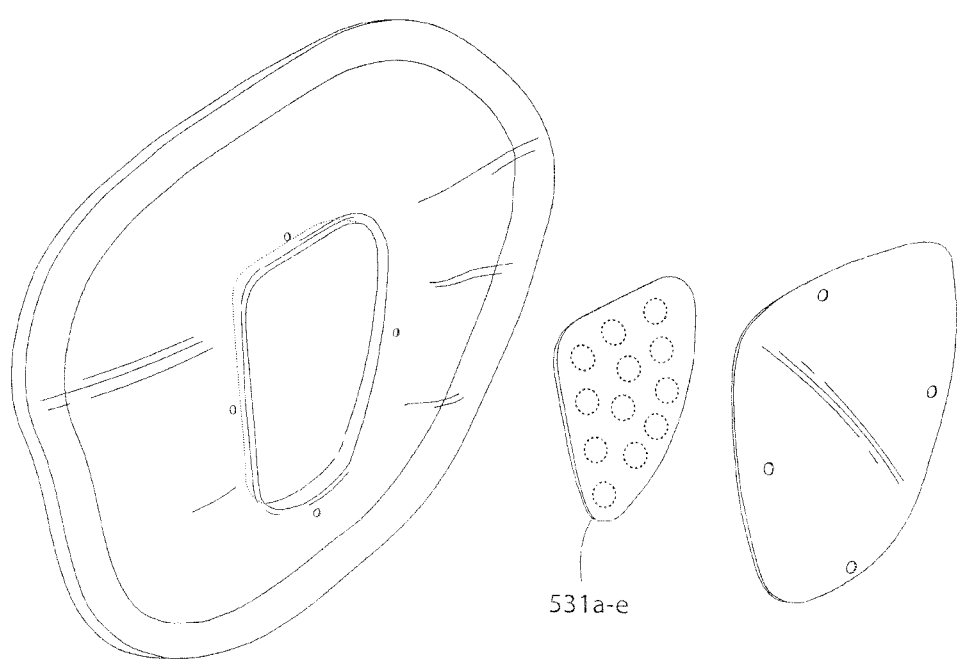
FIG. 14 is an exploded view of the craniofacial implant shown in FIG. 12.

Considering alternate embodiments relating to an ultrasound transducer 106 mounted within the cavity 118 of the static cranial implant 104 as disclosed with reference to FIGS. 1, 2, and 3, the ultrasound transducer may take the form of an array of ultrasound transducers 531*a*-1 as shown in FIGS. 12, 13, and 14. As such, and in addition to the ability to automatically adjust the frequency and gain of the ultrasound transducers, the array of ultrasound transducers 531*a*-1 allows imaging from different positions to assist in gathering the necessary image data that then may be processed for patient diagnosis and treatment.

Ultrasound Transducer Separate and Distinct from the Static Cranial Implant

Figure 4:
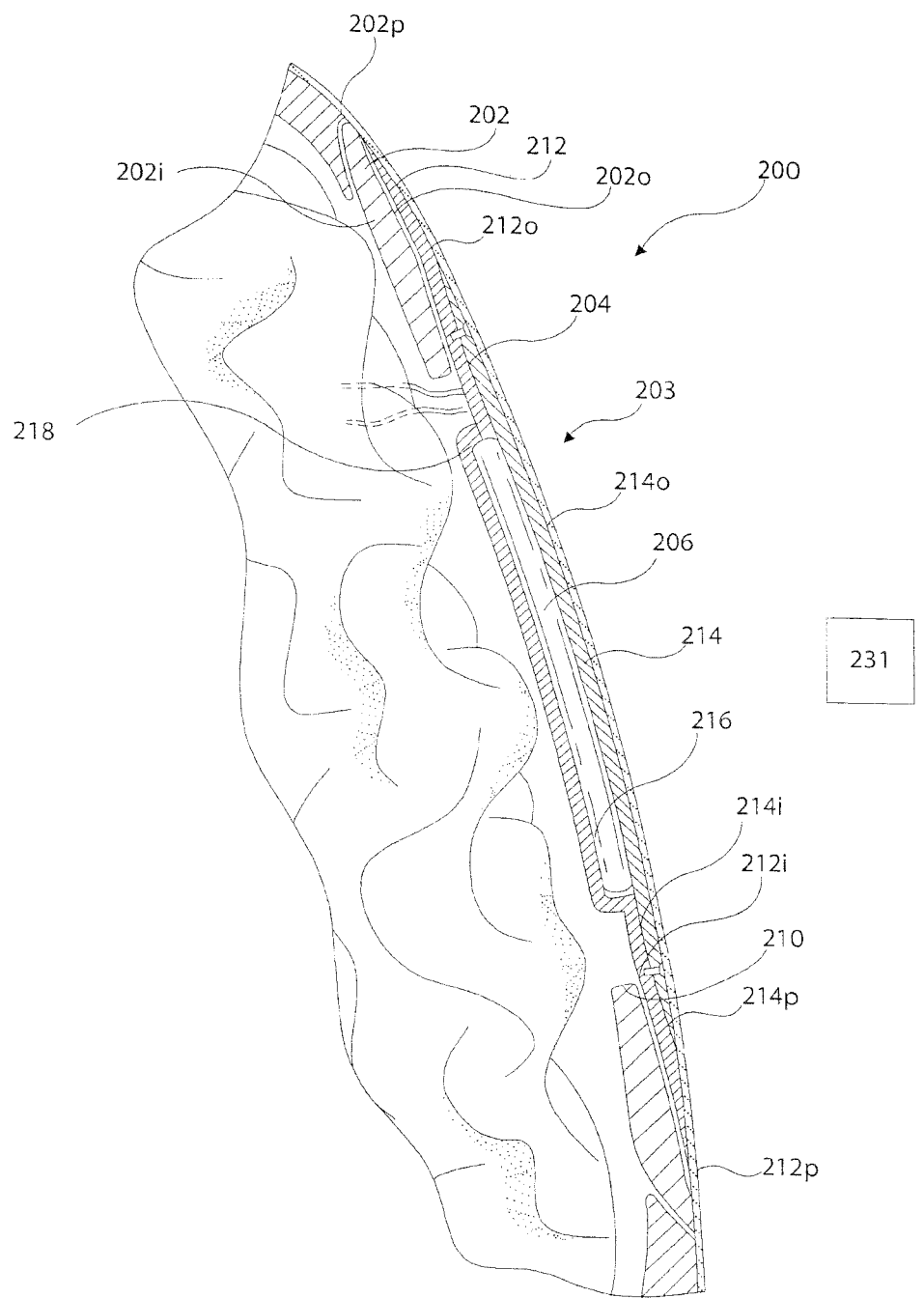
FIG. 4 is a cross section view of a craniofacial implant in accordance with a second embodiment.
Figure 5:
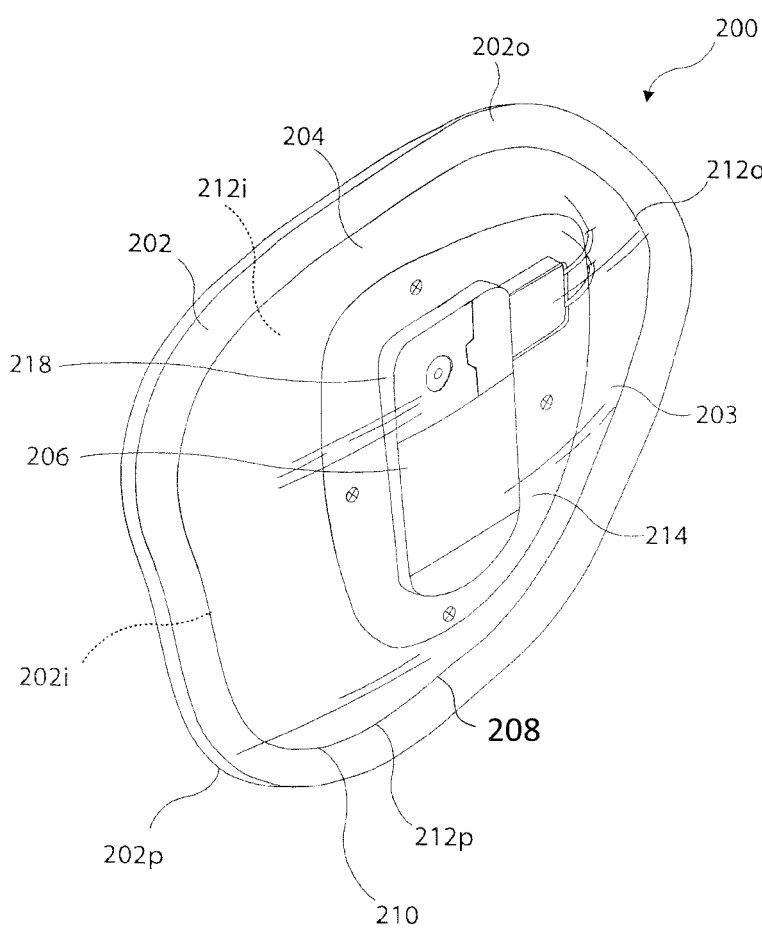
FIG. 5 is a perspective view of the craniofacial implant shown in FIG. 4.
Figure 6:
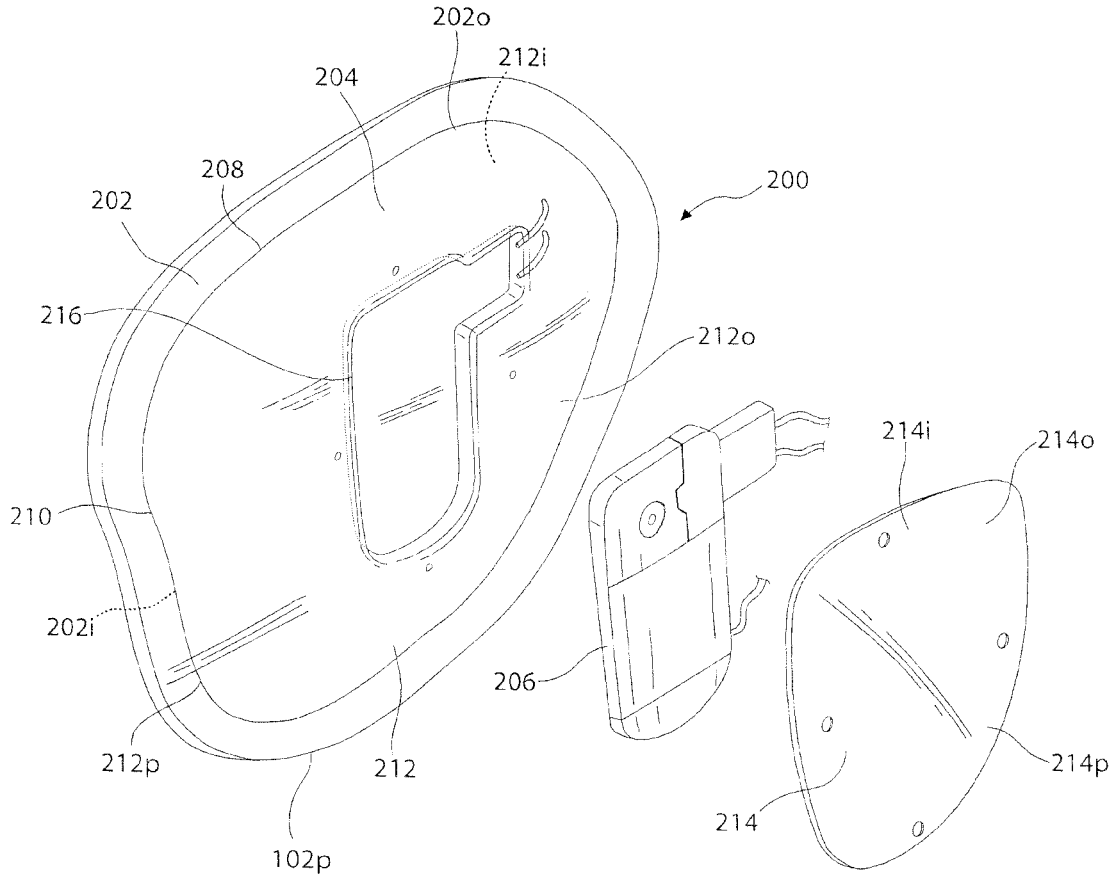
FIG. 6 is an exploded view of the craniofacial implant shown in FIG. 4.

As briefly discussed above, and in accordance with another embodiment as shown in FIGS. 4, 5, and 6, the ultrasound transducer 231 is separate and distinct from the sonolucent static cranial implant 204. As such, the ultrasound transducer 231 works in conjunction with the static cranial implant 204 and a functional neurosurgical implant 206 that has been integrated into the static cranial implant 204.

As with the prior embodiment, the static cranial implant 204 with transparency is a prefabricated implant preferably manufactured from clear sonolucent poly (methyl methacrylate) (PMMA) or any other clear biocompatible material suited for safe use in craniofacial reconstruction. While a clear PMMA static cranial implant 204 of the craniofacial implant 200 is used in accordance with a disclosed embodiment as discussed herein, it is appreciated the prefabricated static cranial implant 204 may further include a polymer, metal, bioengineered material, or any combinations thereof as described above. The static cranial implant 204 is manufactured to allow for the transmission of waves other than optical light waves, in particular, the static cranial implant 204 is sonolucent (that is, allowing passage of ultrasonic waves without production of echoes that are due to reflection of some of the waves). The static cranial implant 204 may also be radiolucent (that is, allowing passage of radio waves without production of echoes that are due to reflection of some of the waves).

As with the prior embodiment, the craniofacial implant 200 may be of the type described in International Patent Application PCT/US2016/030447, filed May 2, 2017, entitled "LOW PROFILE INTERCRANIAL DEVICE" (published as WO 2017/039762), U.S. patent application Ser. No. 15/669,268, filed Aug. 4, 2017, entitled "METHOD FOR MANUFACTURING A LOW-PROFILE INTERCRANIAL DEVICE AND THE LOW-PROFILE INTERCRANIAL DEVICE MANUFACTURED THEREBY" (published as U.S. Patent Application Publication No. 2018/0055640), and U.S. patent application Ser. No. 16/203,357, filed Nov. 28, 2018, entitled "UNIVERSAL LOW-PROFILE INTERCRANIAL ASSEMBLY" (published as U.S. Patent Application Publication No. 2019/0209328), all of which are incorporated herein by reference.

As with the prior embodiment, the embodiment disclosed with reference to FIGS. 4, 5, and 6, the craniofacial implant 200 is a universal low-profile intercranial assembly. The universal low-profile intercranial assembly 200 is generally composed of mounting plate 202 into which a low profile intercranial device 203 composed of a static cranial implant 204 and a functional neurosurgical implant 206 are mounted. This combination of elements results in the universal low-profile intercranial assembly 200 that provides a mechanism whereby various low profile intercranial devices 203 may be implanted as desired and needed based upon the progress of a patient undergoing cranial and/or brain-based treatments.

The mounting plate 202 includes a hollowed-out center aperture 208 shaped and dimensioned for the ready placement and mounting of the low profile intercranial device 203 therein. The mounting plate 202 is specifically shaped and dimensioned for intercranial placement within the cranial defect while simultaneously providing a center aperture 208 into which a low profile intercranial device 203 may be readily mounted. Given that the center aperture 208 of the mounting plate 202 is of a known shape, which may be readily replicated and controlled, the shape of the low profile intercranial device 203 can be readily controlled to allow for immediate and exact placement of the low profile intercranial device 203 within the center aperture 208. This allows for a first low profile intercranial device 203 to be implanted and used at a first stage of a patient's treatment and subsequently removed and replaced with a second low profile intercranial device at a second stage of the patient's treatment.

The mounting plate 202 includes an outer (commonly convex) first surface 202*o*, an inner (commonly concave) second surface 202*i*, and a peripheral edge 202*p* extending between the outer first surface 202*o* and the inner second surface 202*i*. The mounting plate 202 is shaped and dimensioned for engagement with the skull of the patient upon implantation in a manner well known to those skilled in the field of neurosurgical procedures. The outer first surface 202*o* and inner second surface 202*i* of the mounting plate 202 are preferably curved in a superior to inferior direction, a posterior to anterior direction, and a medial to lateral direction. In addition, the peripheral edge 202*p* has a substantial taper for resting upon a matching taper formed along the skull. It is, however, appreciated that this taper may vary (or not exist at all, that is, the peripheral edge 202*p* may be substantially perpendicular relative to the outer first surface 202*o* and the inner second surface 202*i*) depending upon the specific needs of the procedure. In accordance with a preferred embodiment, the mounting plate 202 will have a preselected thickness not exceeding the space between the inner surface of the scalp and the outer surface of the dura, for example, in the range of around 1 millimeter to 25 millimeters (with areas of strategic bulking and/or thinning) and depending upon the strength of the materials used in the construction of the mounting plate 202. Preferably, the mounting plate 202 will have a thickness of 1 millimeter to 12 millimeters. As mentioned above, the mounting plate 202 also includes a center aperture 208 designed to accommodate the static cranial implant 204. The center aperture 208 is defined by an inner wall 210 extending between outer first surface 202*o* and inner second surface 202*i* of the mounting plate 202.

The static cranial implant 204 has a two-piece construction allowing for ready access to the functional neurosurgical implant 206 without the need for complete removal of the low-profile intercranial device. The two-piece static cranial implant 204 includes a base cranial implant member 212 and a cover cranial implant member 214. The base cranial implant member 212 has a geometry that substantially conforms to a resected portion of the patient's anatomy to which the low-profile intercranial device is to be secured. The base cranial implant member 212 includes an outer (commonly convex) first surface 212*o*, an inner (commonly concave) second surface 212*i*, and a peripheral edge 212*p* extending between the outer first surface 212*o* and the inner second surface 212*i*. The outer first surface 212*o* and inner second surface 212*i* of the base cranial implant member 212 are preferably curved in a superior to inferior direction, a posterior to anterior direction, and a medial to lateral direction.

The base cranial implant member 212 also includes a center recess 216 formed along the outer first surface 212*o* and optional structural elements, for example, tunnels, channels, pockets, access holes, and/or other structural elements, designed to accommodate various features of the functional neurosurgical implant 206.

In addition to the base cranial implant member 212, the two-piece static cranial implant 204 includes a cover cranial implant member 214. The cover cranial implant member 214 is shaped and dimensioned for positioning over the center recess 216 along the outer first surface 212*o* of the base cranial implant member 212. In accordance with a preferred embodiment, the cover cranial implant member 214 is secured to the base cranial implant member 212 by screw fixation. The cover cranial implant member 214 includes an outer (commonly convex) first surface 214*o*, an inner (commonly concave) second surface 214*i*, and a peripheral edge 214*p* shaped and dimensioned for engagement with the outer first surface 212*o* of the base cranial implant member 212 along the periphery of the center recess 216. As with the base cranial implant member 212, the outer first surface 214*o* and inner second surface 214*i* of the cover cranial implant member 214 are preferably curved in a superior to inferior direction, a posterior to anterior direction, and a medial to lateral direction.

The base cranial implant member 212 and the cover cranial implant member 214 have a total thickness similar to that of the embodiment described above, that is, and depending on the strength characteristics of the materials used, the base cranial implant member 212 and the cover cranial implant member 214 will have a thickness (with areas of strategic bulking and/or thinning) of around 1 millimeter to 25 millimeters, preferably, 1 millimeter to 12 millimeters.

The cover cranial implant member 214 fits over the center recess 216 along the outer first surface 212*o* of the base cranial implant member 212. In this way, the inner second surface 214*i* of the cover cranial implant member 214 and the outer first surface 212*o* of the base cranial implant member 212, along the center recess 216, define a center cavity 218 configured to conform to the exact requirements of the functional neurosurgical implant 206 in accordance with the present invention. With this in mind, the inner second surface 214*i* of the cover cranial implant member 214 may be shaped and/or contoured to enhance the positioning of the functional neurosurgical implant 206 within the center cavity 118.

As will be appreciated based upon the various embodiments disclosed herein, the functional neurosurgical implant 206 of the present invention is selected from a variety of FDA-approved and experimental options for electrical, optical, mechanical, medicinal, and other treatment/monitoring devices designed for long term invasive treatment and/or disease-monitoring of patients requiring such attention. These functional neurosurgical implants are known devices manufactured by various vendors within the neurosurgical industry and have known, unmodifiable dimensions that may be used in the modification of the static cranial implant 204 to optimize surgical results by minimizing abnormal shapes, visible contours, and/or craniofacial deformities.

In accordance with this embodiment, the functional neurosurgical implant 206 may be a battery-powered functional neurosurgical implant known as the NeuroPace® device, an ultrasound reading would be achieved through the use of a traditional ultrasound transducer taking images through the static cranial implant 204. Additional functional neurosurgical implants as discussed above may be used in conjunction with the present invention.

Figure 7:
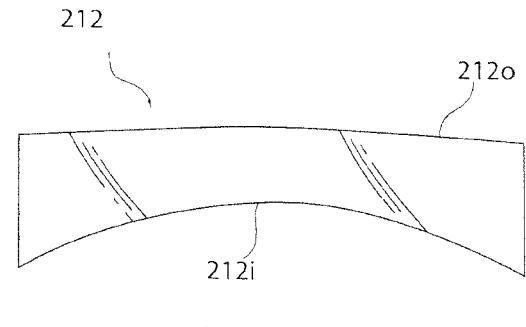
FIG. 7 shows a side view of a base cranial implant member with differing curvatures along the inner second surface and the outer first surface.

Use of the handheld ultrasound transducer 231 in conjunction with the static cranial implant 204 and functional neurosurgical implant 206 of this embodiment is enhanced by the integration of alignment mechanisms in the static cranial implant. In particular, and with reference to FIG. 7, the static cranial implant may be constructed with variations in shape designed to control the manner in which light, sound, radio, and other waves pass therethrough, that is, lensing or the focusing of light, sound, radio, and other waves by adjusting the thickness and/or curvature of the cranial implant. Such variations in shape would be undertaken in a manner similar to the way in which eyeglasses are adjusted for each patient. For example, and with reference to the disclosed embodiment shown in FIG. 7, the curvature of the outer first surface 212*o* of the base cranial implant member 212 differs from the curvature of the inner second surface 212*i* of the base cranial implant member 212 wherein the outer first surface 212*o* has a much larger radius of curvature. It is also appreciated that in addition to focusing light, sound, radio, and other waves, adjustments to the thickness and/or curvature of the cranial implant may also be used to enhance signal to noise ratio, contrast to noise ratio, and/or minimization or maximization of thermal spread relative to a target.

Figure 8:
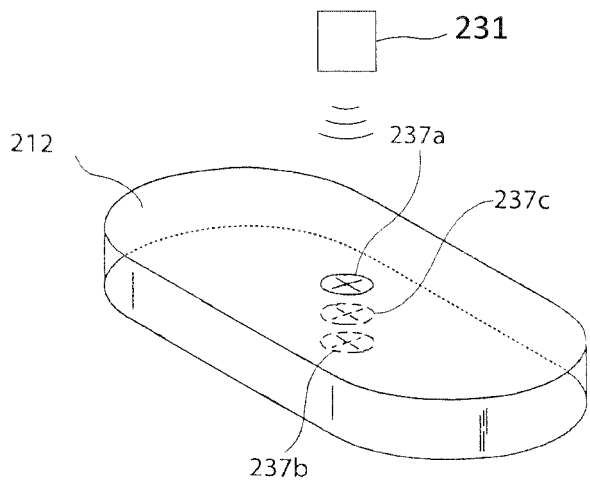
FIG. 8 shows a base cranial implant member with an alignment feature.

In accordance with another embodiment as shown with reference to FIG. 8, the static cranial implant may be constructed with an alignment feature. In accordance with a disclosed embodiment, the alignment feature includes a series of markings at different depths within the base cranial implant member 212 of the static cranial implant 204. For example, an outer first static cranial implant marking 237*a* and an inner second static cranial implant marking 237*b* are formed along the outer first surface 212*o* and the inner second surface 212*i*, respectively, of the base cranial implant member 212 of the static cranial implant 204. One or more additional interior static cranial implant markings 237*c* may be formed within the body of the base cranial implant member 212 of the static cranial implant 204 and in alignment with the outer first static cranial implant marking 237*a* and the inner second static cranial implant marking 237*b*. While an outer first static cranial implant marking 237*a*, an inner second static cranial implant marking 237*b*, and at least one additional interior static cranial implant marking 237*c* are disclosed herein, it is appreciated various combinations of markings may be used within the spirit of the present invention.

The outer first static cranial implant marking 237*a*, the inner second static cranial implant marking 237*b*, and the plurality of additional interior static cranial implant markings 237*c* are aligned such that when the ultrasound transducer 231 is properly aligned with the markings 237*a-c*, the ultrasound waves will be directed to the proper location within the cranium. Similarly, when one looks through the static cranial implant 204 and the outer first static cranial implant marking 237*a*, the inner second static cranial implant marking 237*b*, and the at least one additional interior static cranial implant marking 237*c* merge into a single location identifying image (for example, crosshairs or circles), a specific brain anatomy (or other structural element upon the surface of the brain) is identified by the single location identifying image. When the specific brain anatomy identified by the single location identifying image changes over time, the surgeon will know that something has shifted and will take appropriate action.

Figure 9:
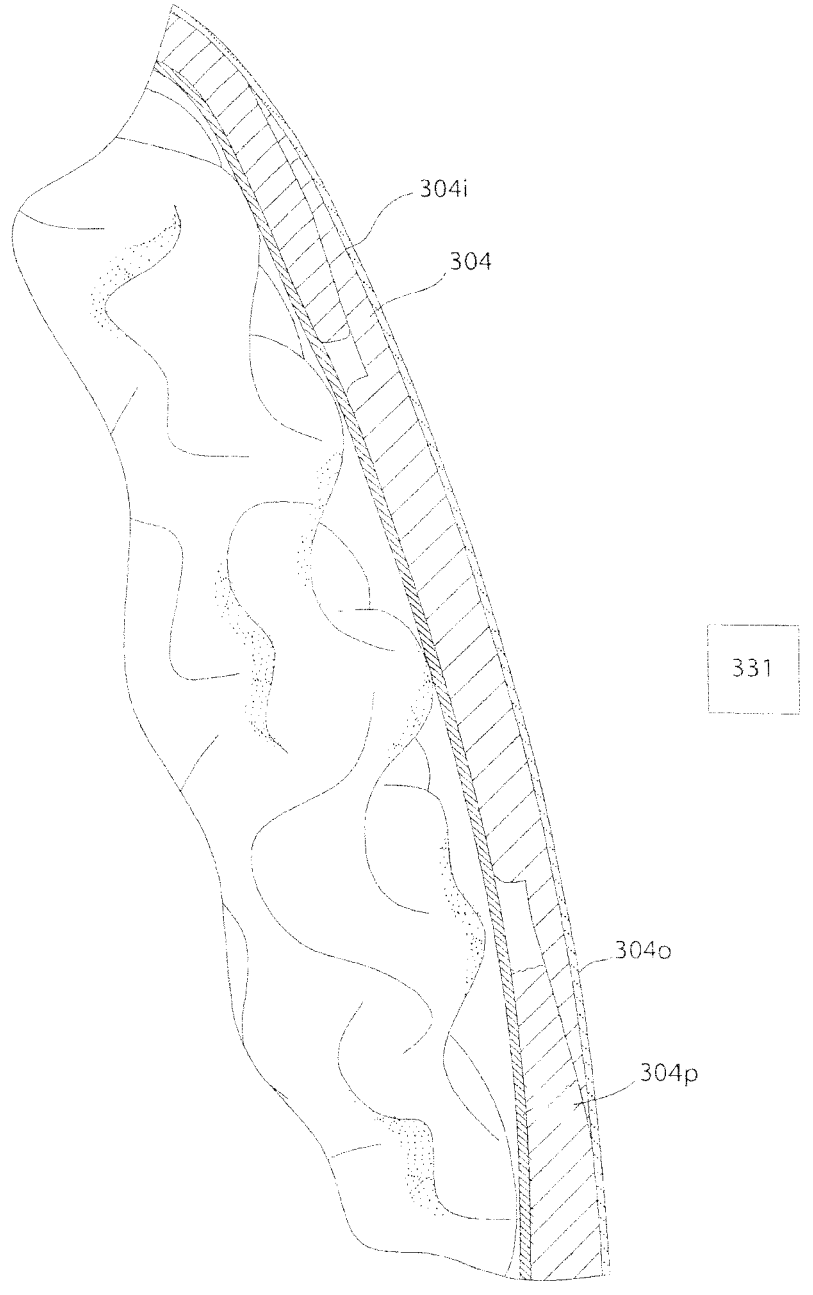
FIG. 9 is a cross section view of a craniofacial implant in accordance with a third embodiment.

As shown with reference to FIG. 9, the invention may be practiced where a handheld ultrasound transducer 331 is used, and the sonolucent craniofacial implant is only composed of a sonolucent static cranial implant 304 and does not include a functional neurosurgical implant or a mounting plate. In accordance with such an embodiment, the static cranial implant 304 exhibits desirably sonolucent characteristics allowing for the handheld ultrasound transducer 331 to function properly. The static cranial implant 304 also preferably includes the alignment markings discussed above with respect to FIG. 8.

As with the prior embodiment, the static cranial implant 304 is a prefabricated implant manufactured from clear sonolucent poly (methyl methacrylate) (PMMA) or any other clear biocompatible material suited for safe use in craniofacial reconstruction. While clear sonolucent PMMA is disclosed in accordance with a preferred embodiment, it is appreciated other materials, for example, clear sonolucent PEEK, may be used. The static cranial implant 304 may also be radiolucent (that is, allowing passage of radio waves without production of echoes that are due to reflection of some of the waves).

As with the prior embodiment, the clear static cranial implant 304 may be manufactured in a manner allowing for the transmission of ultrasonic waves as described in U.S. Pat. No. 9,044,195, entitled "IMPLANTABLE SONIC WINDOW" ('195 patent), which is incorporated herein by reference. In addition, U.S. Pat. No. 9,535,192, entitled "METHOD OF MAKING WAVEGUIDE-LIKE STRUCTURES" ('192 Publication), and U.S. Patent Application Publication No. 2017/0156596, entitled "CRANIAL IMPLANTS FOR LASER IMAGING AND THERAPY" ('596 Publication), both of which are incorporated herein by reference, disclose making waveguide-like structures within optically transparent materials using femtosecond laser pulses wherein the optically transparent materials are expressly used in the manufacture of cranial implants. Further still, Tobias et al. describe an ultrasound window to perform scanned, focused ultrasound hyperthermia treatments of brain tumors. Tobias et al., "ULTRASOUND WINDOW TO PERFORM SCANNED, FOCUSED ULTRASOUND HYPERTHERMIA TREATMENTS OF BRAIN TUMORS," Med. Phys. 14(2), March/April 1987, 228-234, which is incorporated herein by reference. Further still, Fuller et al., "REAL TIME IMAGING WITH THE SONIC WINDOW: A POCKET-SIZED, C-SCAN, MEDICAL ULTRASOUND DEVICE," IEEE International Ultrasonics Symposium Proceedings, 2009, 196-199, which is incorporated herein by reference, provides further information regarding sonic windows.

Radiolucency as applied to the present invention allows a clinician to see the anatomy surrounding the static cranial implant 304 without "scatter" or interfering artifacts from the implant for diagnosis and follow-up. As discussed above, radiolucency also allows for the use of radio frequency (RF) therapeutics in conjunction with the craniofacial implant described herein.

The static cranial implant 304 may be of the type described in International Patent Application PCT/US2016/030447, filed May 2, 2017, entitled "LOW PROFILE INTERCRANIAL DEVICE" (published as WO 2017/039762), U.S. patent application Ser. No. 15/669,268, filed Aug. 4, 2017, entitled "METHOD FOR MANUFACTURING A LOW-PROFILE INTERCRANIAL DEVICE AND THE LOW-PROFILE INTERCRANIAL DEVICE MANU- FACTURED THEREBY" (published as U.S. Patent Application Publication No. 2018/0055640), and U.S. patent application Ser. No. 16/203,357, filed Nov. 28, 2018, entitled "UNIVERSAL LOW-PROFILE INTERCRANIAL ASSEMBLY" (published as U.S. Patent Application Publication No. 2019/0209328), all of which are incorporated herein by reference.

The static cranial implant 304 includes an outer (commonly convex) first surface 3040, an inner (commonly concave) second surface 304i, and a peripheral edge 304p extending between the outer first surface 304o and the inner second surface 304i. The static cranial implant 304 is shaped and dimensioned for engagement with the skull of the patient upon implantation in a manner well known to those skilled in the field of neurosurgical procedures.

The static cranial implant 304 has a total thickness similar to that of the embodiment described above, that is, and depending on the strength characteristics of the materials used, the static cranial implant 304 will have a thickness (with areas of strategic bulking and/or thinning) of around 1 millimeter to 25 millimeters, preferably, 1 millimeter to 12 millimeters.

Figure 15:
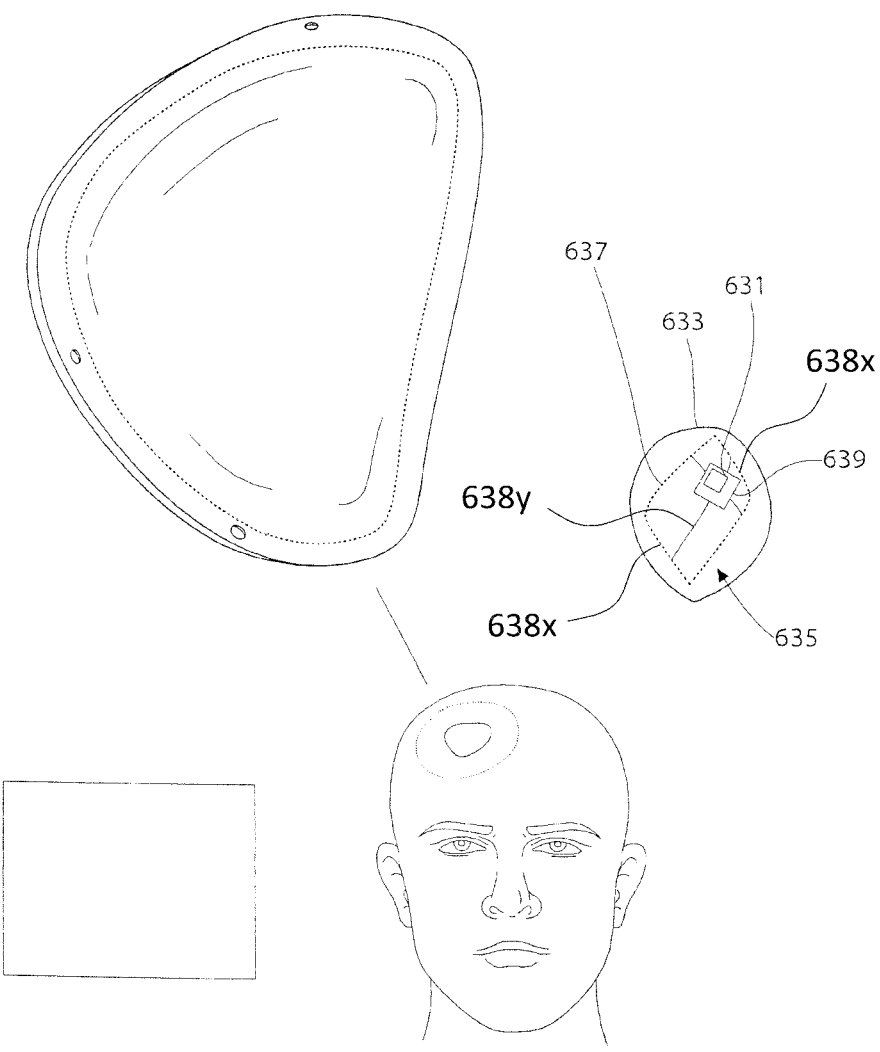
FIG. 15 is an exploded perspective view of a craniofacial implant system in accordance with a sixth embodiment.

Considering the provision of a remote ultrasound transducer that is separate and distinct from the cranial implant, a conventional handheld ultrasound transducer has been previously disclosed. However, and with reference to the embodiment disclosed in FIG. 15, it is contemplated the ultrasound transducer 631 is integrated into a wearable wireless ultrasound transducer (WWUT) 633. The wearable wireless ultrasound transducer 633 is in the form of a cap, hat, helmet, etc., and is constructed such that it may be adjusted. Within the wearable wireless ultrasound transducer 633 is a mechanical system for articulating the ultrasound transducer 631. For example, an adjustable ultrasound system includes an ultrasound transducer 631 and a support assembly 635 providing for movement of the ultrasound transducer 631 in two dimensions, that is, in X and Y, relative to the surface of the cranial implant. The support assembly 635 is an XY gantry 637 with a carriage 639 supporting the ultrasound transducer. The XY gantry 637 include tracks or guides 638x, 638y along which the gantry carriage 639 moves by means of electric motors (not shown) along the various axes to most accurately position the ultrasound transducer 631. Movement of the gantry carriage 639 is controlled by a variety of actuators that move the gantry carriage 639 and the tracks/guides in a controlled manner. In accordance with the disclosed embodiment, parallel guides 638x aligned in the X-direction support a perpendicular guide 638y aligned in the Y direction. The perpendicular guide 638 aligned in the Y direction is mounted upon the parallel guides 638x aligned in the X-direction for linear movement relative thereto. The gantry carriage 639 is mounted upon the perpendicular guide 638y aligned in the Y direction for controlled movement thereon. Through the controlled movement of the perpendicular guide 638y aligned in the Y direction and the gantry carriage 639, the ultrasound transducer 631 is moved in the X and Y planes.

In accordance with another embodiment, the ultrasound transducer may be mounted within slots that provide a track for the ultrasound transducer to move along multiple axes within the wearable wireless ultrasound transducer, for example X, Y, Z axis.

Regardless of the movement system used, proper positioning of the ultrasound transducer is achieved by a feedback system notifying the mechanical adjustment structure that correct position has been achieved.

The preceding discussion presents embodiments wherein the implant is optimized for use in conjunction with various transducers. It is also appreciated a transducer might be fabricated with specific characteristics making it optimally suited for use in conjunction with specific implants.

As briefly discussed above, the provision of a cranial implant that is specifically adapted for use in conjunction with ultrasound opens a variety of applications that are discussed below.

Ultrasound Transducer Optimized for the Implant

An ultrasound transducer, whether it be an ultrasound transducer 106 mounted within the cavity 118 of the static cranial implant 104 as disclosed with reference to FIGS. 1, 2, and 3, or an ultrasound transducer 231, 331, intended to be utilized remote in conjunction with the static cranial implant 204, 304 as disclosed with reference to FIGS. 4, 5, 6, and 9, is optimized for imaging and interacting with the neuro anatomy, specifically the brain. The ultrasound transducer 106, 231, 331 is pre-set to frequencies, gain, field of view, etc. that are optimal for brain imaging.

Because the attenuation of ultrasound signals passing through the cranial implant is known, this information may be used to optimize imaging. For example, and considering a cranial implant composed of clear sonolucent PMMA and having a thickness ranging between 3.0 mm-6.5 mm with a mean thickness of 5.4 mm, the cranial implant exhibits attenuation characteristics resulting in minimal degradation of the ultrasonic waves generated by the transducer of an ultrasound system.

As those skilled in the art will appreciate, the amplitude change of a decaying plane wave can be expressed as:

$$A = A_0 e^{ad}$$

where, $A_0$ is the unattenuated amplitude of the propagating wave

A is the reduced amplitude after the wave has traveled a distance d a is the attenuation constant measured in nepers/length (wherein Np/m may be converted to decibels by dividing a by 0.1151), where a neper is a dimensionless quantity e is the exponential (or Napier's constant) which is equal to approximately 2.71828.

It is further appreciated attenuation of an ultrasonic wave is generally a function of the frequency of the ultrasonic wave and intrinsic properties of the medium. This is used to differentiate PMMA from other implant materials. It is further appreciated that the Attenuation Coefficient as measured in dB/(mHz×cm) represents the intrinsic property of a medium to attenuate ultrasound waves at a given frequency. With the foregoing in mind the cranial implant exhibits attenuation of no more than 6 dB/cm at frequencies between 1 MHz and 9 MHz. Within the range of 2 MHz to 2.5 MHz, the cranial implant exhibits even better (that is, lower) attenuation characteristics. Operation of the ultrasound transducer between 1 MHz and 9 MHz is desired when the ultrasound transducer is used for imaging purposes. However, the ultrasound transducer may be used for therapeutic purposes, as discussed below, when the ultrasound transducer is operated in the range of 150 KHz to 1.2 MHz.

Using this information, the frequency and gain of the ultrasound transducer are varied to achieve various imaging and therapeutic goals. For example, and in accordance with one embodiment, the ultrasound transducer applies a frequency and gain resulting in a wide field of view allowing for the identification of various neural anatomy landmarks. With the landmark information from an initial scan in hand, the ultrasound transducer is operated in doppler ultrasound mode to identify various vascular elements of interest. The image data from the initial scan and the doppler ultrasound scan are then processed and the information is used to develop a generated neural anatomy landscape. With the neural anatomy landscape in hand, the frequency and gain of the ultrasound transducer are adjusted to allow the ultrasound transducer to image highly specific parts of the neural anatomy. In this way, the ultrasound transducer of the present invention is capable of identifying and imaging specific neural anatomy as desired.

For example, and considering an exemplary embodiment for relative deep imaging in the depth range of 9-15 cm, a sector array (or phased array) ultrasound transducer probe is utilized with the abdominal factory preset, a frequency of approximately 1 MHz to approximately 3 MHz, a dynamic range of approximately 55 dB to approximately 65 dB, and a gain of approximately 55 dB to approximately 70 dB. Other parameters that may be varied include time gain compensation, ultrasound Gray Map setting, line density, frame average persistence, edge enhancement, Doppler gain, pulse repetition period (PRF), wall filter, imaging angle, focal zone (wherein a single focus point is to be place at or slightly below the region of interest and this maintains the highest frame rate capability of the system (additional focus zones may be added to improve resolution within a larger region but doing so will decrease the frame rate)), etc.

An additional consideration for use in conjunction with ICP (Intracranial Pressure) monitoring is an advanced feature of ultrasound called "shear wave elastography." Those skilled in the art will appreciate that these parameters are dependent upon the manufacturing characteristics of the specific ultrasound system being used. It is also appreciated that scan parameters will be adjusted to accommodate ambient light.

When selecting an ultrasound system for transcranial imaging various considerations should be taken into account. For example, it is anticipated the following would be the order of good-better-best when deciding upon ultrasound systems for image quality, capability, and functionality: hand-held (phone/tablet); point of care (cart based); radiology (console).

When making determinations regarding the best ultrasound transducer probe for use, a phased array probe is preferred when imaging neuro anatomy while linear array probes and phased array probes are considered optimal for imaging neuro vascular anatomy. In particular, the small footprint (size), low frequency (optimizes penetration for visualization of deeper structures like ventricles and skull base), and beam shape (provides a large field of view from the small footprint probe) make phased array probes an ideal choice for imaging of neuro anatomy. With regard to imaging of neuro vascular, linear array probes are best for EC-IC (Extracranial-Intracranial) bypasses as they are designed for vascular assessment, they are well suited for large areas, the high frequency provides great image quality and optimal frame-rates for shallow vessels, and the beam steering improves doppler shift for better sensitivity to blood flow. With regard to imaging of neuro vasculature, phased (Sector) array probes are best for transcranial doppler of intracranial arteries and where the low frequency penetrates deeper to visualize the Circle of Willis.

A further consideration in the use of ultrasound transducers in accordance with the present invention is the orientation of the ultrasound transducer during imaging. As those skilled in the art will appreciate, a probe orientation marker is a notch or groove on one side of the ultrasound transducer (or probe) which corresponds to the orientation marker on the screen (blue dot generally found on the top left of the image). When imaging neuroanatomy the operator preferably scans in the coronal plane with the blue dot on the ultrasound transducer pointed to the patient's right side. The ultrasound image has a corresponding blue dot to indicate the orientation to the patient's right side. When imaging the neurovascular, the operator preferably scans transverse to image the vessels in cross section. The operator may also turn the ultrasound transducer sagittal to elongate and orient the blue marker in the direction of flow.

Ideally, a first ultrasound is taken 12-24 hours post procedure (allows air to reabsorb). Follow up ultrasounds need to be aware of the uneven skin surface caused by stapling and suturing for closure. This is solved by using extra ultrasound gel to displace the air between the ultrasound transducer and skin surface to provide the sound beam a direct path and eliminate air artifacts. Early research suggests topical hemostatic agents, collagen-based overlays (i.e., Tachosil® and some dural substitutes (i.e. DuraMatrix®) may interfere with ultrasound penetration and should therefore be considered and/or avoided. Presets and protocols are designed to optimize image quality but serve as a starting point. Other variables like room brightness and patient age may require further adjustments.

Further still artifacts in images may be used advantageously. For example, shadows (due to the fact that ultrasound does not penetrate through air or bone) can be avoided by using more gel and repositioning the ultrasound transducer. As to reverberation, which is repeating lines in an ultrasound that show up deeper to a structure (for example, a catheter), these can help find a shunt/catheter placed in a ventricle.

Considering an exemplary embodiment for more superficial imaging in the depth range of approximately 3 cm, a linear transducer probe is utilized with the "vascular access" or "upper extremity vascular" factory preset, at a frequency of approximately 12 MHz to approximately 15 MHz. As with the prior embodiment, parameters may be varied depending upon the manufacturing characteristics of the specific ultrasound system being used.

In accordance with another embodiment for imaging neuroanatomy with a console, the operator selects "Abdominal" Preset, which is ideal for penetration and soft tissue differentiation, and then edits parameters as desired. The depth is approximately 12-16 cm, which provides a full field of view to the skull base and may be adjusted to focus on anatomy of interest. The gain is set between 55-70%, wherein image brightness will vary with ambient light and the gain may be adjusted as desired to optimize the image.

In accordance with another embodiment for imaging neurovascular systems (EC-IC bypass) using a linear probe with a console, the system preset is set to select "Carotid," which is usually found under vascular; the depth is set to 3-4 cm (adjusted as needed); and the gain is 55-75% (adjusted as needed). Color doppler is applied by activating "Color" doppler" MODE, adjusting color box SIZE from the touchscreen or console, "STEER" color box left/right with the general principle of positioning the bottom of the box in the direction of the deepest part of the vessel, adjusting color "SCALE" so color fills inside the vessel, and adjusting "Color Gain" (60-80%) when COLOR is activated (wherein the general principle is to increase to see color speckles then scale back slightly until speckles are gone).

In accordance with another embodiment for imaging with a console through a sonolucent cranial implant using a phased array probe the following procedures are employed. The General B-Mode Setting is applied by presetting with the selection of "TCD" (Transcranial Doppler) or "Carotid," selecting a depth of 8-10 cm (adjust as needed), and setting the gain at 60-80% (adjust as needed). The Doppler Settings are established by activating "Color" doppler MODE and adjusting as above, activating "PW" (Pulse Wave) doppler" MODE, placing PW "sample gate" on the vessel and location of interest to capture velocities in this precise sampling area (Press PW again to activate spectral tracing), and adjusting spectral scale, gain, and baseline to optimize graph.

In accordance with another embodiment for imaging neurovascular considerations with a console, the operator begins scanning the STA (Superficial Temporal Artery) in transverse anterior to the ear and follows it distally. A doppler shift will only occur if motion is detected travelling TO or AWAY from the probe. The probe may be slightly tilted to create a slight angle which will enhance the doppler shift and improves the doppler color. Longitudinal scans are improved by adjusting the bottom of the color box and steering it toward the deepest part of the vessel. Doppler settings need adjustment to optimize visualization.

In accordance with another embodiment for imaging neuroanatomy with a handheld probe, the operator selects "Abdominal" preset, which is ideal for penetration and soft tissue differentiation, and edits parameters as desired. The depth is approximately 14-16 cm, which is adjusted to see anatomy of interest by moving a finger up & down on the screen to make adjustments. The gain is set between 70-80%, wherein image brightness will vary with ambient light and the gain may be adjusted by moving a finger left and right on the screen as desired to adjust the image.

In accordance with another embodiment for imaging neurovascular systems (EC-IC bypass) using a linear probe with a handheld probe, the system preset is set to select "Vascular Deep Vein,"; the depth is set to 3-4 cm (adjusted as needed by moving a finger up/down on the screen); and the gain is 70-80% (adjusted as needed by moving a finger up/down on the screen). Color doppler is applied by selecting "Actions" then "Color Doppler" under Modes; placing a finger in color box and moving as needed; color box size and "Steering" are adjusted by touching markers on the side and the bottom of the ox (the general principle is to steer the box left/right and position the bottom of the color box in the direction of the deepest part of the vessel); the color gain is set to 70-80% and when COLOR is activated, a finger is moved left/right across screen to adjust the color gain (the general principle is to increase the gain to see color speckles then scale slightly until gone); and the flow speed is left on the default "HIGH" flow setting.

In accordance with another embodiment for imaging with a handheld probe through a sonolucent cranial implant using a phased array probe the following procedures are employed. The General B-Mode Setting is applied by presetting with the selection of "Vascular:Carotid," selecting a depth of 6 cm max allowable with pulsed wave doppler, and setting the gain at 70-80% (adjust as needed by moving a finger left/right on the screen). The Doppler Settings are established by activating "Actions" then "Pulsed Doppler"; using a finger to place a sample volume in a vessel and aligning the arrow to be parallel with vessel walls; pressing "Start Spectrum" on the upper left of the image to start the spectral trace and selecting "Update B-mode" to refresh the image and realign to the best doppler location.

In accordance with another embodiment for imaging neurovascular considerations with a handheld probe, the operator begins scanning the STA transverse anterior to the ear and follows it distally. A doppler shift will only occur if motion is detected travelling TO or AWAY from the probe. The operator may consider tilting the probe to create a slight angle which will enhance the doppler shift and improves the doppler color. Longitudinal scans are improved by touching the bottom of the color box and steering it toward the deepest part of the vessel. Doppler settings need adjustment to optimize visualization.

In accordance with another embodiment for imaging neuroanatomy with a point of care probe, the operator selects "Abdominal" Preset, which is ideal for penetration and soft tissue differentiation, and then edits parameters as desired. The depth is approximately 12-16 cm, which provides a full field of view to the skull base and is adjusted to see anatomy of interest. The gain is set between 55-70%, wherein image brightness will vary with ambient light and the gain may be adjusted.

In accordance with another embodiment for imaging neurovascular systems (EC-IC bypass) using a linear probe with a point of care probe, the system preset is set to select "Carotid," which is usually found under vascular; the depth is set to 3-4 cm (adjusted as needed); and the gain is 55-75% (adjusted as needed). Color doppler is applied by activating "Color doppler" MODE; adjusting color box SIZE from the touchscreen or console; "STEER" color box left/right with the general principle of positioning the bottom of the box in the direction of the deepest part of the vessel; adjusting color "SCALE" so color fills inside the vessel; and adjusting "Color Gain" (60-80%) when COLOR is activated. The general principle is to increase gain to see color speckles then scale back slightly until speckles are gone.

In accordance with another embodiment for imaging with a point of care probe through a clear sonolucent cranial implant using a phased array probe the following procedures are employed. The General B-Mode Setting is applied by presetting with the selection of "TCD" (Transcranial Doppler) or "Carotid", selecting a depth of 8-10 cm (adjust as needed), and setting the gain at 60-80% (adjust as needed). The Doppler Settings are established by activating "Color" doppler MODE and adjusting as above, activating "PW" (Pulse Wave) doppler" MODE, placing PW "sample gate" on the vessel and location of interest to capture velocities in this precise sampling area (Press PW again to activate spectral tracing), and adjusting spectral scale, gain, and baseline to optimize graph.

In accordance with another embodiment for imaging neurovascular considerations with a point of care probe, the operator begins scanning the STA in transverse anterior to the ear and follow it distally. A doppler shift will only occur if motion is detected travelling TO or AWAY from the probe. The operator may consider tilting the probe to create a slight angle which will enhance the doppler shift and improves the doppler color. Longitudinal scans are improved by touching the bottom of the color box and steering it toward the deepest part of the vessel. Doppler settings need adjustment to optimize visualization.

Figure 10:
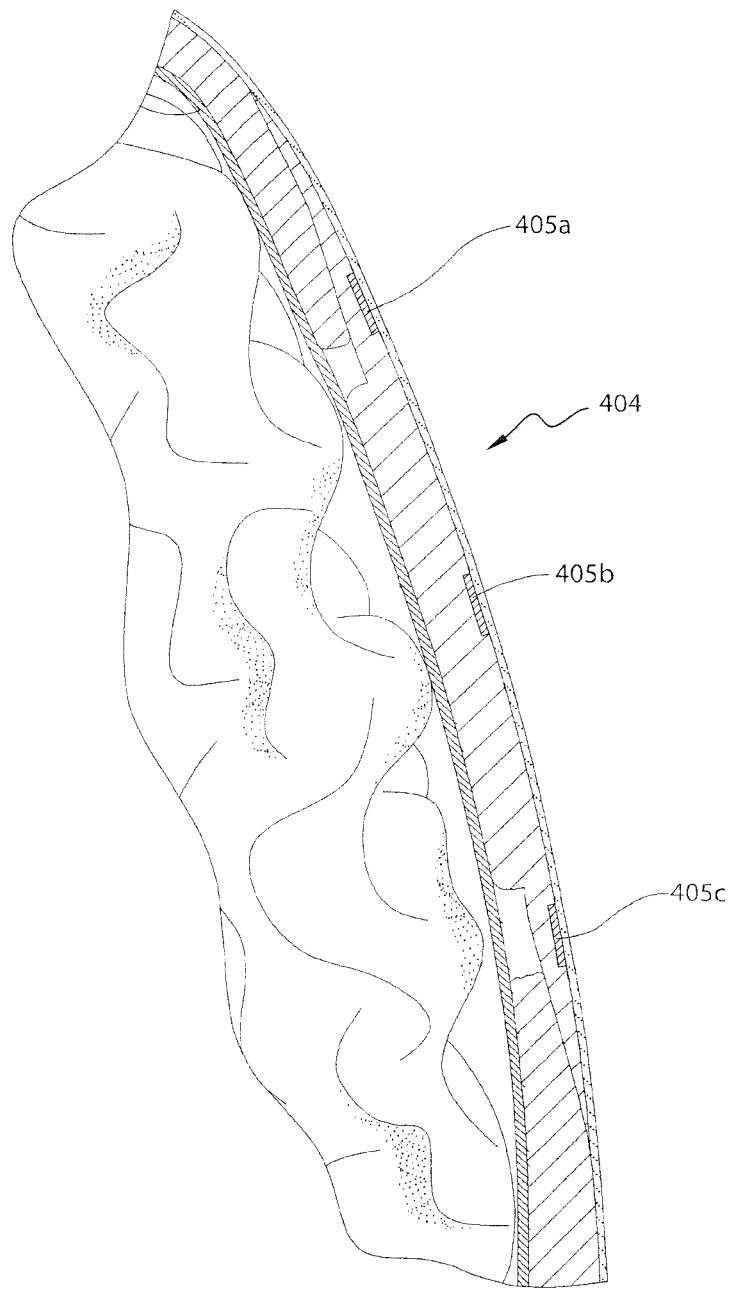
FIG. 10 is a cross section view of a craniofacial implant in accordance with a fourth embodiment.
Figure 11:
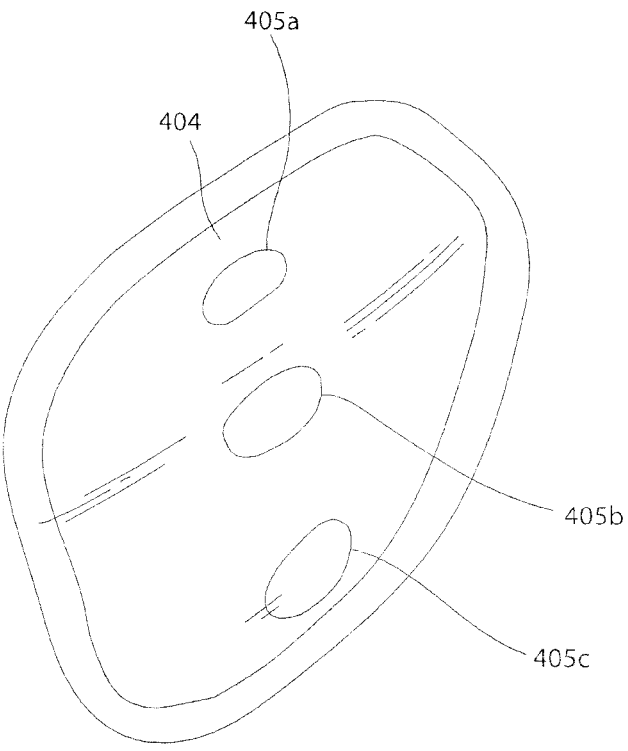
FIG. 11 is a perspective view of the craniofacial implant shown in FIG. 10.

Considering the application of such technology to an ultrasound transducer intended to be utilized remote in conjunction with the sonolucent cranial implant, in addition to the ability to automatically adjust the frequency and gain of the ultrasound transducer, the sonolucent cranial implant 404 is further provided with predefined locations 405*a-c* (for example, identified by tactile, visual, or image based identifiers) for positioning of the ultrasound transducer as shown in FIGS. 10 and 11. This assists in gathering the necessary image data that then may be processed for patient diagnosis and treatment.

Applications for Use of Ultrasound in Conjunction With Cranial Implants

Whether the embodiments disclosed with reference to FIGS. 1 to 3 and 12 to 14, where the ultrasound transducer is integrated with the sonolucent static cranial implant, are used or the embodiments disclosed with reference to FIGS. 4 to 11 where the ultrasound transducer is separate and distinct from the sonolucent static cranial implant, are used, the ultrasound transducer is optimized with or without the use of contrast agents to measure cerebral blood flow, measure intracranial pressure, identify tumors (or their resection plane), and measure ventricles. The ultrasound transducer may also be optimized for non-imaging ultrasound functions such as dilating the BBB (Blood Brain Barrier), stimulating the brain (aka Deep Brain Stimulation), or ablating/cavitating brain tissue. The following description references figures wherein a simplified sonolucent static cranial implant is directly secured to the skull and a separate and distinct ultrasound transducer is used, although it is appreciated embodiments with a mounting plate such as disclosed above could be used. Further, and where the ultrasound transducer is not explicitly disclosed with reference to the application, "US" is used in the drawings to designate the application of ultrasound.

Contrast Agents

Figure 21:
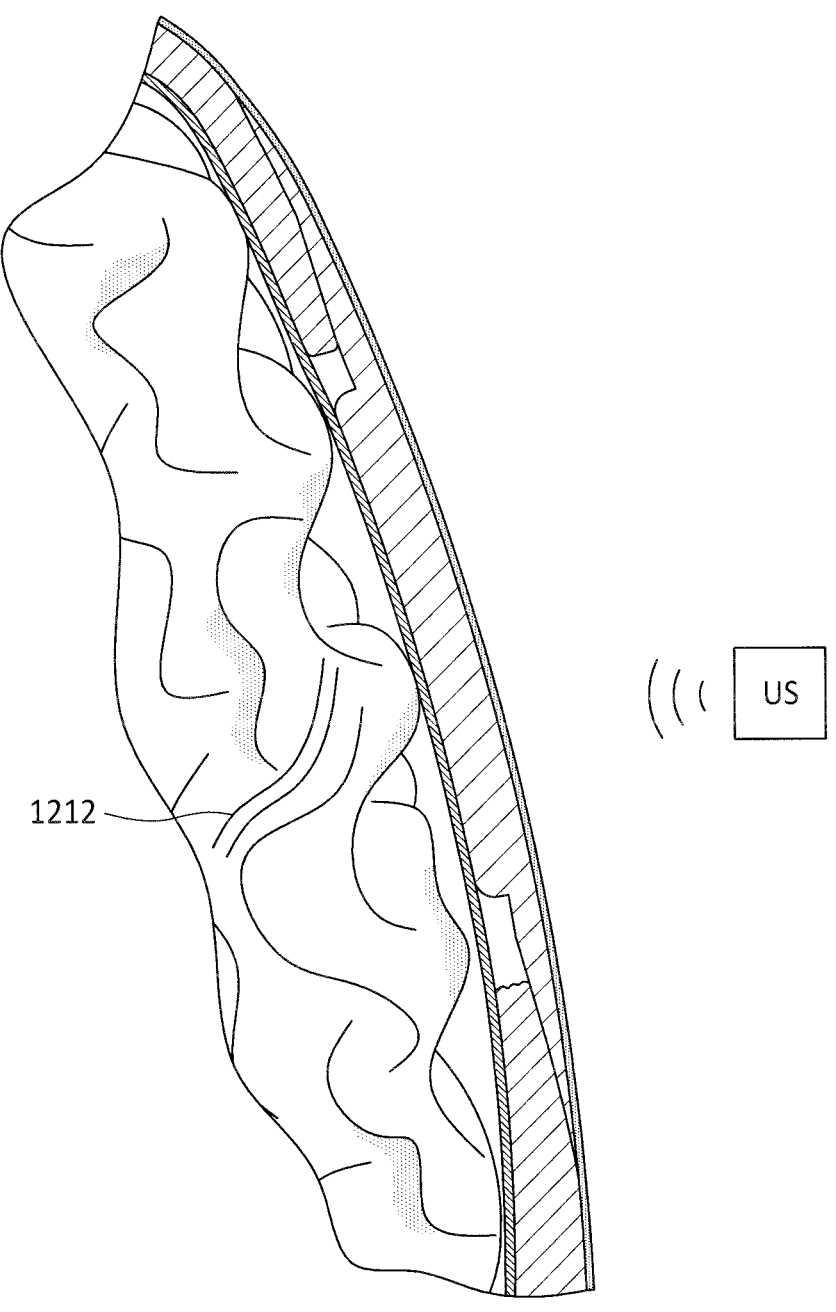
FIGS. 21, 22, 23, 24, and 25 disclose various embodiments where ultrasound is used in association with contrast agents.
Figure 22:
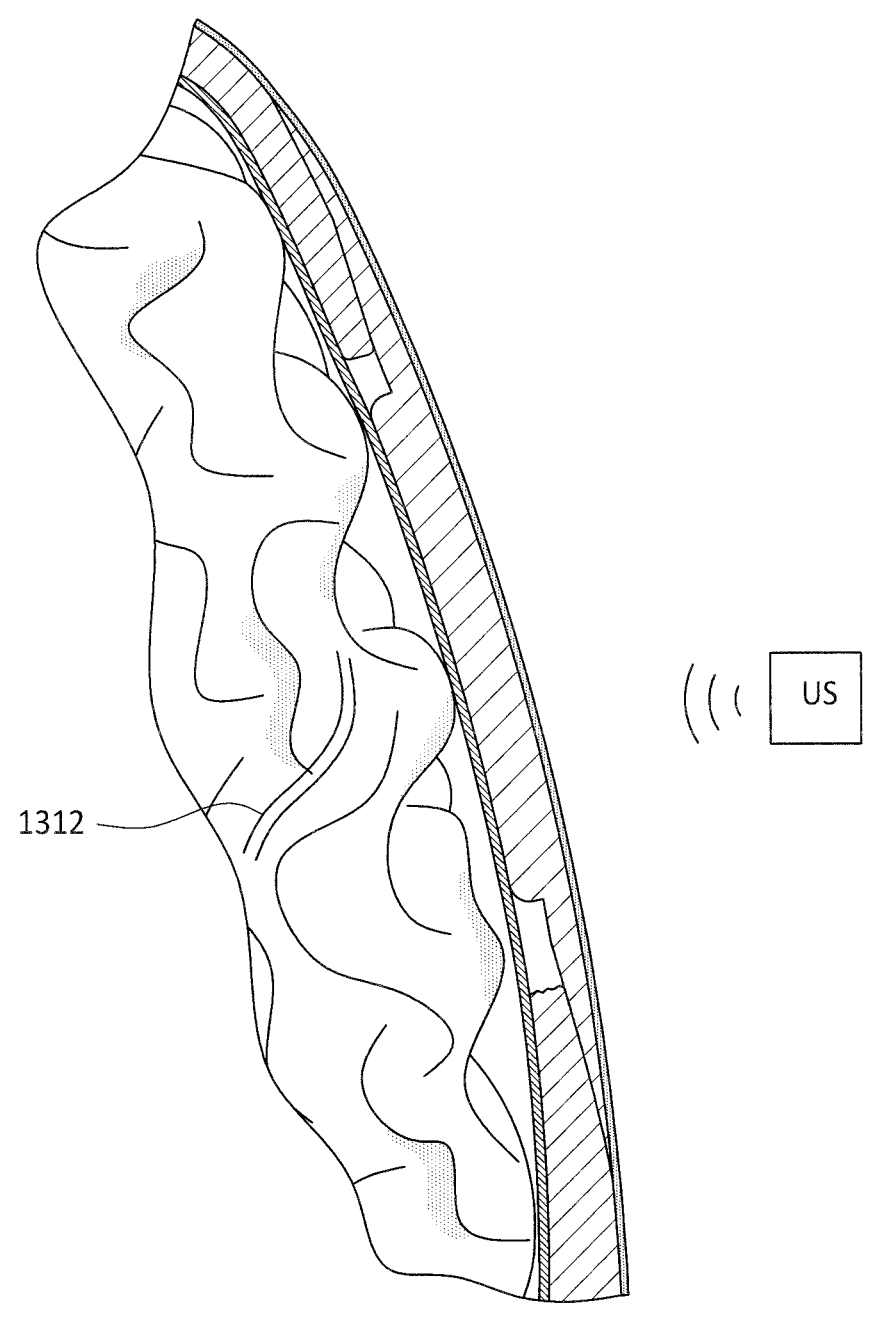
Figure 23:
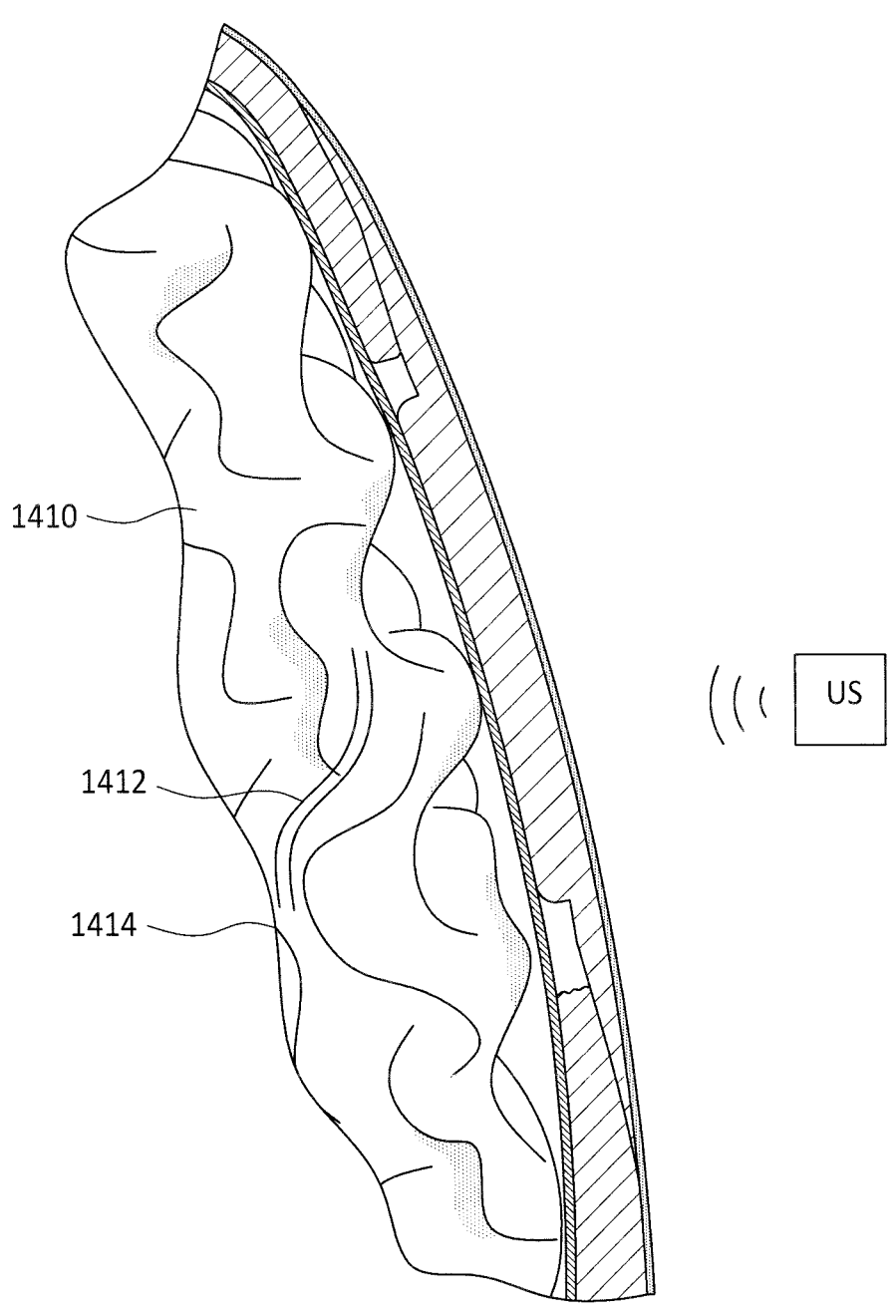
Figure 24:
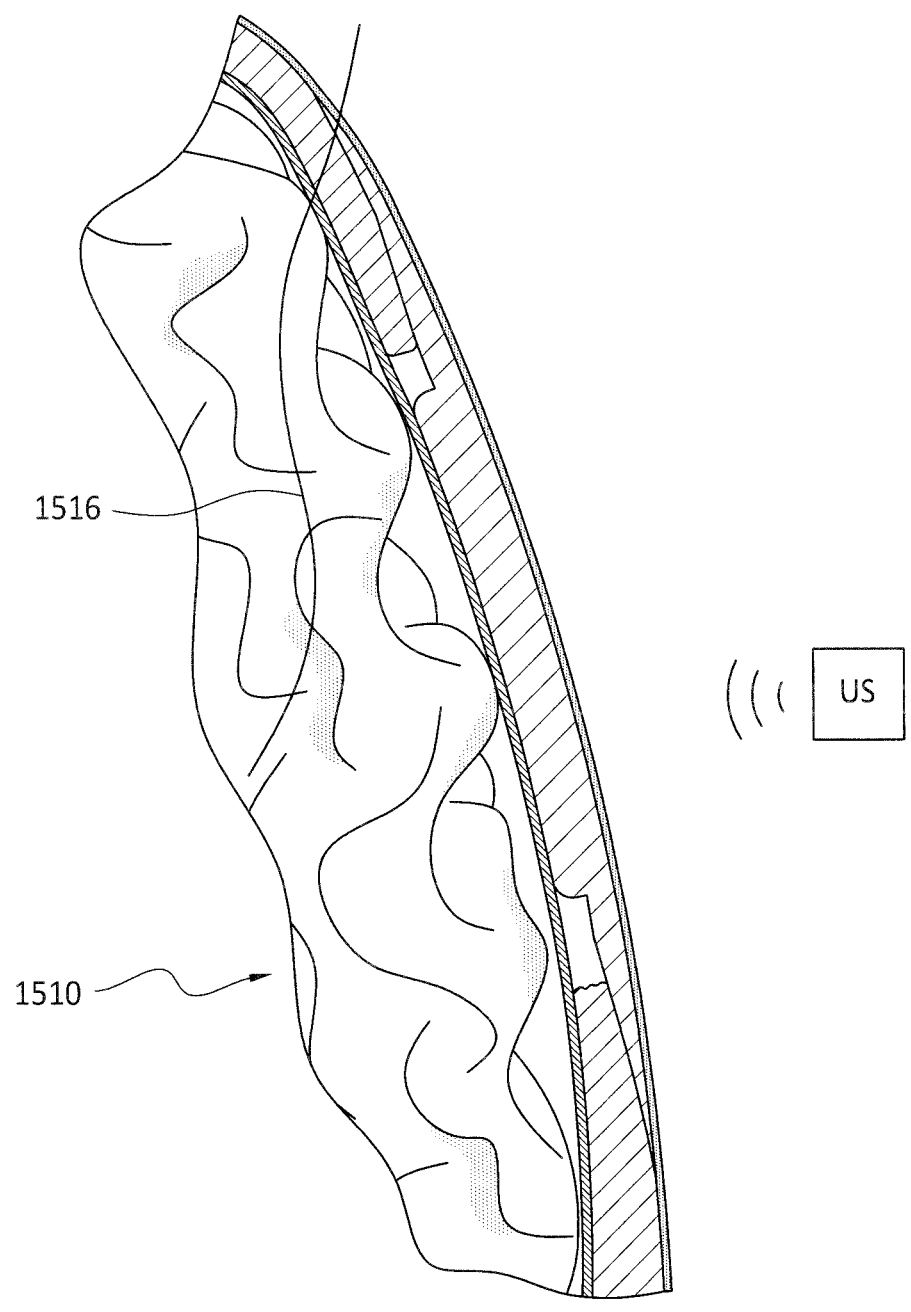
Figure 25:
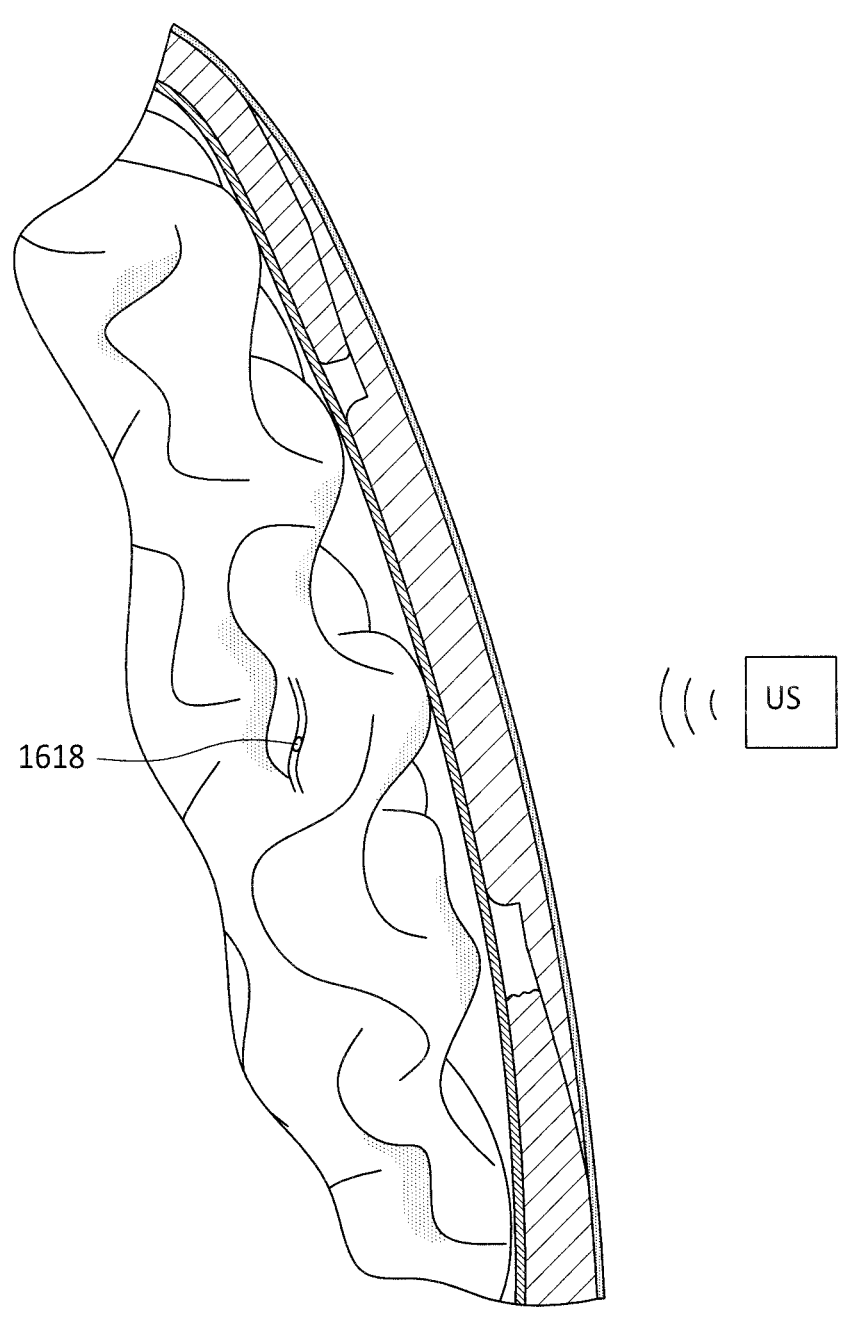

Considering the implementation of the ultrasound transducer (either an implanted ultrasound transducer or an external ultrasound transducer such as a handheld transducer used to image through the sonolucent static cranial implant) in conjunction with contrast agents, the utilization of ultrasound with a sonolucent cranial implant allows one to act upon and/or monitor a contrast agent as it travels within the brain. This allows for various applications, including, but not limited to, imaging confirmation of blood flow 1212 immediately after surgery (see FIG. 21), imaging confirmation of blood flow 1312 during follow-up examinations (see FIG. 22), imaging confirmation of blood flow 1412 to desired locations 1414 within the brain 1410 (see FIG. 23), imaging visualization of, and guidance during, interventional procedures to guide a wire and/or catheter 1516 through the neurovasculature to a desired location in the brain 1510, and to provide an image while a procedure is performed through the catheter 1516, for example, placing a coil within the brain 1510 to treat aneurysms (Such interventional procedures may occur subsequent to an initial procedure including the implantation of the sonolucent cranial implant to fill a defect created in connection with a procedure performed through the defect or the sonolucent cranial implant may be implanted solely for the purpose of supporting visualization during such endovascular interventional procedures) (see FIG. 24), activation of a contrast agent 1618 as it passes a particular point of interest and is subjected to ultrasound for activation thereof, for example, where the contrast agents 1618 are in the form of microbubbles (see FIG. 25), and imaging of microbubble contrast agent during follow-up examinations to examine microbubble diameters and correlatory changes in inter-cranial pressure.

Drug Delivery

Figure 26:
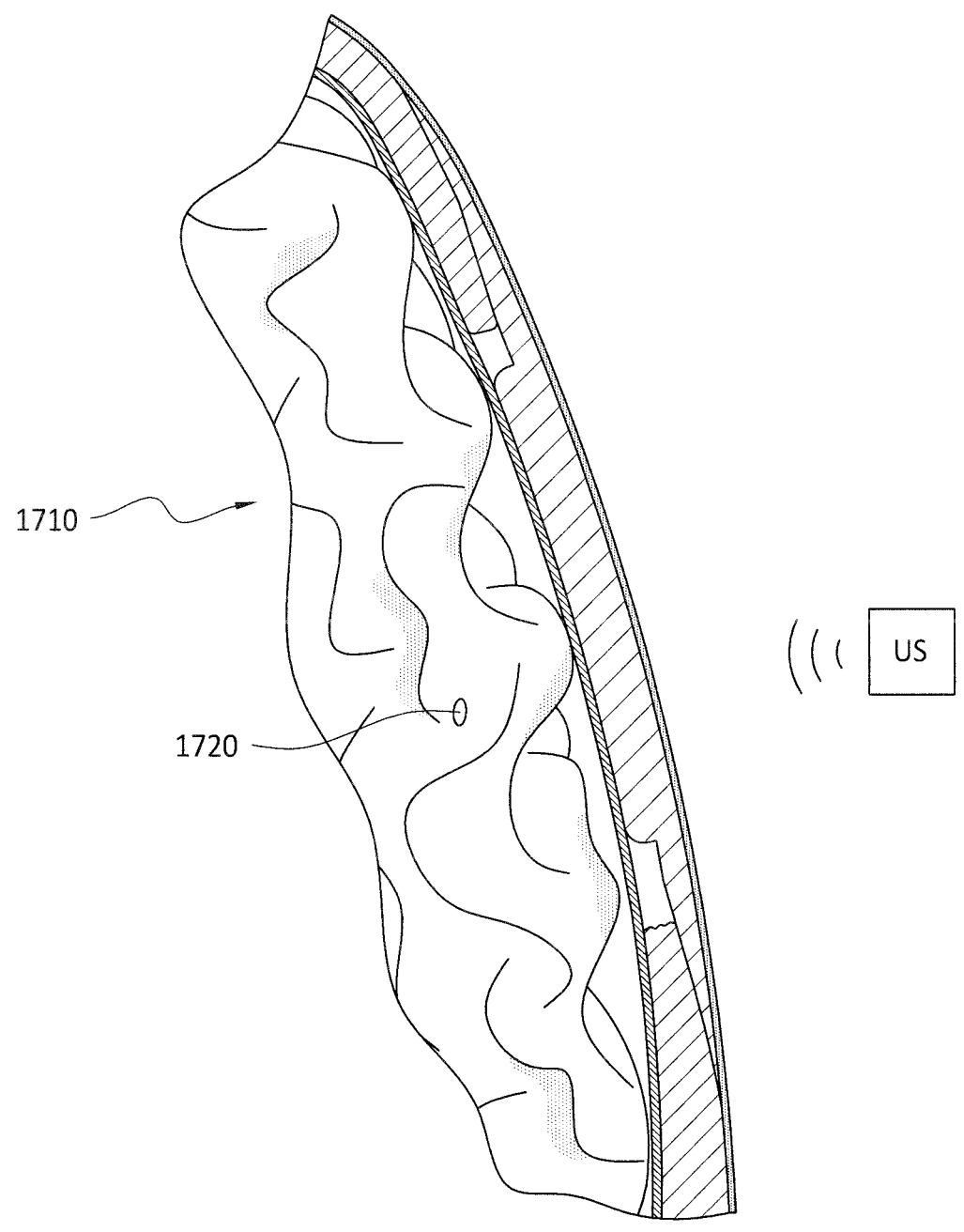
FIGS. 26, 27, and 28 disclose various embodiments where ultrasound is used in association with drug delivery.
Figure 27:
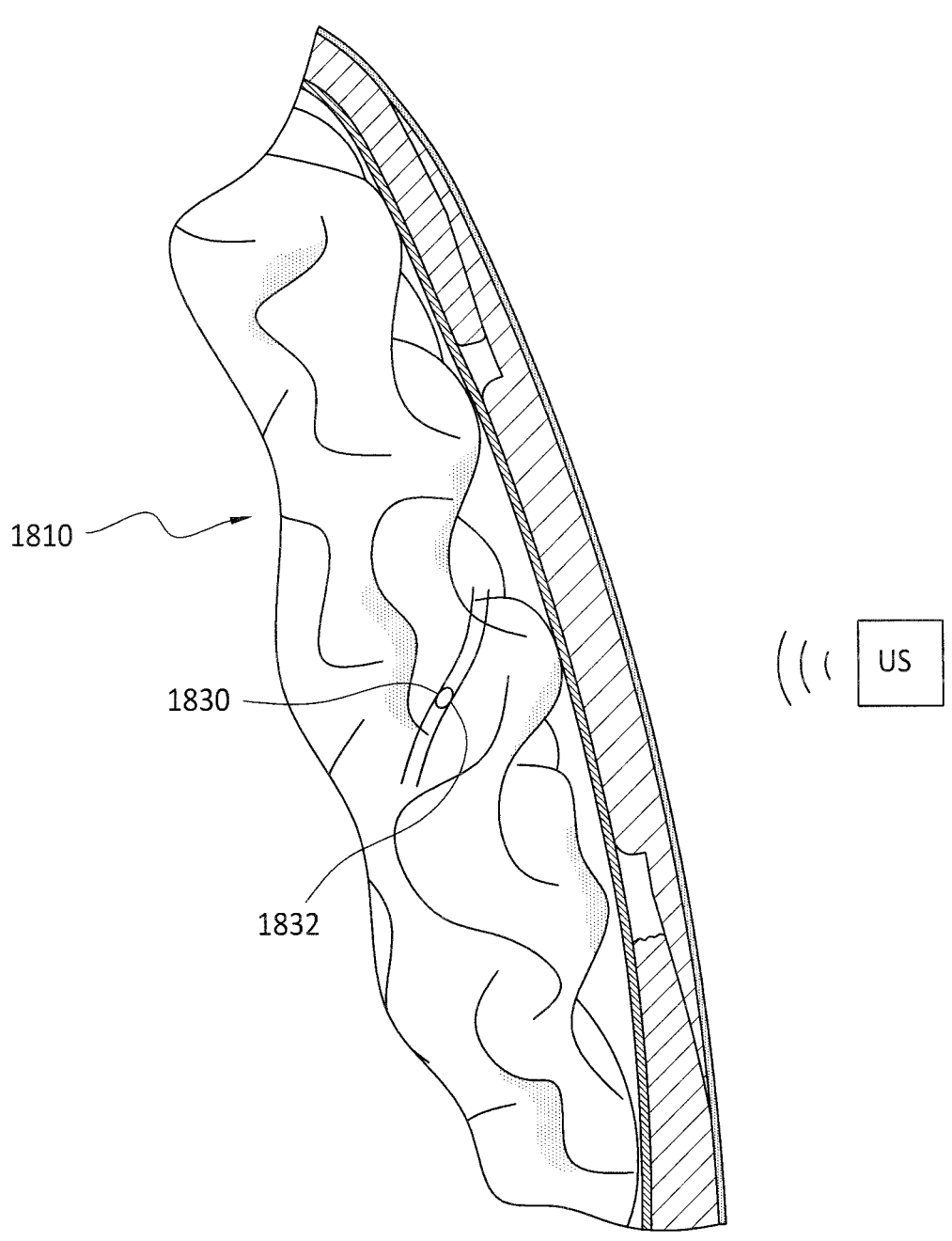
Figure 28:
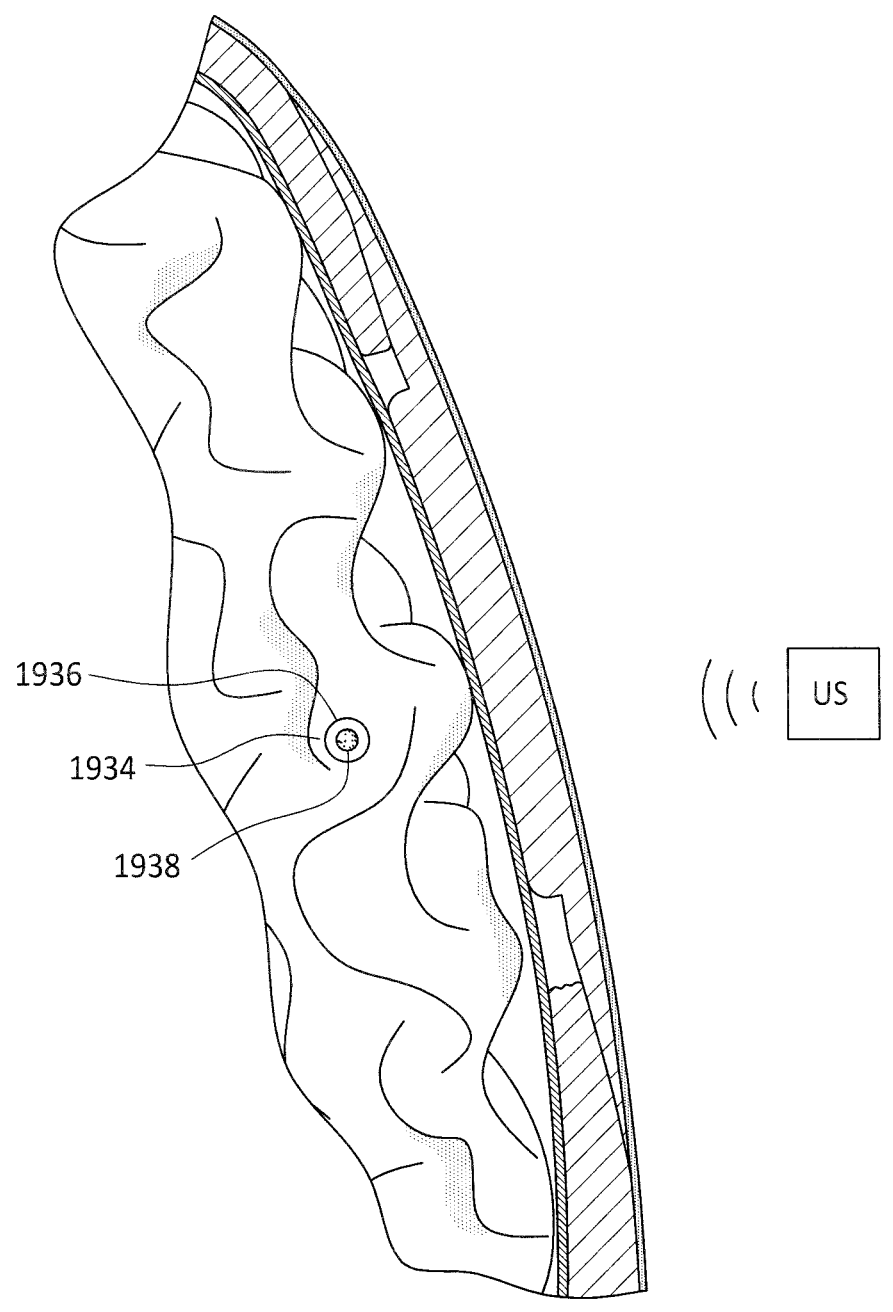

Further still, implementation of the ultrasound transducer (either an implanted ultrasound transducer or an external ultrasound transducer such as a handheld transducer used to image through the sonolucent cranial implant) may be combined with drug delivery by > subjecting a drug 1720 to ultrasound at a specific location within the brain 1710 so that the drug is active at a highly specific location, or to enhance the effectiveness of the drug 1720 through delivery of ultrasound, regardless of whether the drug 1720 is delivered by direct injection into the brain 1710 or is introduced indirectly such as parentally or through an endovascular catheter introduced to a desired location in the brain for this purpose (see FIG. 26),
>
> subjecting the drug 1830 to ultrasound at a specific location within the brain 1810 to assist the drug in passing through the brain blood barrier 1832, such as by causing brain cells to open up to permit larger sized molecules to pass (see FIG. 27), and
>
> therapeutically releasing nano-encapsulated drugs 1934 through the application of ultrasound wherein the ultrasound breaks down the encapsulation material 1936 to release the drug 1938 (see FIG. 28).

It is contemplated such drug delivery mechanisms would find applications in therapies where delivery of a drug directly to the brain might minimize side effects and enhance the overall effectiveness of the drug, for example, in the treatment of Parkinsons, Alzheimers, etc.

Introducing drugs in this manner allows for one to only worry about the drug reaching the treatment area. Introducing drugs in this manner also allows for intermittent dosing as the drug may be selectively activated upon the application of ultrasound, which may be controlled in a highly efficient and effective manner either through an implanted or hand-held ultrasound transducer. Similarly, implementation of an ultrasound transducer array in conjunction with the sonolucent cranial implant would also allow for the application of ultrasound in different areas of the brain so that the location of treatment may be adjusted.

Radiation

Figure 29:
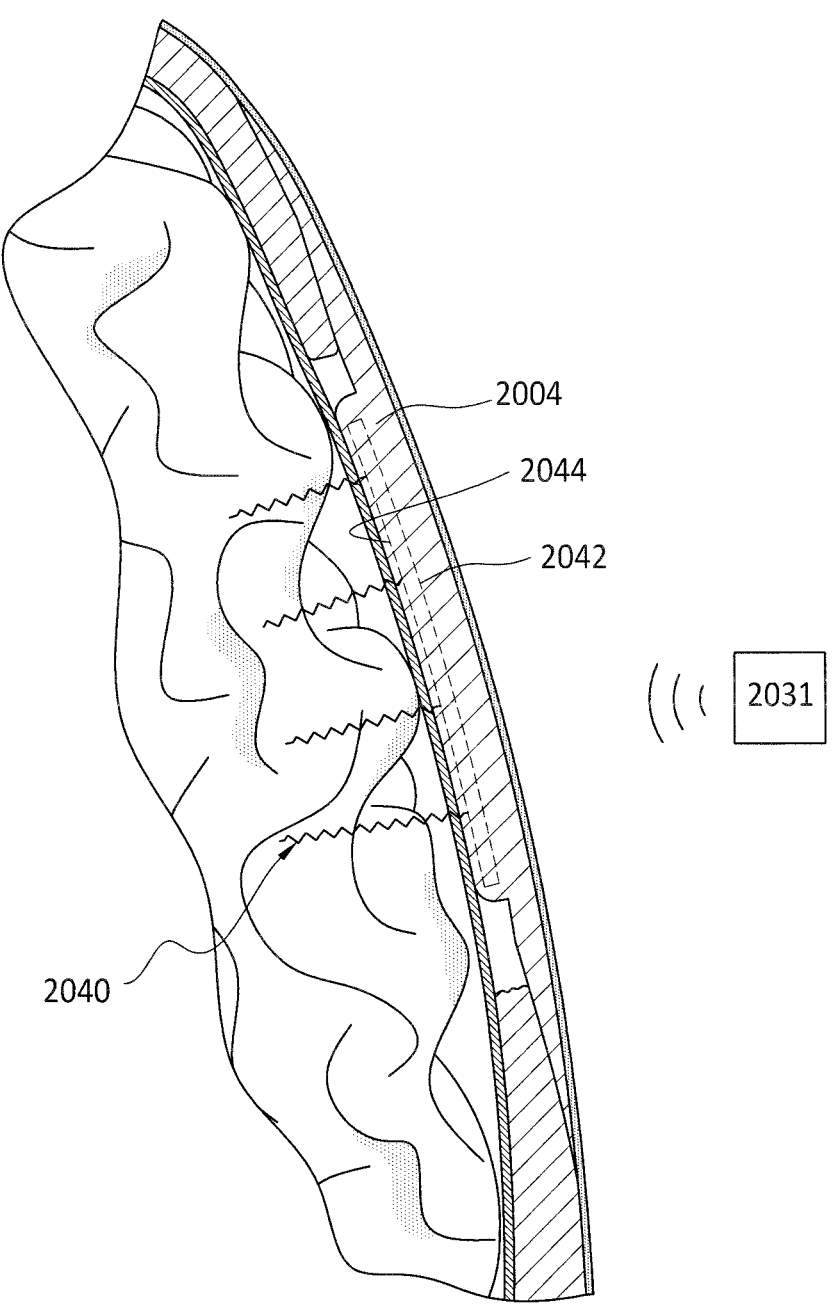
FIGS. 29, 30, 31, 32, 33, and 34 disclose various embodiments where ultrasound is used in association with radiation.

Further still, and with reference to FIG. 29, the ultrasound transducer 2031 (either an implanted ultrasound transducer or an external ultrasound transducer such as a handheld transducer used to image through the sonolucent cranial implant) may be used in conjunction with radiation. For example, therapeutic or imaging radiation 2040 may be delivered through or from the sonolucent cranial implant 2004 and that radiation 2040 may be observed and/or manipulated using the ultrasound transducer 2031. In accordance with such an embodiment, a shielded radiation source 2042 may be positioned in the sonolucent cranial implant 2004 and the radiation 2040 subsequently exposed by opening a window of the shield 2044 or moving/rotating a portion of the shield to expose the brain to the radiation.

Figure 30:
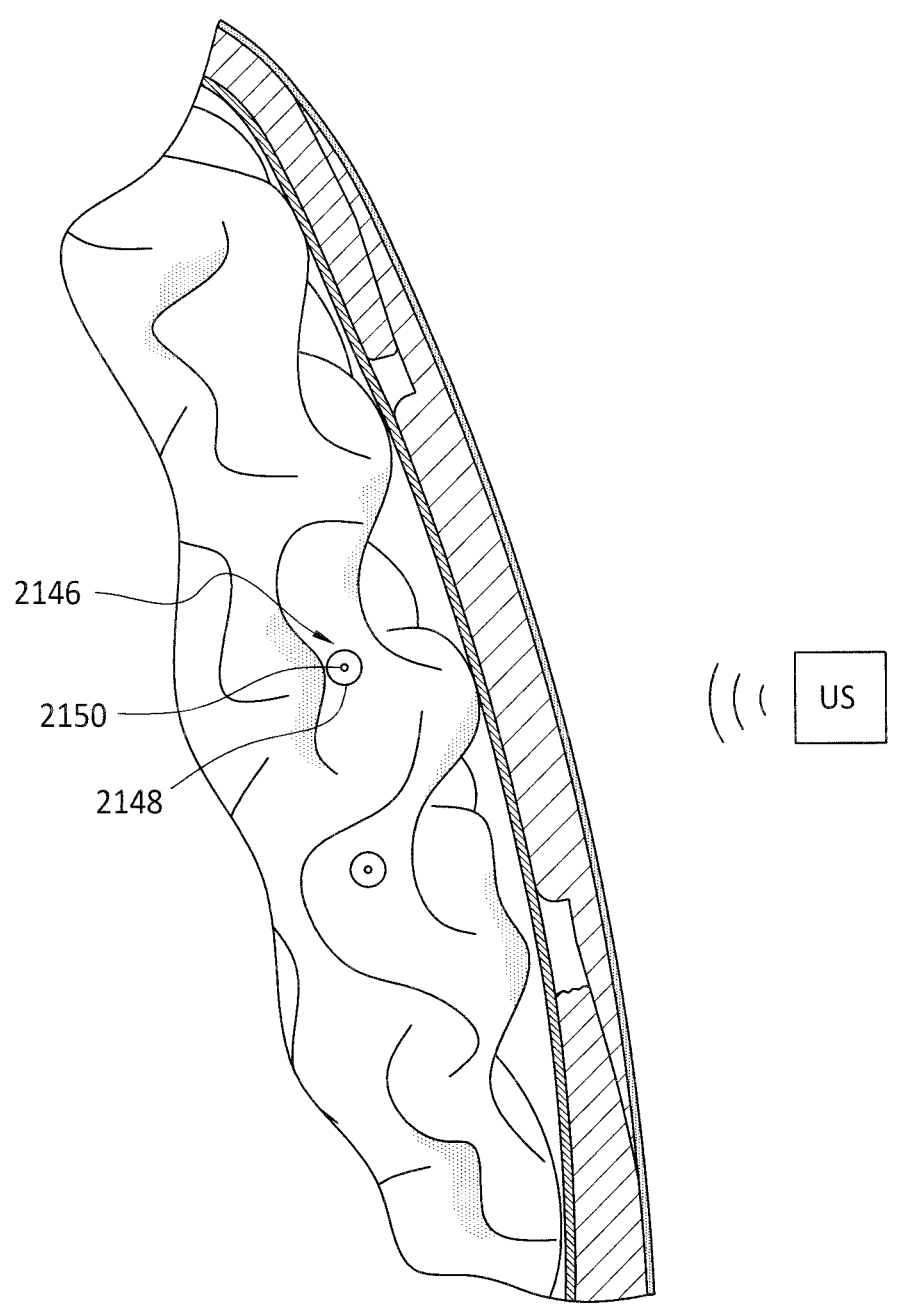
Figure 31:
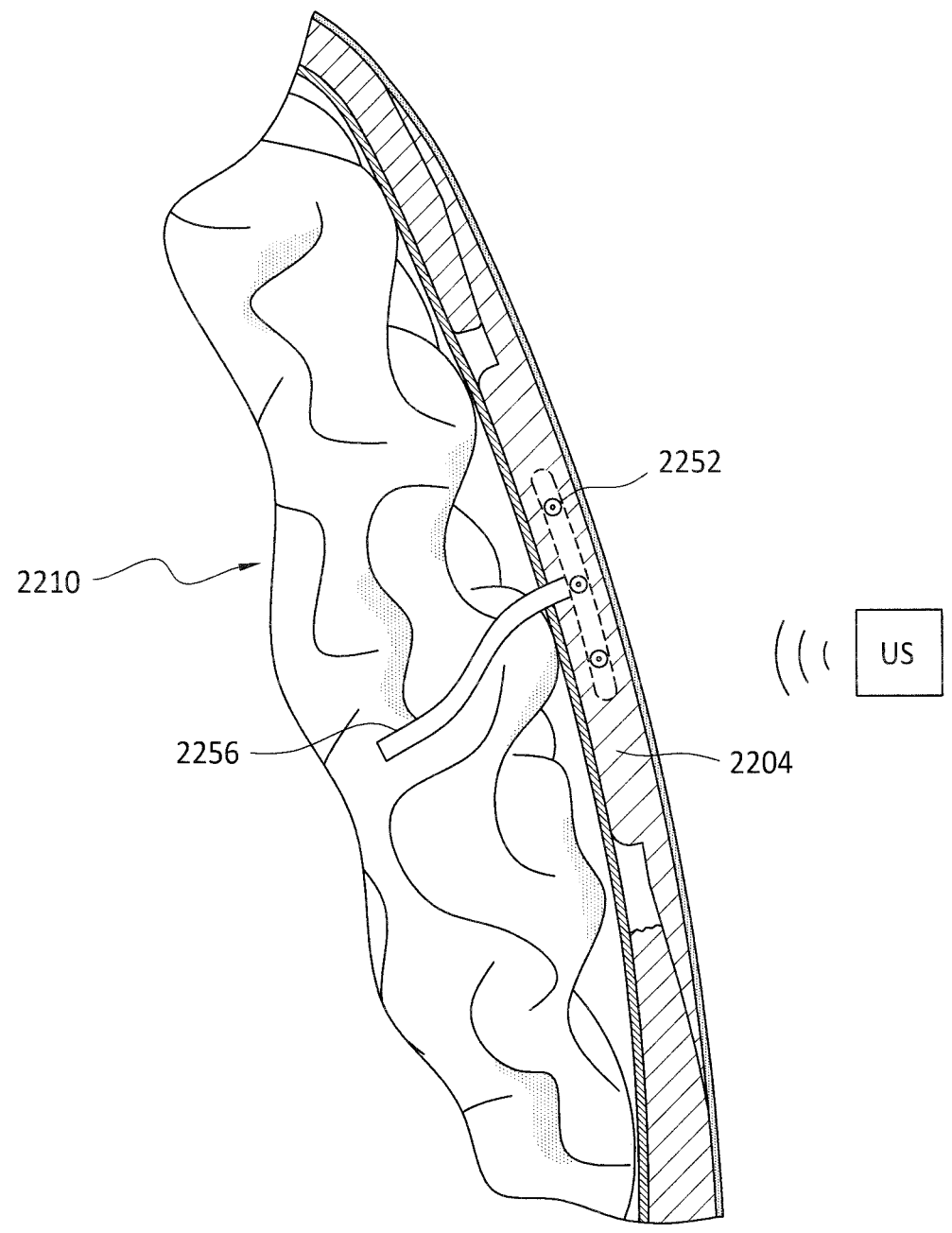

Alternatively, the radiation may be in the form of nano-encapsulated radiation seeds 2146 wherein the ultrasound breaks down the encapsulation material 2148 to release the radiation seed 2150 (see FIG. 30). Further still, small radiation seeds 2252 may be housed in a shielded portion 2254 of a sonolucent cranial implant 2204, and the radiation seeds 2252 are selectively deployed from the shielded portion 2254 to the brain via a catheter 2256 that extends from the sonolucent cranial implant 2204 to a targeted portion of the brain 2210 for periodic radiation delivery (see FIG. 31). It is anticipated the seeds could be pulled back into the shielded area as desired to control the timing, dosage, and extent of radiation treatment. Such radiation treatment could be done with or without the use of an ultrasound transducer to visualize such delivery. The delivery of radiation seeds or the like could be done through an endovascular catheter under ultrasound image guidance and visualization through the sonolucent cranial implant with either implanted or external ultrasound transducer(s).

Figure 32:
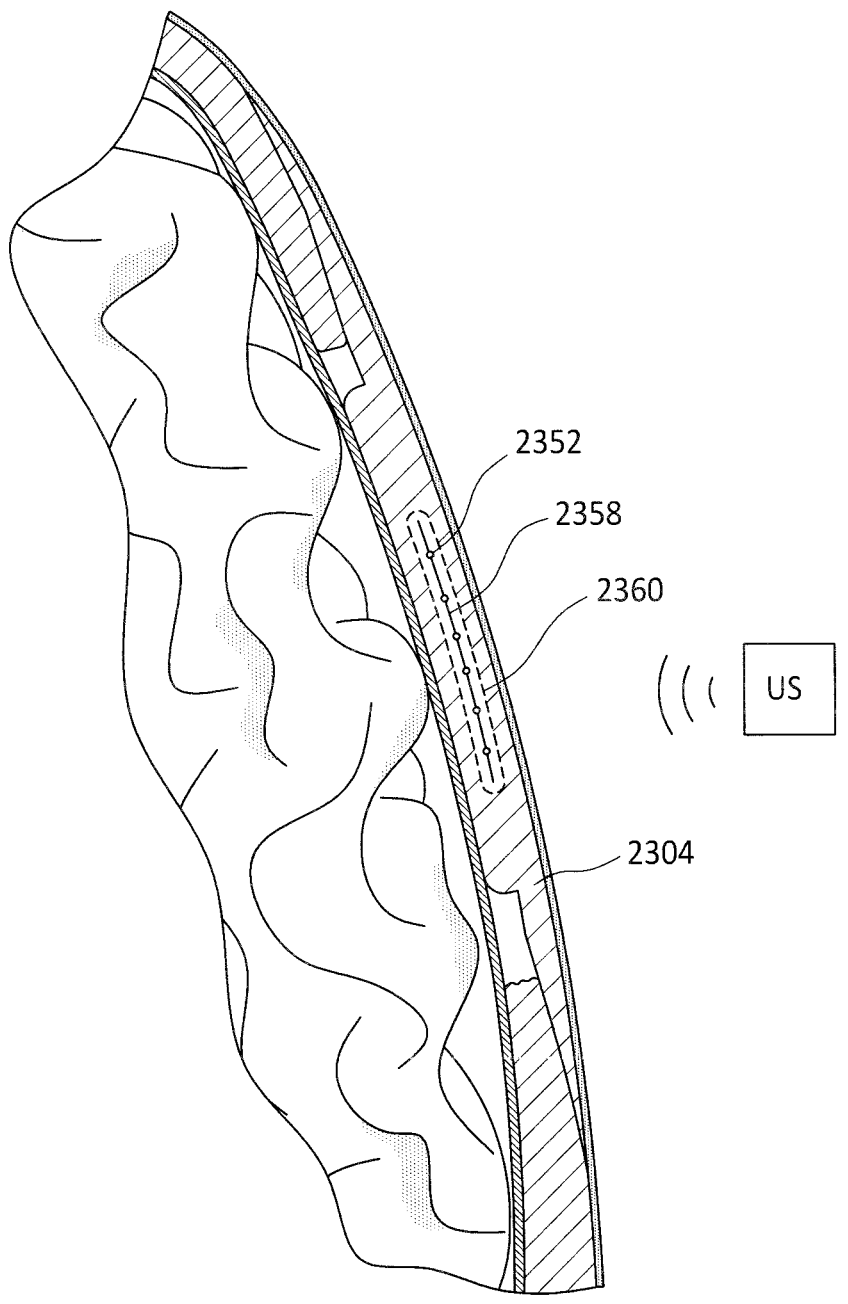
Figure 33:
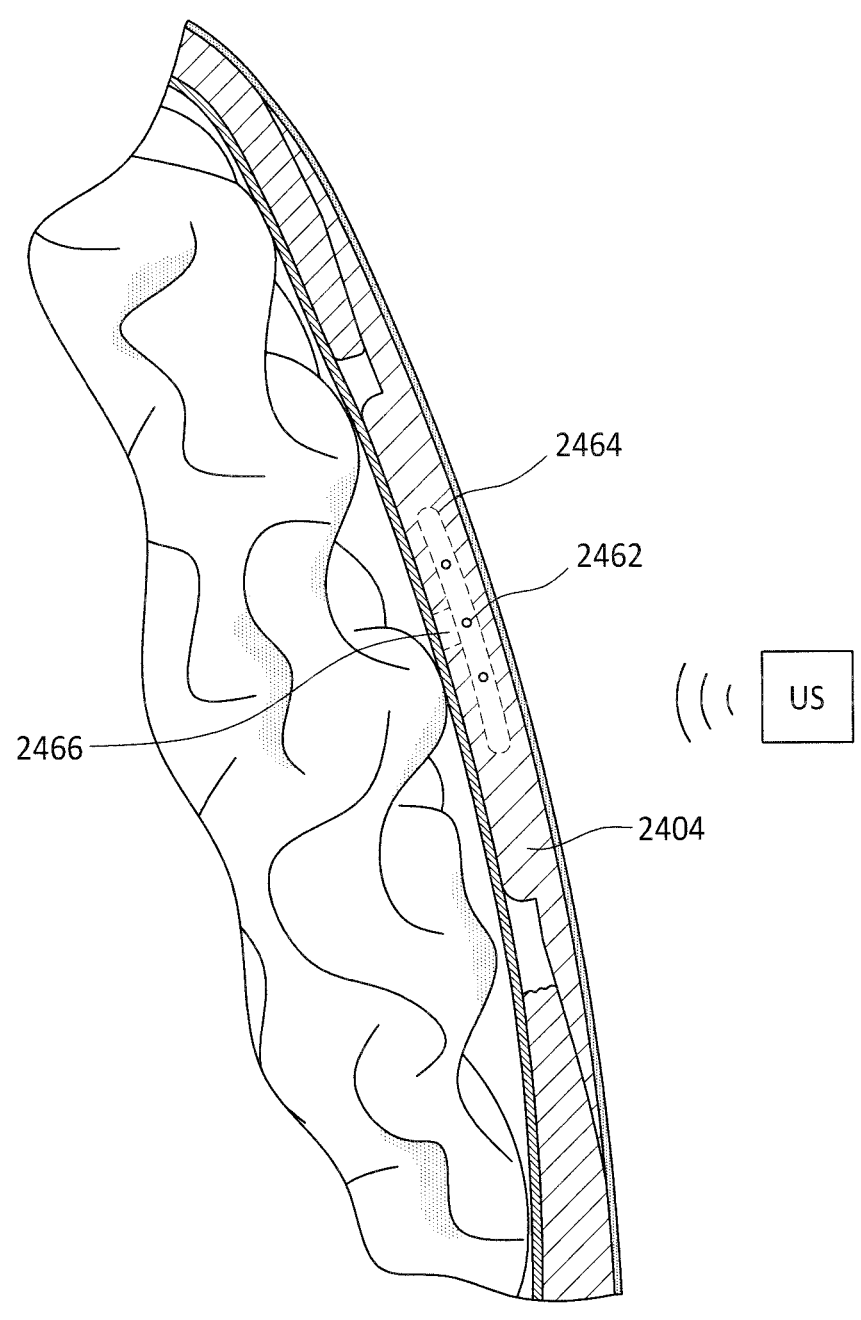
Figure 34:
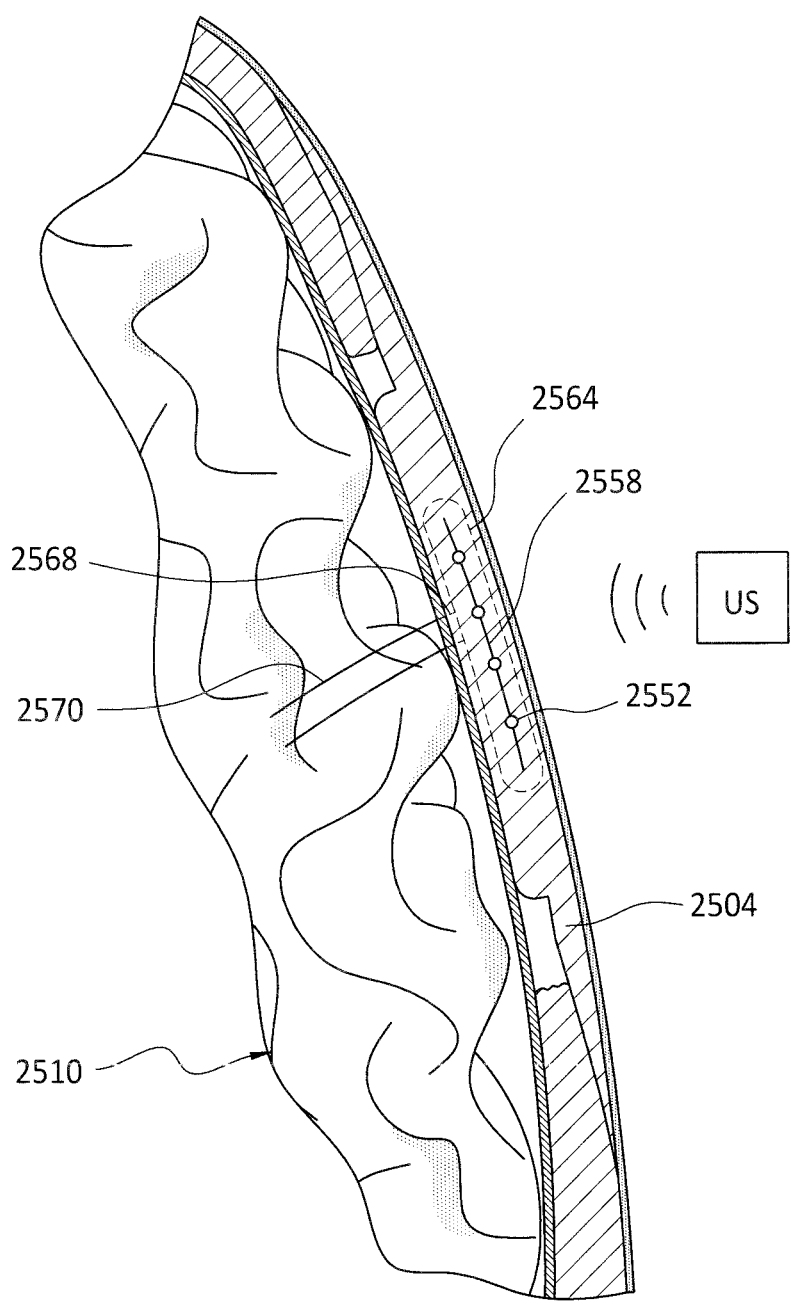

Alternatively, if radiation seeds 2352 are entrained in a ribbon 2358 or the like to be deployed from a shielded safe 2360 disposed within a sonolucent cranial implant 2304, the deployment of the radiation seeds 2352 could be imaged and observed with ultrasound through a sonolucent cranial implant (see FIG. 32). Of course, radiation delivered from a sonolucent cranial implant could be delivered independent of any ultrasound imaging. For example, if the radiation source 2462 is housed within a shielded safe 2464 within the sonolucent cranial implant 2404, a window 2466 could selectively be opened through the shielded implant 2204 to expose the radiation source 2462 to brain tissue through the window 2466 with the radiation source remaining wholly contained within the sonolucent cranial implant 2404 (see FIG. 33). In yet a further alternative, the shielded safe 2564 may be connected to a conduit 2568 within the cranial implant 2504 which leads to an external surface of the sonolucent cranial implant 2504, which surface may be directed toward brain tissue. The ribbon 2558 containing the radiation seeds 2552 may travel through the conduit 2568 and optionally through a catheter 2570 extending from the conduit 2568 into the brain 2510 such that the radiation source travels to a predetermined location in the brain 2510 to deliver radiation to the tissue surrounding the predetermined location. The radiation source may be withdrawn back into the shielded safe 2564 when radiation treatment is not to be delivered (see FIG. 34). Such radiation delivery may be performed with or without ultrasound imaging.

Home Monitoring

With the ability to reliably, conveniently, and accurately take ultrasound images of the brain anatomy the possibility of applications for diagnosis and treatment are overwhelming. For example, and in accordance with one application, a patient with a cranial implant using a handheld ultrasound transducer in accordance with the embodiments disclosed above, will be able to regularly, for example, daily, attach the ultrasound transducer to a smartphone (or other portable communication device capable of receiving and transmitting data) and take an ultrasound image of his or her brain anatomy using the guidance of the alignment mechanisms offered by way of the present invention. The ultrasound image may then be transmitted to the medical practitioner who may then review the ultrasound image, compare it to prior ultrasound images, and take appropriate action. It is further appreciated artificial intelligence may be applied to read the images and make determinations regarding the need for further action.

In accordance with the embodiments discussed above with reference to FIGS. 4 to 11, and particularly FIGS. 10 and 11, these embodiments allow for the implementation of a home monitoring system where a caregiver or the patient takes images at scheduled times and forwards the images to a medical practitioner, for example, an ultrasound specialist. The caregiver or patient sets the ultrasound transducer to specific settings as discussed above, positions the transducer at the predefined locations along the sonolucent cranial implant, and gathers ultrasound images. The collected images are then transmitted to the ultrasound specialist via know data transmission techniques.

Figure 35:
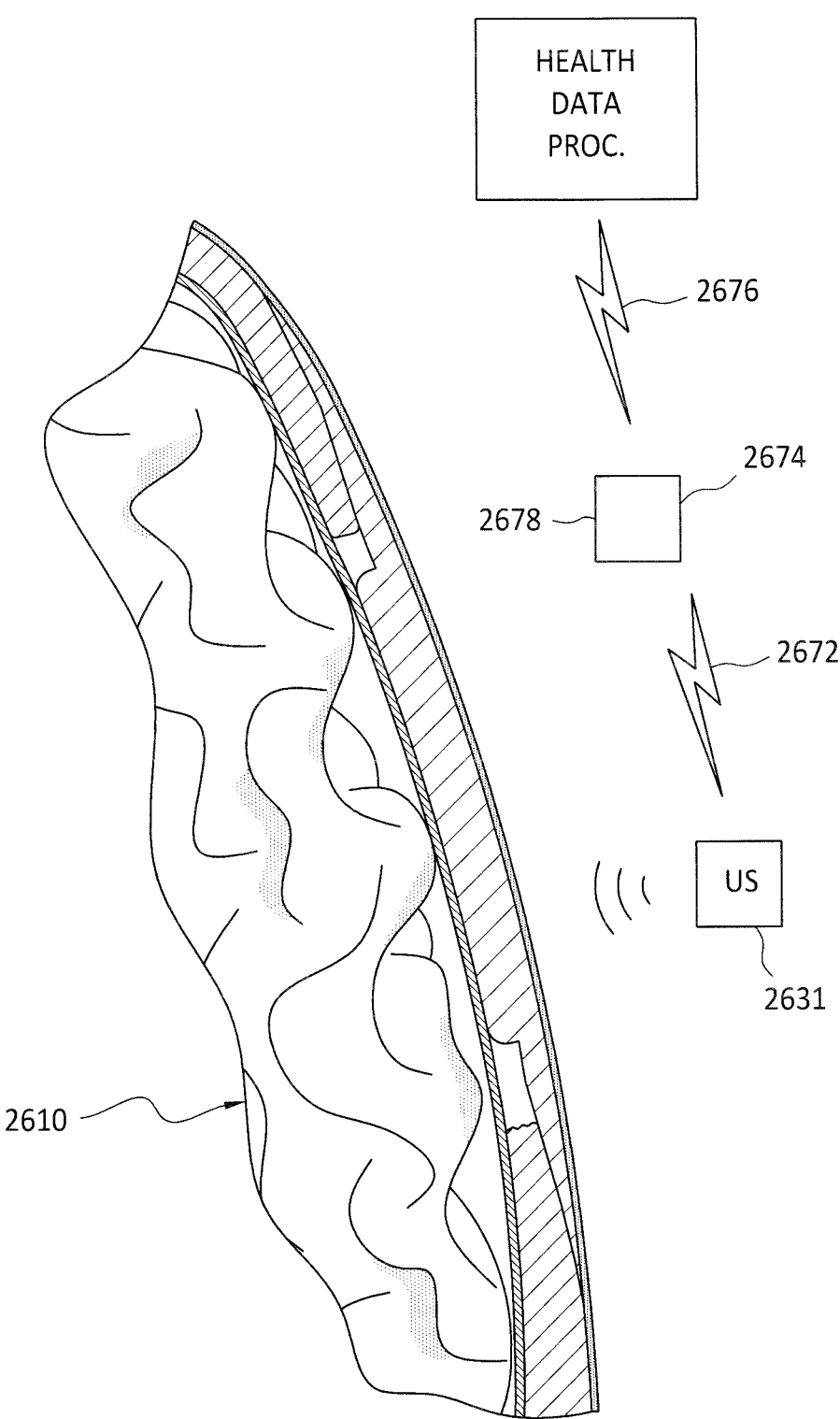
FIG. 35 is a schematic of a home monitoring system.

In accordance with a disclosed embodiment, and with reference to FIG. 35, the ultrasound image data 2672 is conveniently transmitted via a smartphone application 2674 that communicates with the ultrasound transducer 2631 to facilitate HIPAA compliant data transfer 2676. Considering the use of such a smartphone application, it would be possible to use the smartphone application 2674 as a mechanism for setting desired operating parameters for the ultrasound transducer 2631, wherein the operating parameters may be part of a program of medical diagnostics preprogrammed by the medical team responsible for the patient's treatment.

Further still, the alignment markings discussed above with regard to FIG. 8 are used to align the handheld ultrasound transducer 2631 at various preselected locations within the brain 2610 so as to achieve specific diagnosis and treatment goals.

In accordance with such an embodiment, the smartphone app 2674 operating in conjunction with the ultrasound transducer 2631 would be capable of using the alignment markings previously discussed to ensure proper alignment of the ultrasound transducer 2631 during the process of taking images. For example, it is contemplated the smartphone 2678 would provide and audible, visual, or tactile warning when the ultrasound transducer 2361 is properly aligned so that the patient (or individual assisting the patient) will know that a proper image has been generated.

A patient with a sonolucent cranial implant having an integrated ultrasound transducer would be able to take similar actions. For example, the integrated ultrasound transducer would be programmed to take regular ultrasound images of his or her brain anatomy and the patient would simply need to transfer those images to a smartphone (or other portable communication device capable of receiving and transmitting data), which would then transfer the data for further review as discussed above.

Ultrasound Data Fused With Other Data Sources

As discussed below in greater detail, the imaging data obtained from such an ultrasound transducer may be combined with imaging data from other technologies, and such data may be stored and overlayed with other imaging studies. In practice, the raw data is sent to a receiver (Bluetooth, internet, Wi-Fi, to a physical device [memory stick or SD card]). Thereafter, analysis is performed, and the formatted files are sent to a receiver (Bluetooth, internet, Wi-Fi, to a physical device [memory stick or SD card])

In particular, it has been known that for multiple decades to fuse MRI images to CT scans or X-ray scans, but no one has been motivated to merge ultrasound images with another format of imaging, such as CT, MRI, or X-ray. There is probably good reason for this.

MRI image fusion with CT scans or X-rays makes sense. The CT or X-ray image bone well, and the MRI images brain soft tissue. Merging the two is important to guiding the surgeon how to operate on the brain. The image fusion works by identifying bone landmarks in the CT scan and superimposes the MRI image on the CT scan so the surgeon can look at the MRI image and know where they are based on the bone landmarks. Sometimes the system has the user select landmarks in both images, CT scan and MRI, and match them for cross-reference purposes.

Up until the present invention for providing sonolucent windows to the brain via low sound loss static cranial implant, there has been no reason to consider image fusion with ultrasound images. Ultrasound can't image through the brain and has not generally been used for brain imaging.

The combination of ultrasound imaging data and other data enhances treatment in previously unappreciated ways and may be achieved in various ways achieving various goals. For example, and in accordance with a first embodiment, the ultrasound imaging data of the brain is combined, overlayed, and/or integrated (image fusion) with a CT (computed tomography), MRI (magnetic resonance imaging), fMRI (functional magnetic resonance imaging), or X-Ray taken of the same patient's anatomy before or after the ultrasound study. Particularly, the ultrasound data is obtained through a part of the patient that was reconstructed with a suitably static cranial implant as described herein (when ultrasonography is impeded by poorly attenuated anatomy e.g., cranium). Particular anatomy of note is the neuroanatomy and specifically the brain.

The combination of ultrasound image data with image date from CT, MRI, fMRI, or X-Ray would allow for the active mapping distinct elements of the head including skull anatomy, vascular anatomy, and neurological anatomy. In addition, the CT, MRI, fMRI, or X-Ray images would be used to assist in movement of the ultrasound transducer so as to achieve images of desired brain anatomy. This would be achieved using neural fiducials to properly guide and position the ultrasound transducer. It is appreciated that ultrasound transducers would be operating in the range of 7.5 to 15 MHz when used in conjunction with brain mapping.

Considering the application of such technology to an ultrasound transducer mounted within the cavity of the sonolucent cranial implant, the ultrasound transducer takes the form of an ultrasound transducer array. As such, and in addition to the ability to automatically adjust the frequency and gain of the ultrasound transducer, the ultrasound transducer array allows imaging from different positions to assist in gathering the necessary image data that then may be processed for patient diagnosis and treatment.

Considering the application of such technology to an ultrasound transducer intended to be utilized remote in conjunction with the sonolucent cranial implant, in addition to the ability to automatically adjust the frequency and gain of the ultrasound transducer, the sonolucent cranial implant is further provided with predefined locations for positioning of the ultrasound transducer. This assists in gathering the necessary image data that then may be processed for patient diagnosis and treatment.

In accordance with such an embodiment, the sonolucent cranial implant is provided with a unique marking (radio, magnetic, and/or echogenic marking via bubbles, etching, multi-modality graphic material impregnation, etc.) Triangle mapping (that is, triangulation) with the specific markings enable inter-imaging co-registration/overlay/interdigitation/integration/orientation. In essence using a universal imaging marker with a triangulation registration to fuse or combine imaging modalities including ultrasound.

Implementation of such an embodiment requires acquisition of a CT or X-Ray (or potentially MRI) scan of the brain, acquisition of ultrasound image of the brain, preferably through the sonolucent cranial implant, identification of common landmarks in the ultrasound image and the other image, registration of one image relative to the other, and display of the ultrasound image registered to the CT or X-Ray or MRI image.

In accordance with the application of such technology, it is contemplated that post surgery, with the sonolucent cranial implant filling the cranial opening, an ultrasound image of the brain, which is superimposed on the other images to compare before and after an assess results. The post-surgery implant does not need to be done in the hospital. It could be done in an office visit, or at the patient's home (self-administered or done by a companion or a visiting nurse, physician assistant etc.) with the ultrasound image transferred to the physician's office to be considered on its own or merged with a CT or X-Ray image (pre- or post-surgery)

to assess results. The ultrasound image could be transmitted electronically, such as over the internet, uploaded to a file share application, or transferred in a suitable meeting such as a memory stick.

In addition to combining ultrasound image data with other forms of image data to create a complete picture of the brain anatomy, the ultrasound technology may be combined with other imaging technologies in a manner allowing the ultrasound technology to function as a treatment mechanism as opposed to solely using the ultrasound technology for the purpose of obtaining imaging information. For example, it is known that ultrasound technology may be used for, but not limited to, ablation, brain stimulation, blood brain barrier access techniques, and medication release. It is contemplated such multi-functional use of ultrasound technology would be achieved by utilizing an array of ultrasound transducers wherein the various ultrasound transducers are adapted for differing purposes.

Augmented Reality

The imaging data produced in accordance with the present invention, may be applied in the provision of a real-time surgical augmented reality experience. In particular, the data from ultrasound is processed in real time to recreate 3D imaging for live surgery.

Such augmented reality would be like the medical practitioner performing the procedure were "simulation or overlap" riding in a shuttle inside a live patient's brain the medical practitioner is doing surgery on in real time. The medical practitioner could then see the real-time impact of tumor ablation/fluidics all with just ultrasound and image processing.

3D Ultrasound

The sonolucent cranial implant of the present invention may be applied in the production of 3D ultrasound images. As will be appreciated based upon the following disclosure multiple ultrasound images may be obtained from various orientations and subsequently combined to produce a 3D ultrasound image of the brain anatomy at interest. The various embodiments presented below take advantage of known ultrasound collection techniques, including but not limited to, 2D array scanning, mechanical scanning, tracked freehand scanning, and untracked freehand scanning. Once the 2D ultrasound data is obtained the 3D image is constructed using a known interpolation and approximation algorithm. Thereafter, spatial information obtained from a tracking system is used to place the 3D construction is an appropriate spatial environment. Known techniques include, but are not limited to, pixel-nearest neighbor, voxel nearest neighbor, distance weighted, radial basis function, and image-based algorithms.

Figure 36:
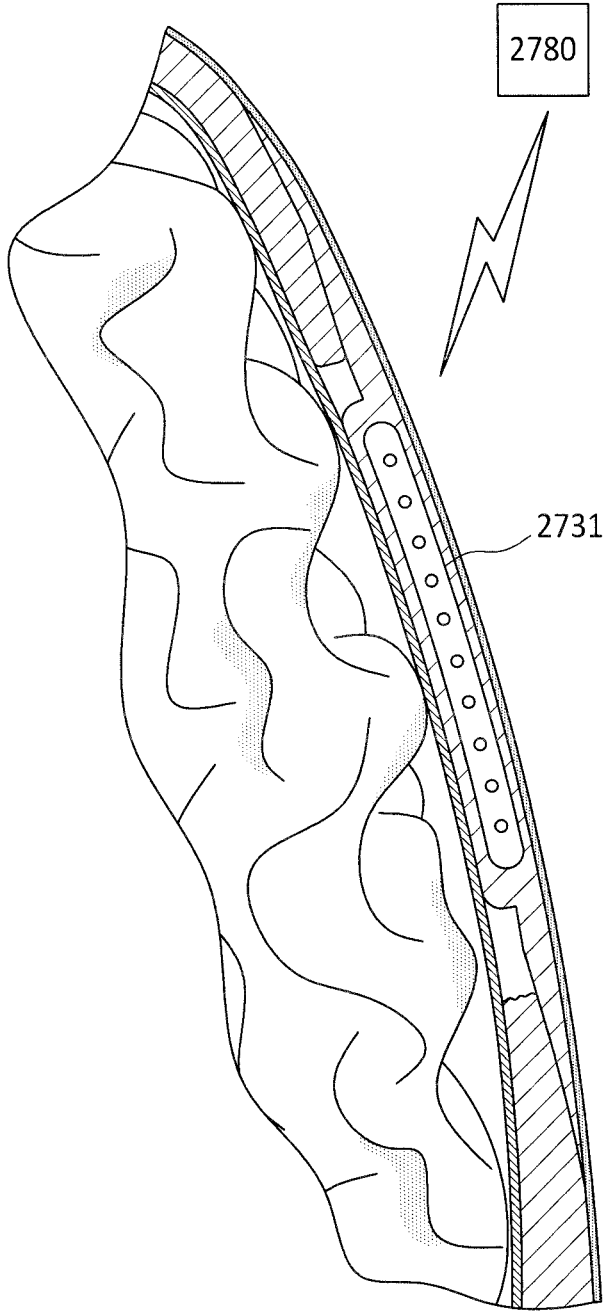
FIG. 36 discloses an ultrasound transducer mounted within the cavity of the cranial implant in accordance with another embodiment.

Considering the application of such technology to an ultrasound transducer mounted within the cavity of the sonolucent cranial implant 2704 with reference to FIG. 36, the ultrasound transducer takes the form of an ultrasound transducer array 2731. As such, and in addition to the ability to automatically adjust the frequency and gain of the ultrasound transducer, the ultrasound transducer array 2731 allows imaging from different positions to assist in gathering the necessary image data that then may be processed via an image processor 2780 for patient diagnosis and treatment. 3D ultrasound images may also be achieved by integrating multiple ultrasound transducers within the sonolucent cranial implant.

Figure 37:
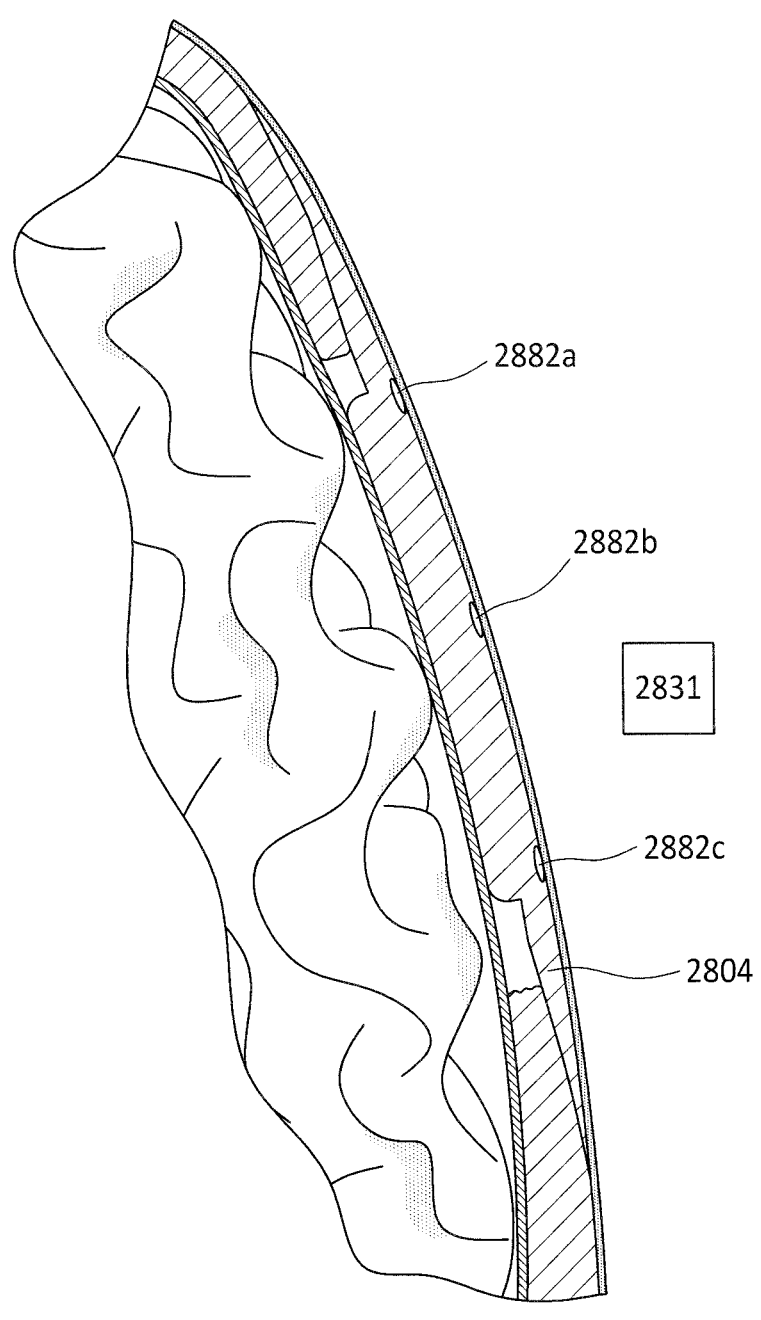
FIG. 37 discloses an ultrasound transducer intended to be utilized remote in conjunction with yet another embodiment.

Considering the application of such technology to an ultrasound transducer 2831 intended to be utilized remote in conjunction with the sonolucent cranial implant 2804 as shown in FIG. 37, in addition to the ability to automatically adjust the frequency and gain of the ultrasound transducer 2831, the sonolucent cranial implant 2804 is further provided with predefined locations for positioning of the ultrasound transducer 2831. This assists in gathering the necessary image data that then may be processed for patient diagnosis and treatment.

In accordance with such an embodiment, the sonolucent cranial implant 2804 is provided with alignment markings 2882a-c that guide a user to position the ultrasound transducer 2831 at various positions relative to the sonolucent cranial implant 2804.

As discussed above with reference to FIG. 8, the alignment feature includes a series of markings at different depths within the base cranial implant member 212 of the sonolucent static cranial implant 204. For example, an outer first static cranial implant marking 237a and an inner second static cranial implant marking 237b are formed along the outer first surface 212o and the inner second surface 212i, respectively, of the base cranial implant member 212 of the static cranial implant 204. One or more additional interior static cranial implant markings 237c may be formed within the body of the base cranial implant member 212 of the static cranial implant 204 and in alignment with the outer first static cranial implant marking 237a and an inner second static cranial implant marking 237b. While an outer first static cranial implant marking 237a, an inner second static cranial implant marking 237b, and at least one additional interior static cranial implant marking 237c are disclosed herein, it is appreciated various combinations of markings may be used within the spirit of the present invention.

The outer first static cranial implant marking 237a, the inner second static cranial implant marking 237b, and the plurality of additional interior static cranial implant markings 237c are aligned such that when the ultrasound transducer 231 is properly aligned with the markings 237a-c, the ultrasound waves will be directed to the proper location within the cranium. Similarly, when one looks through the sonolucent static cranial implant 204 and the outer first static cranial implant marking 237a, the inner second static cranial implant marking 237b, and the at least one additional interior static cranial implant marking 237c merge into a single location identifying image (for example, crosshairs or circles), a specific brain anatomy (or other structural element upon the surface of the brain) is identified by the single location identifying image. When the specific brain anatomy identified by the single location identifying image changes over time, the surgeon will know that something has shifted and will take appropriate action.

Thereafter, and using known technologies, the 2D ultrasound images obtained as the ultrasound transducer 2831 is moved from location to location are combined to produce the desired 3D ultrasound image.

Further still, 3D ultrasound images may also be achieved by integrating a single ultrasound transducer within the cranial implant and moving the ultrasound transducer to obtain 2D ultrasound images from different orientation. These 2D ultrasound images may then be combined to produce a 3D ultrasound image.

Blood Brain Barrier

One application for the use of ultrasound technology as described above involves targeted medicine delivery via blood Brain Barrier (BBB) wherein dilation is achieved via the application of ultrasound activation signals. The ultrasound activation signals may come in numerous modalities, including but not limited to, mechanical, chemical, nuclear, etc., of medicine release.

Through the use of the sonolucent cranial implant, it is possible to apply of ultrasound at a frequency and amplitude known to dilate the Blood Brain Barrier to pass through to targeted anatomy. For example, ultrasound transducers operating a 0.26 MHz to 2.04 MHz are known to be utilized in Blood Brain Barrier procedures. This allows for the passage of a medicine that treats specific brain pathologies and/or diseases but cannot normally pass the blood brain barrier. The ultrasound transducer can also target specific anatomy and dilate the intended target area thereby passing the medicine into an intended and specific anatomy.

Figure 16:
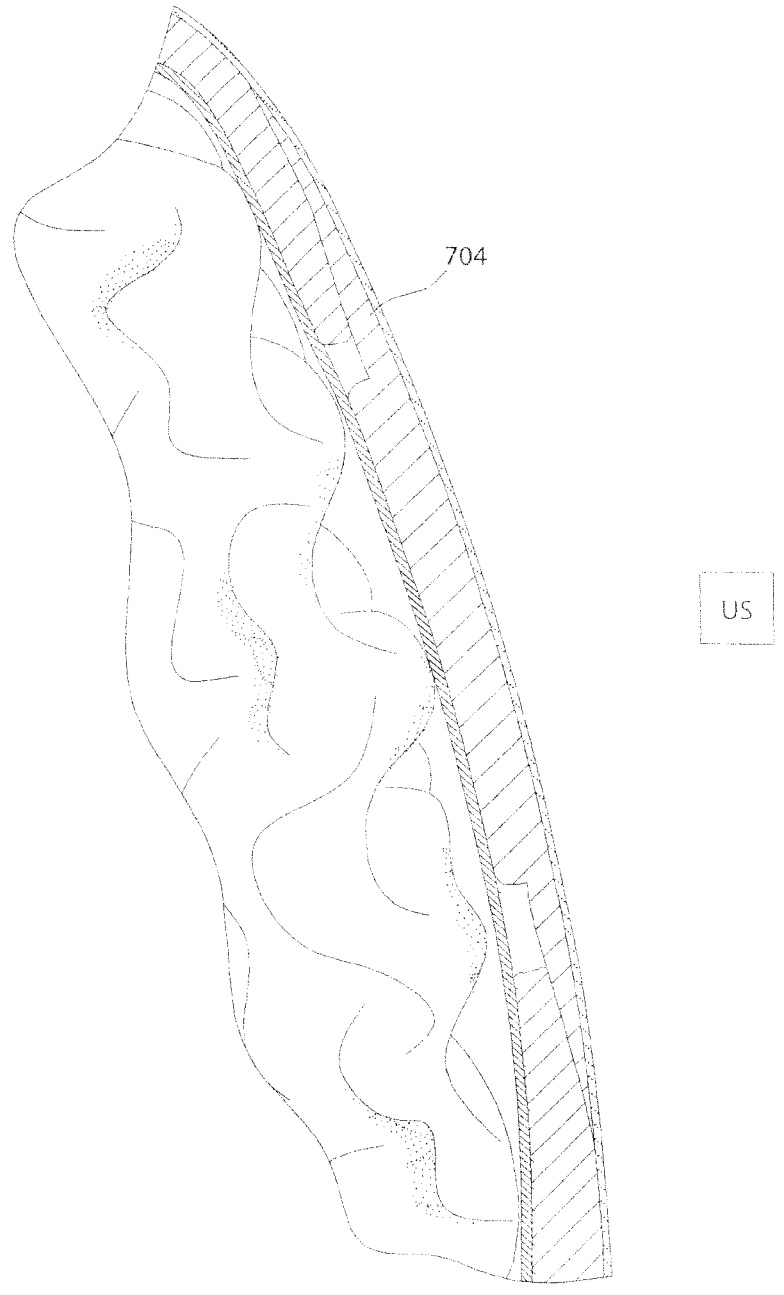
FIGS. 16, 17, 18, 19, and 20 are cross section views of craniofacial implants in accordance with seventh, eighth, ninth, tenth, and eleventh embodiments.

While the sonolucent cranial implant as described above may be used in accessing the blood Brain Barrier, it is appreciated the sonolucent cranial implant may take various forms when used in accessing the blood Brain Barrier. For example, and in accordance with an embodiment as disclosed in FIG. 16, a reconstructive sonolucent cranial implant 704 replaces the skull in a trajectory that allows for ultrasound to pass through and dilate the blood brain barrier, allowing medicine that cannot normally pass through the blood brain barrier to do so.

Figure 17:
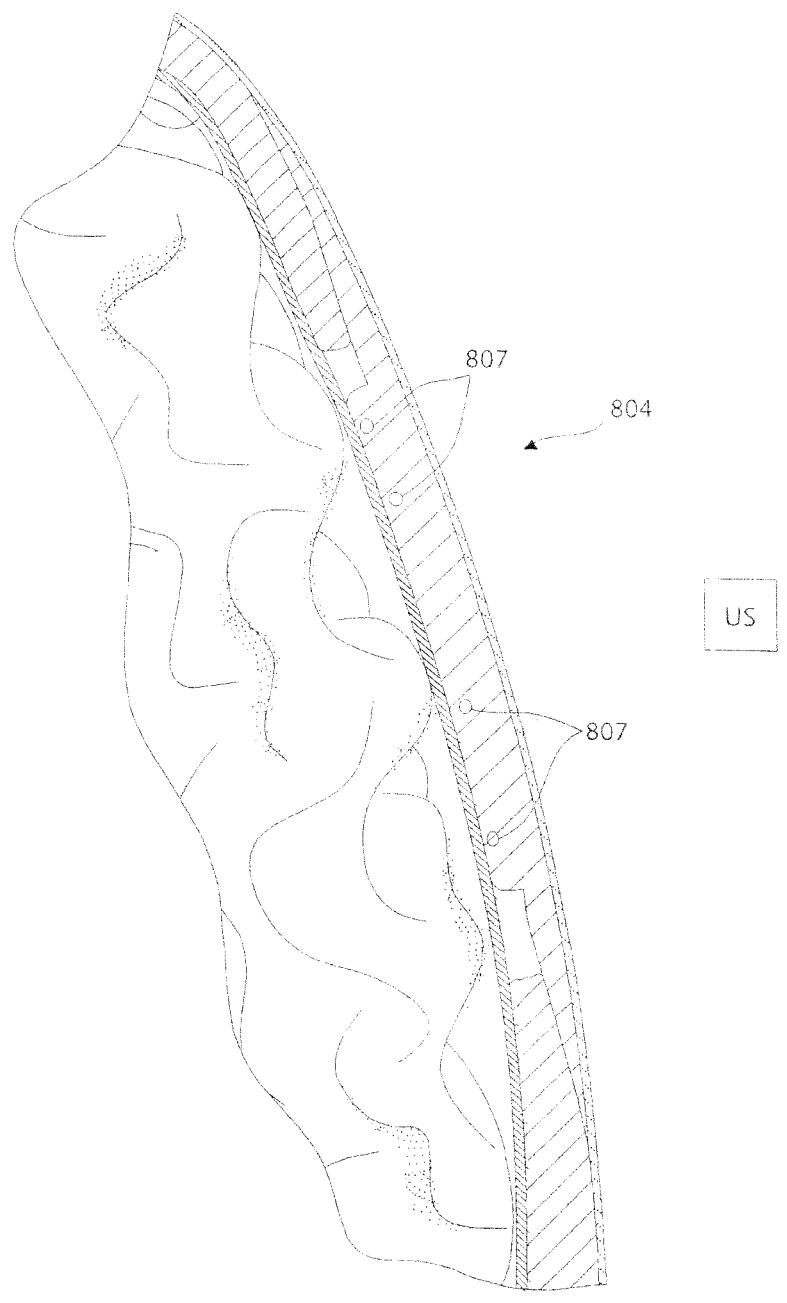

In accordance with another embodiment disclosed with reference to FIG. 17, the sonolucent cranial implant 804 is a reconstructive device that replaces the skull and encapsulates a medicine 807. In accordance with such an embodiment, the reconstructive device allows ultrasound waves to pass therethrough and the encapsulation of the medicine is triggered to release medicine when ultrasound waves contact it (either via capsule dissolving or other).

Figure 18:
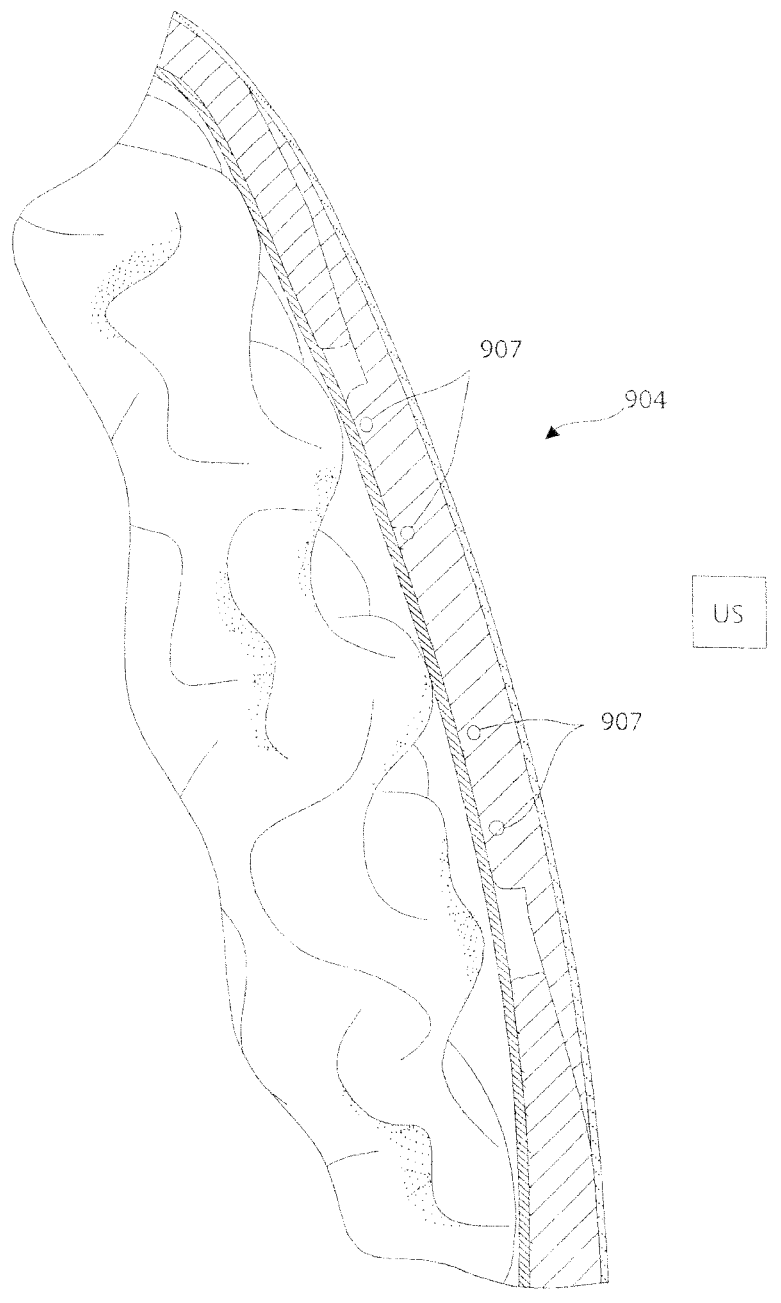

In accordance with yet another embodiment disclosed with reference to FIG. 18, cranial implant 904 is a reconstructive implant that replaces the skull in a trajectory that allows for ultrasound to pass through and dilate the blood brain barrier. The cranial implant also encapsulates a medicine 907 and allows ultrasound waves to pass therethrough and the encapsulation of the medicine is triggered to release medicine when ultrasound waves contact it (either via a capsule dissolving or other mechanism).

Figure 19:
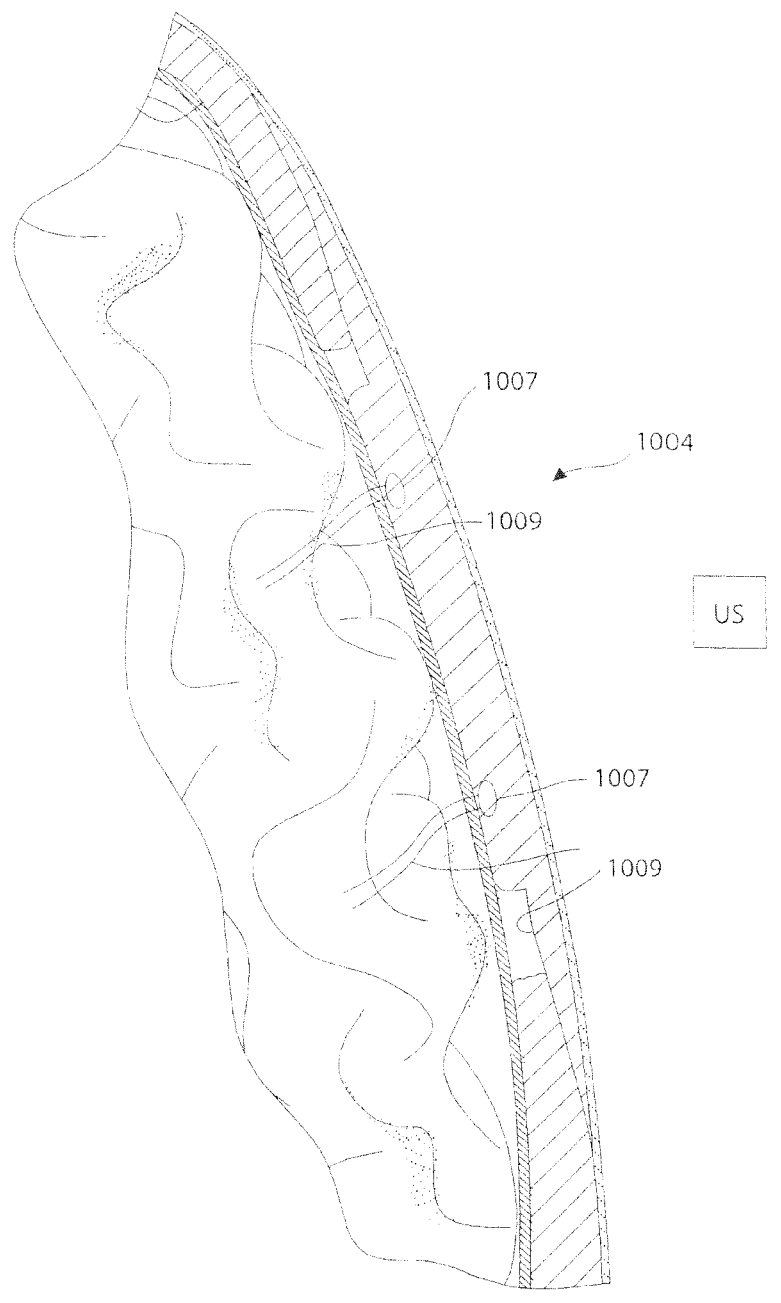

In accordance with a further embodiment disclosed with reference to FIG. 19, the methodology is implemented with a reservoir of medicine 1007, with or without a catheter 1009 leading to a specific anatomical target, within a reconstructive cranial implant 1004. The cranial implant 1004 allows for ultrasound waves to pass through. The ultrasound waves open the reservoir 1007 and the medicine is delivered to the intended target.

Figure 20:
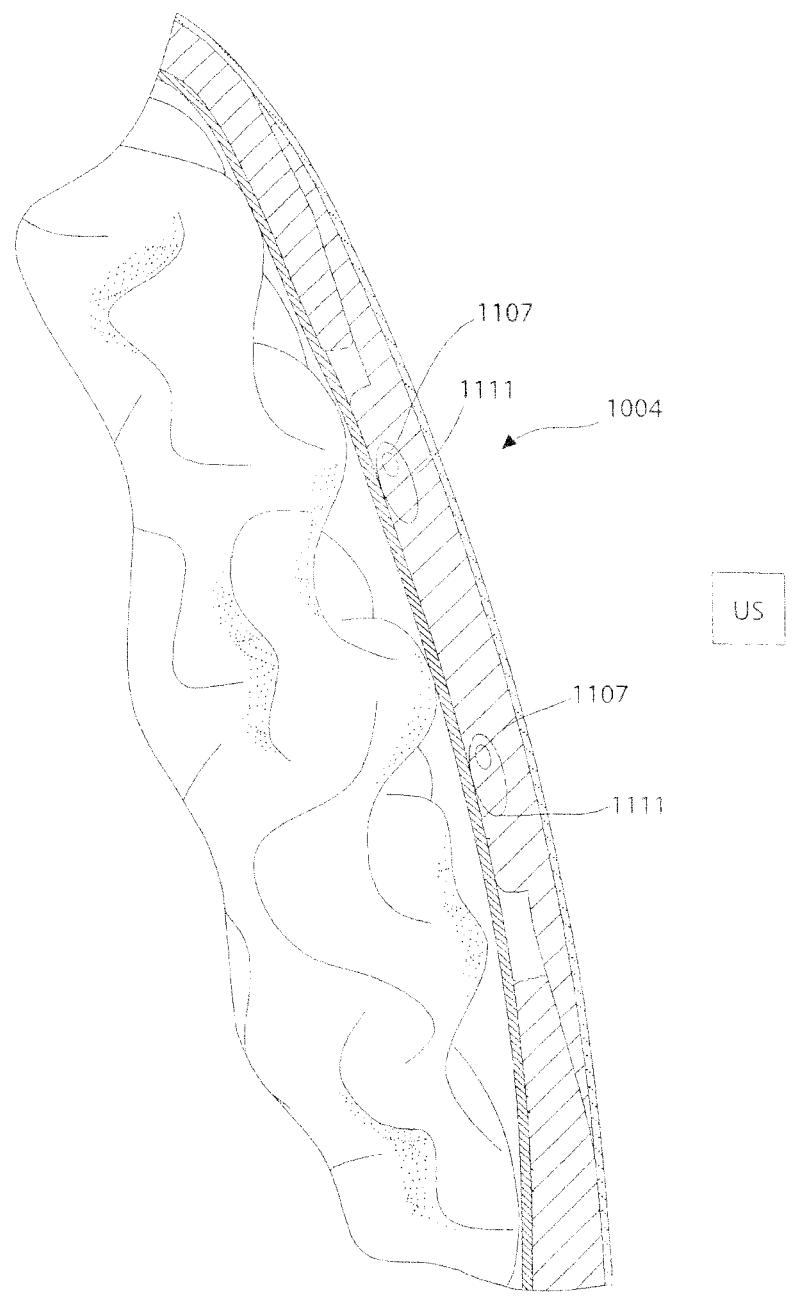

In accordance with a further embodiment disclosed with reference to FIG. 20, the methodology is implemented with a medicine pump 1111 capable of perfusing medicine to a specific anatomical target. The medicine pump 1111 is positioned within a sonolucent cranial implant 1104. The pump 1111 and sonolucent cranial implant 1004 are made of or impregnated within sonolucent material allowing release of the medicine held within a reservoir 1107 associated with the pump 1111 when triggered with ultrasound. In conjunction with such an embodiment, the medicine can be targeted and directed to specific neuroanatomy by dilating the blood Brain Barrier in the desired anatomy.

HIFU/Thermal Ablation

The utilization of ultrasound in conjunction with the sonolucent implants of the present invention allows for the extension to functionalities involving High-Intensity Focused Ultrasound (HIFU) and/or Thermal Ablation through the application of HIFU.

As those skilled in the art will appreciate, HIFU precisely delivers focused ultrasound waves to tissue in a manner destroying or otherwise altering the tissue. The procedure commonly requires a craniectomy to provide access to for the passage of the focused ultrasound to the specific neuro-anatomy. As employed in accordance with the present implant, the HIFU transducer responsible for the transmission of the HIFU is either incorporated within the implant for extended treatment periods or the HIFU transducer is external to the implant and the HIFU is transmitted through the implant and into the neuroanatomy. Thermal ablation procedures involving HIFU are known to use ultrasound transducers operating a 0.2 MHz to 4.0 MHz. While neuromodulation procedures are known to use ultrasound transducers operating at 1 MHz to 43 MHz.

Conditions such a chronic neuropathic pain, essential tremors, obsessive-compulsive disorders, Parkinson's disease, ischemic stroke, hemorrhagic stroke, immunomodulation, and antitumor immunity are known to be treated by HIFU, and the treatment may be enhanced and improved through the utilization of the sonolucent implants of the present invention. Similar, HIFU is known to be useful in delivery various treatment agents, including, but not limited to chemotherapeutic agents. Antibodies, growth factors, and/or genes. HIFU is also known to be useful in opening the blood brain barrier for the delivery of drugs, including, but not limited to liposomal doxorubicin, nanoparticles, fluorophores, and naked DNA.

Considering the various embodiments disclosed above, it is appreciated attachment to the skull is facilitated through structures that maintain the translucent, sonolucent, and radiolucent characteristics of the present clear sonolucent cranial implant. In accordance with each of the embodiments described below, the clear sonolucent cranial implant is a modified version of a low-profile cranial implant commonly used and known by those skilled in the art of cranial surgical procedures. The clear sonolucent cranial implant is shaped and dimensioned for integration into the structure of a patient's skull; that is, the clear sonolucent cranial implant has a geometry that substantially conforms to a resected portion of the patient's anatomy to which the clear sonolucent cranial implant is to be secured.

Whether the ultrasound transducer is a traditional hand-held transducer or the ultrasound transducer is shaped and dimensioned for positioning within the cavity of the cranial implant, the ultrasound transducer is optimized via hardware, firmware, and/or software to perform the functions discussed above.

While the preferred embodiments have been shown and described, it will be understood that there is no intent to limit the invention by such disclosure, but rather, it is intended to cover all modifications and alternate constructions falling within the spirit and scope of the invention. The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

The invention claimed is:

1. A craniofacial implant, comprising:
a low profile intercranial device including a static cranial implant and a functional neurosurgical implant, the static cranial implant being sonolucent and including an outer first surface and an inner second surface; and
an ultrasound transducer in the form of an array of ultrasound transducers that automatically adjusts frequency and gain of the ultrasound transducers to assist in gathering the necessary image data that then may be processed for patient diagnosis and treatment.

2. The craniofacial implant according to claim 1, wherein the craniofacial implant is manufactured from clear poly (methyl methacrylate) (PMMA).

3. The craniofacial implant according to claim 1, wherein the craniofacial implant is optically lucent, and radiolucent.

4. The craniofacial implant according to claim 1, wherein the craniofacial implant is radiolucent.

5. The craniofacial implant according to claim 1, wherein the functional neurosurgical implant includes an ultrasound transducer integrated with the static cranial implant.

6. The craniofacial implant according to claim 5, further including an additional functional neurosurgical implant.

7. The craniofacial implant according to claim 1, wherein the ultrasound transducer is pre-set to frequencies, gain, and/or field of view for imaging and interacting with neuroanatomy, the ultrasound transducer operating between 1 MHz and 9 MHz when the ultrasound transducer is used for imaging purposes and the ultrasound transducer operating between 150 KHz to 1.2 MHz when the ultrasound transducer is used for therapeutic purposes.

8. The craniofacial implant according to claim 7, wherein the ultrasound transducer operates at a frequency of approximately 1 MHz to approximately 3 MHz, a dynamic range of approximately 55 dB to approximately 65 dB, and a gain of approximately 55 dB to approximately 70 dB.

9. A craniofacial implant, comprising:
a low profile intercranial device including a static cranial implant and a functional neurosurgical implant, the static cranial implant being sonolucent and including an outer first surface and an inner second surface; and
an ultrasound transducer in the form of an array of ultrasound transducers that automatically adjusts frequency and gain of the ultrasound transducers to assist in gathering the necessary image data that then may be processed for patient diagnosis and treatment, the ultrasound transducer is separate and distinct from the static cranial implant, wherein the ultrasound transducer works in conjunction with the functional neurosurgical implant that has been integrated into the static cranial implant.

10. The craniofacial implant according to claim 9, wherein the static cranial implant includes an alignment feature.

11. The craniofacial implant according to claim 10, wherein the alignment feature includes a series of markings at different depths within the static cranial implant.

12. The craniofacial implant according to claim 9, wherein the ultrasound transducer is pre-set to frequencies, gain, and/or field of view for imaging and interacting with neuroanatomy, the ultrasound transducer operating between 1 MHz and 9 MHz when the ultrasound transducer is used for imaging purposes and the ultrasound transducer operating between 150 KHz to 1.2 MHz when the ultrasound transducer is used for therapeutic purposes.

13. The craniofacial implant according to claim 12, wherein the ultrasound transducer operates at a frequency of approximately 1 MHz to approximately 3 MHZ, a dynamic range of approximately 55 dB to approximately 65 dB, and a gain of approximately 55 dB to approximately 70 dB.

14. The craniofacial implant according to claim 9, wherein the cranial implant is further provided with predefined locations for positioning of the ultrasound transducer.

15. A craniofacial implant, comprising:
a low profile intercranial device including a static cranial implant and a functional neurosurgical implant, the static cranial implant being sonolucent and including an outer first surface and an inner second surface; and
an ultrasound transducer in the form of an array of ultrasound transducers that automatically adjusts frequency and gain of the ultrasound transducers to assist in gathering the necessary image data that then may be processed for patient diagnosis and treatment, the ultrasound transducer is integrally formed with the static cranial implant, wherein the ultrasound transducer works in conjunction with the functional neurosurgical implant that has been integrated into the static cranial implant.

16. The craniofacial implant according to claim 15, wherein ultrasound imaging through the static cranial implant allows for imaging confirmation of blood flow immediately after surgery.

17. The craniofacial implant according to claim 15, wherein ultrasound imaging through the static cranial implant allows for imaging confirmation of blood flow during follow-up examinations.

18. The craniofacial implant according to claim 15, wherein ultrasound imaging through the static cranial implant allows for imaging confirmation of blood flow to desired locations within a brain.

19. The craniofacial implant according to claim 15, wherein ultrasound imaging through the static cranial implant allows for imaging visualization of, and guidance during, interventional procedures to guide a wire and/or catheter through neurovasculature to a desired location in a brain.

20. The craniofacial implant according to claim 15, wherein ultrasound imaging through the static cranial implant allows for activation of a contrast agent as it passes a particular point of interest and is subjected to ultrasound for activation thereof.

21. The craniofacial implant according to claim 15, wherein ultrasound imaging through the static cranial implant allows for drug delivery.

22. The craniofacial implant according to claim 15, wherein the ultrasound transducer is pre-set to frequencies, gain, and/or field of view for imaging and interacting with neuroanatomy, the ultrasound transducer operating between 1 MHz and 9 MHz when the ultrasound transducer is used for imaging purposes and the ultrasound transducer operating between 150 KHz to 1.2 MHz when the ultrasound transducer is used for therapeutic purposes.

23. The craniofacial implant according to claim 7, wherein the ultrasound transducer operates at a frequency of approximately 1 MHz to approximately 3 MHz, a dynamic range of approximately 55 dB to approximately 65 dB, and a gain of approximately 55 dB to approximately 70 dB.

* * * * *